US006500637B1

(12) United States Patent
Mikoshiba et al.

(10) Patent No.: US 6,500,637 B1
(45) Date of Patent: Dec. 31, 2002

(54) NEUROGENESIS INDUCING GENES

(75) Inventors: Katsuhiko Mikoshiba, Wako (JP); Jun Aruga, Tsukuba (JP); Takeharu Nagai, Tokyo (JP); Katsunori Nakata, Tsuchiura (JP)

(73) Assignee: The Institute of Physical and Chemical Research, Saitama (JP)

( * ) Notice: Subject to any disclaimer, the term of this patent is extended or adjusted under 35 U.S.C. 154(b) by 0 days.

(21) Appl. No.: 09/342,325

(22) Filed: Jun. 29, 1999

Related U.S. Application Data

(63) Continuation-in-part of application No. 09/172,045, filed on Sep. 28, 1998, now Pat. No. 6,277,594.

(30) Foreign Application Priority Data

Mar. 31, 1998 (JP) .............................................. 10-86979
Apr. 30, 1998 (JP) ............................................ 10-121456

(51) Int. Cl.$^7$ ................................................ C12P 21/06
(52) U.S. Cl. ................... 435/69.1; 435/252.3; 435/325; 435/320.1; 435/458; 536/23.5
(58) Field of Search ...................... 536/23.5; 435/69.1, 435/252.3, 320.1, 325; 514/44

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 4,708,871 A | 11/1987 | Geysen | |
| 4,873,191 A | 10/1989 | Wagner et al. | |
| 4,965,188 A | 10/1990 | Mullis et al. | |

FOREIGN PATENT DOCUMENTS

WO      WO 90/08832      8/1990

OTHER PUBLICATIONS

Aruga; Accession No. D32167, 1999.*
Orkin et al.; Report and Recommendations of th e Panel to Assess the NIH Investment in Research on Gene Therapy, 1995.*
Deonarain; Ligand–targeted receptor–mediated vectors for gene delivery; 1998, Exp. Opin. Ther. Patents 8(1): 53–69.*
Rudinger; Characteristics of the amino acids as components of a peptide hormone sequence, 1972.*
Crystal; Transfer of Genes to Humans: Earkly Lessons and Obstacles to Success, 1995, Science vol. 270: 404–410.*
Miller et. al.; Targeted vectors for gene therapy, 1995, FASEB J. 9: 190–199.*
i Altaba, "Catching a Gli–mpse of Hedgehog," *Cell* 90:193–196 [1997].
Anderson and Young, Quantitative Filter Hybridization, in *Nucleic Acid Hybridization* [1985].
Aruga et al., "Identification and characterization of Zic4, a new member of the mouse *Zic* gene family," *Gene* 172:291–294 [1996].
Aruga et al., "The mouse *Zic* gene family: homologues of the Drosophila pair–rule gene odd–paired," *J. Biol. Chem.*, 271:1043–1047 [1996].
Aruga et al., "Mouse *Zic1* is involved in cerebellar development," *J. Neurosci.*, 18:284–293 [1998].
Aruga et al., "A novel zinc finger protein, *Zic*, is involved in neurogenesis, especially in the cell lineage of cerebellar granule cells," *J. Neurochem.*, 63:1880–1890 [1994].
Becker et al., "High–efficiency transformation of yeast by electroporation," *Methods Enzymol.*, 194:182–187 [1990].
Benedyk et al., "Odd–paired: a zinc finger pair–rule protein required for the timely activation of engrailed and wingless in Drosophila embryos," *Genes Dev.*, 8:105–117 [1994].
Boshart et al., "A very strong enhancer is located upstream of an immediate early gene of human cytomegalovirus," *Cell* 41:521 [1985].
Bradley et al., "Formation of germ–line chimaeras from embryo–derived teratocarcinoma cell lines," *Nature* 309:255–258 [1984].
Brinster et al., "Factors affecting the efficiency of introducing foreign DNA into mice by microinjecting eggs," *Proc. Natl. Acad. Sci. USA* 82:4438–4442 [1985].
Chamberlin et al., "New RNA polymerase from *Escherichia coli* infected with bacteriophage T7," *Nature* 228:227–231 [1970].
Chitnis et al., "Primary neurogenesis in *Xenopus* embryos regulated by a homologue of the Drosophila neurogenic gene Delta," *Nature* 375:761–766 [1995].
Cimbora and Sakonju, "Drosophila midgut morphogenesis requires the function of the segmentation gene odd–paired," *Dev. Biol.*, 169:580–595 [1995].
Cohen et al., "Nonchromosomal antibiotic resistance in bacteria: genetic transformation of *Escherichia coli* by R–Factor DNA," *Proc. Natl. Acad. Sci. USA* 69:2110–2114 [1972].
Dijkema et al., "Cloning and expression of the chromosomal immune interferon gene of the rat," *EMBO J.* 4:761 [1985].
Doe et al., "Induction of HIV–1 envelope (gp 120)–specific cytotoxic T lymphocyte responses in mice by recombinant CHO cell–derived gp120 is enhanced by enzymatic removal of N–linked glycans," *Eur. J. Immunol.*, 24:2369–2376 [1994].
Erickson et al., "Hepatitis C virus–specific CTL responses in the liver of chimpanzees with acute and chronic hepatitis C," *J. Immunol.*, 151:4189–4199 [1993].
Erlich (ed.), *PCR Technology*, Stockton Press [1989].

(List continued on next page.)

*Primary Examiner*—James Ketter
*Assistant Examiner*—Richard Schnizer
(74) *Attorney, Agent, or Firm*—Medlen & Carroll, LLP

(57) ABSTRACT

The present invention relates to neurogenesis inducing genes. In particular, the present invention provides neurogenesis inducing genes coding for Zic proteins, vectors containing such genes, host cells containing such vectors, proteins produced by such host cells, antibodies raised to such proteins, and therapeutic agents or agents for gene therapy for nervous diseases.

7 Claims, 14 Drawing Sheets

OTHER PUBLICATIONS

Evans et al., "Establishment in culture of pluripotential cells from mouse embryos," *Nature* 292:154–156 [1981].

Ferreiro et al., "XASH genes promote neurogenesis in Xenopus embryos," *Development* 120:3649–3655 [1994].

Gebbia et al., "X–linked situs abnormalities result from mutations in *ZIC3*," *Nature Genet.*, 17:305–308 [1997].

Geysen et al. "Use of peptide synthesis to probe viral antigens for epitopes to a resolution of a single amino acid," *Proc. Natl. Acad. Sci USA* 81:3998–4002 [1984].

Geysen et al., "A priori delineation of a peptide which mimics a discontinuous antigenic determinant," *Mol. Immunol.*, 23:709–715 [1986].

Godsave et al., "Clonal analysis of mesoderm induction in *Xenopus laevis*," *Dev. Biol.* 134:486–490 [1989].

Gorman et al., "The Rous sarcoma virus long terminal repeat is a strong promoter when introduced into a variety of eukaryotic cells by DNA–mediated transfection," *Proc. Natl. Acad. Sci. USA* 79:6777–6781 [1982].

Gossler et al., "Transgenesis by means of blastocyst–derived embryonic stem cell lines," *Proc. Natl. Acad. Sci. USA* 83:9065–9069 [1986].

Graham and van der Eb, "A new technique for the assay of infectivity of human adenovirus 5 DNA,"*Virol.*, 52:456 [1973].

Grunz et al., "Neural differentiation of *Xenopus laevis* ectoderm takes place after disaggregation and delayed reaggregation without inducer," *Cell Differ. Dev.*, 28:211–218 [1989].

Hanahan, "Studies on transformation of *Escherichia coli* with plasmids," *J. Mol. Bio.*, 166:557–580 [1983].

Hanks et al., "Rescue of the En–1 mutant phenotype by replacement of En–1 with En–2," *Science* 269:679–682 [1995].

Harland, "In situ hybridization: an improved whole–mount method for Xenopus embryos," *Methods in Cell Biology* 36:685–694 [1991].

Haskell and Bowen, "Efficient production of transgenic cattle by retroviral infection of early embryos," *Mol. Reprod. Dev.* 40:386 [1995].

Hemmati–Brivanlou et. al., "Cephalic expression and molecular characterization of *Xenopus En–2*," *Development* 111(3):715–724 [1991].

Hemmati–Brivanlou et al., "Follistatin, an antagonist of activin, is expressed in the Spemann Organizer and displays direct neuralizing activity," *Cell* 77:283–295 [1994].

Hinnen et al., "Transformation of yeast," *Proc. Natl. Acad. Sci. USA* 75:1929–1933 [1978].

Hogan et al., in *Manipulating the Mouse Embryo*, Cold Spring Harbor Laboratory Press, Cold Spring Harbor, N.Y. [1986].

Hopwood et al., "A Xenopus mRNA related to Drosophila twist is expressed in response to induction in the mesoderm and the neural crest," *Cell* 59:893–903 [1989].

Ito et al., "Transformation of intact yeast cells treated with alkali cations," *J. Bacteriol.*, 153:163–168 [1983].

Jaenisch, "Germ line integration and mendelian transmission of the exogenous Moloney Leukemia Virus," *Proc. Natl. Acad. Sci. USA* 73:1260–1264 [1976].

Jaenisch, "Transgenic animals," *Science* 240:1468–1474 [1988].

Jahner et al., "De novo methylation and expression of retroviral genomes during mouse embryogenesis," *Nature* 298:623–628 [1982].

Jahner et al., "Insertion of the bacterial *gpt* gene into the germ line of mice by retroviral infection," *Proc. Natl. Acad Sci. USA* 82:6927–6931 [1985].

Jones and Woodland, "Development of the ectoderm in Xenopus: tissue specification and the role of cell association and division," *Cell* 44:345–355 [1986].

Kacian et al., "A replicating RNA molecule suitable for a detailed analysis of extracellular evolution and replication," *Proc. Natl. Acad. Sci. USA* 69:3038–3042 [1972].

Kim et al., "Use of the human elongation factor 1α promoter as a versatile and efficient expression system," *Gene* 91:217–223 [1990].

Kintner and Melton, "Expression of Xenopus N–CAM RNA in ectoderm is an early response to neural induction," *Development* 99:311–325 [1987].

Lamb et al., "Neural induction by the secreted polypeptide Noggin," *Science* 262:713–718 [1993].

Lee et al., "Conversion of Xenopus ectoderm into neurons by NeuroD, a basic helix–loop–helix protein," *Science* 268:836–844 [1995].

Maniatis et al., "Regulation of Inducible and Tissue–Specific Gene Expression," *Science* 236:1237–1245 [1987].

Mayor et. al., "Induction of the prospective neural crest of Xenopus," *Development* 121:767–777[1995].

Mizuseki et al., "*Xenopus* Zic–related–1 and Sox–2, two factors induced by chordin, have distinct activities in the initiation of neural induction," *Development* 125:579–587 [1998].

Mizushima and Nagata, "pEF–BOS, a powerful mammalian expression vector," *Nuc. Acids. Res.* 18:5322 [1990].

Moon and Christian, "Microinjection and expression of synthetic mRNAs in Xenopus embryos," *Technique* 1:76–89 [1989].

Nagai et al., "The expression of the mouse *Zic1*, *Zic2* and *Zic3* gene suggests an essential role for *Zic* genes in body pattern formation," *Dev. Biol.*, 182:299–313 [1997].

Nakata et al., "*Xenopus Zic3*, a primary regulator both in neural and neural crest development," *Proc. Natl. Acad. Sci. USA* 94:11980–11985 [1997].

Newport et al., "A major developmental transition in early Xenopus embryos: I. characterization and timing of cellular changes at the midblastula stage," *Cell* 30:675–686 [1982].

Nieuwkoop and Faber, "Normal Table of *Xenopus laevis* (Daudin): a systematical and chronological survey of the development from the fertilized egg till the end of metamorphosis," North–Holland Publishing Company, Amsterdam [1967].

Oschwald et al., "Localization of a nervous system–specific class II β–tubulin gene in *Xenopus laevis* embryos by whole–mount in situ hybridization," *Int. J. Dev. Biol.* 35:399–405 [1991].

Pannese et al., "The Xenopus homologue of Otx2 is a maternal homeobox gene that demarcates and specifies anterior body regions," *Development* 121:707–720 [1995].

Pavletich and Pabo, "Crystal structure of a five–finger GLI–DNA complex: new perspectives on zinc fingers," *Science* 261, 1701–1707 [1993].

Pearson et al., "Improved tools for biological sequence comparison," *Proc. Natl. Acad. Sci. USA* 85:2444–2448 [1988].

Robertson et al., "Germ–line Transmission of Genes Introduced into cultured Pluripotential Cells by Retroviral Vector," *Nature* 322:445–448 [1986].

Sambrook et al., *Molecular Cloning: A Laboratory Manual*, 2nd ed., Cold Spring Harbor Laboratory Press, New York [1989], pp. 16.6–16.15.

Sasai et al., "Xenopus chordin: a novel dorsalizing factor activated by organizer–specific homeobox genes." *Cell* 79:779–790 [1994].

Sasai et al., "Regulation of neural induction by the Chd and Bmp–4 antagonistic patterning signals in Xenopus," *Nature* 376:333–336 [1995].

Shain and Zuber, "Sodium dodecyl sulfate (SDS)–based whole–mount in situ hybridization of *Xenopus laevis* embryos," *J. Biochem. Biophys. Methods* 31:185–188 [1996].

Stewart et al., "Expression of Retroviral Vectors in Transgenic Mice Obtained by Embryo Infection," *EMBO J.* 6:383–388 [1987].

Suzuki et al., "Bone morphogenic protein acts as a ventral mesoderm modifier in early Xenopus embryos," *Develop. Growth Differ.*, 37:581–588 [1995].

Takebayashi et al., "Conversion of ectoderm into a neural fate by ATH–3, a vertebrate basic helix–loop–helix gene homologous to Drosophila proneural gene *atonal*," *EMBO J.*, 16:384–395 [1997].

Turner and Woodland, "H3 and H4 histone cDNA sequences from Xenopus: a sequence comparison of H4 genes," *Nucleic Acids Res.*, 10:3769–3780 [1982].

Turner and Weintraub, "Expression of achaete–scute homolog 3 in Xenopus embryos converts ectodermal cells to a neural fate," *Genes Dev.*, 8:1434–1447 [1994].

Uetsuki, et al., "Isolation and Characterization of the Human Chromosomal Gene for Polypeptide Chain Elongation Factor–1α," *J. Biol. Chem.*, 264:5791–5798 [1989].

Unanue et al., "The basis for the immunoregulatory role of macrophages and other accessory cells," *Science* 236:551–557 [1987].

Van der Putten, "Efficient insertion of genes into the mouse germ line via retroviral vectors," *Proc. Natl. Acad. Sci. USA* 82(18):6148–6152 [1985].

Voss et al., "The role of enhancers in the regulation of cell–type–specific transcriptional control," *Trends Biochem. Sci.*, 11:287–289 [1986].

Wilson and Hemmati–Brivanlou, "Induction of epidermis and inhibition of neural fate by Bmp–4," *Nature* 376:331–333 [1995].

Witta et al., "*XIPOU2*, a noggin–inducible gene, has direct neuralizing activity," *Development* 121:721–730 [1995].

Wright et. al., "The Xenopus X1Hbox6 homeo protein, a marker of posterior neural induction, is expressed in proliferating neurons," *Development* 109: 225–234 [1990].

Wu and Wallace, "The Ligation Amplification Reaction (LAR)–Amplification of Specific DNA Sequences Using Sequential Rounds of Template–Dependent Ligation," *Genomics* 4:560–569 [1989].

Yokota et al., "Predominant expression of human *Zic* in cerebellar granule cell lineage and medulloblastoma," *Cancer Res.* 56:377–383 [1996].

Zimmerman et al., "XASH–3, a novel *Xenopus achaete–scute* homolog, provides an early marker of planar neural induction and position along the mediolateral axis of the neural plate," *Development* 119:221–231 [1993].

Zimmerman et al., "The Spemann Organizer signal noggin binds and inactivates bone morphogenetic protein 4," *Cell* 86:599–606 [1996].

Anderson, "Human gene therapy," *Nature* 392 [Supplement, Apr. 30]:25–30 [1998].

Eck and Wilson, In *Goodman and Gilmans the Pharmacological Basis of Therapeutics*, Ninth Edition, McGraw–Hill Publishers, pp. 77–101 [1995].

Frade et al., "Insulin–like growth factor–1 stimulates neurogenesis in chick retina by regulating expression of the α6 integrin subunit," *Development* 122:2497–2506 [1996].

Upton et al., "Production and characterization of recombinant chicken insulin–like growth factor–I from *Escherichia coli*," *Mol. Endocrinol.* 9:83–92 [1992].

Verma and Somia, "Gene therapy—promises, problems and prospects," *Nature* 389:239–242 [1997].

Nakata et al., "*Xenopus Zic* family and its role in neural and neural crest development," *Mechanisms of Development* 75:43–51 [1998].

\* cited by examiner

```
MLLDAGAQYPAIGVTTFGSSRHHSAGDVTDREVALGINPFADGMGAFKLNPSSHDLASGQ    60
TAFTSQAPGYAAAALGHHHHPGHVSSYSSAAFNSTRDFLFRNRGFGEAASAQHSLFASAA   120
GGFPGPHGPHADTTGHLIFPGLHEQAASHASPNVVNGQMRLGFSGDMYGRPDQYGQVTSP   180
RSEHYASSQLHGYGPMNMNMAAHHGAGAFFRYMRQPIKQELICKWIEPEQLANPKKSCNK   240
TFSTMHELVTHVTVEHVGGPEQSNHICVWEECPREGKPFKAKYKLINHIRVHTGEKPFPC   300
PFPGCGKVFARSENLKIHKRTHTGEKPFKCEFEGCDRRFANSSDRKKHMHVHTSDKPYLC   360
KMCDKSYTHPSSLRKHMKVHEASSQGSQPSPAASSGYESSTPPTIVSPSAENQSTSSLSP   420
SSSAVHHTSNHSTLSSNFNEWYV                                       443
```

B

```
MLLDAGPQFPALGVGTFARHHHHHHHAAVAAAAAAAAEMQERELSLAQNTFVEPTHMGAF    60
KLNPGGGSGGGSGGGGGGGGAGPNGGAGASGPHDLSPPGQTSAFTSQAGYPTSALAPHSA   120
YSGAAAFNSPRDFLFRGRGFAEGSAAAGGGQHGLFGPPAGSLHHHPHHHHQLSHAEHPQG   180
HLLFPGIHDQHAAASQNTLGGQMRLGLPGEVFGRTEQYRQVSSPRGDPYTAAQLHNQYSP   240
MNMGMNMAAHHHHHHHHHPGAFFRYMRQPCIKQELICKWIDPEQLNNPKKSCTKTFSTMH   300
ELVTHVSVEHVGGPEQSNHICFWEECPREGKPFKAKYKLVNHIRVHTGEKPFPCPFPGCG   360
KVFARSENLKIHKRTHTGEKPFQCEFEGCDRRFANSSDRKKHMHVHTSDKPYLCKMCDKT   420
YTHPSSLRKHMKVHETSPQGSESSPAASSGYESSTPPGLVSPNSETQNPNLSPAAAAVSA   480
VHNVSSGASGALASNFNEWYV                                         501
```

FIG. 8 continued

```
C                                                          Finger 1
XZic1   205  GAGAFFRYMR-QP------IKQELICKWIEPEQ--LANPK--KS    237
XZic2   258  HP***F****-*PC-----I***LI*K*IDPEQ--LNNPK--KS    291
XZic3   206  GP***F****-*P------I***LS*K*LEEST--MNMPQ--KT    238
mZic1   209  GA***F****-*P------I***LI*K*IEPEO--LANPK--KS    241
mZic2   239  HP***F****-*QC-----I***LI*K*IDPEO--LSNPK--KS    272
mZic3   232  GP***F****-*P------I***LS*K*IEEAO--LSRPK--KS    264
mZic4   119  GP***F****-*P------I***LI*K*LGDDSP-MS-PRP---    150
Opa     187  GA***L****H*PASSASSV***MQ*L*IDPDQPGLVPPGGRKT    230
                                                          Finger 2
XZic1   238  CNKTFSTMHELVTHVTVEHVGGPEQSNHICVWEECPREGKPFKA    281
XZic2   292  *TKT*ST***L*T*VSV*******QSN*I*F*EE*P*E*KP***    335
XZic3   239  *DRT*SS***L*T*MTM*******QNN*I*Y*EE*P*G*KS***    282
mZic1   242  *NKT*ST***L*T*VTV*******QSN*I*F*EE*P*E*KP***    285
mZic2   273  *NKT*ST***L*T*VSV*******QSN*V*F*EE*P*E*KP***    316
mZic3   265  *DRT*ST***L*T*VTM*******QNN*V*Y*EE*P*E*KS***    308
mZic4   151  *SKT*ST***L*T*VTV*******QAN*I*F*EE*P*O*KP***    194
Opa     231  *NKV*HS***I*T*LTV*******CTT*A*F*VG*S*N*RP***    274
                                                          Finger 3
XZic1   282  KYKLINHIRVHTGEKPFPCPFPGCGKVFARSENLKIHKRTHTGE    325
XZic2   336  **V********PF**V****************    379
XZic3   283  **V********PF**I****************    326
mZic1   286  **V********PF**V****************    329
mZic2   317  **V********PF**V****************    360
mZic3   309  **V********PF**I****************    352
mZic4   195  **V********PF**V****************    238
Opa     275  **V********AH**V****************    318
                        Finger 4                  Finger 5
XZic1   326  KPFKCEFEGCDRRFANSSDRKKHMHVHTSDKPYLCKM--CDKSY    367
XZic2   380  *QFED***********M*******L*KM--***T*    421
XZic3   327  *KFED***********M*******I*KV--***S*    368
mZic1   330  *KFED***********M*******L*KM--***S*    367
mZic2   361  *QFED***********M*******L*KM--***S*    402
mZic3   353  *KFED***********M*******I*KV--***S*    394
mZic4   239  *RFEE***********S*******M*KVRG***C*    282
Opa     319  *KHED***********S*******N*RING***S*    362

XZic1   368  THPSSLRKHMKVHEAS         383
XZic2   422  ************ETS          437
XZic3   369  ************ESQ          384
mZic1   372  ************ESS          387
mZic2   403  ************ESS          425
mZic3   395  ************ESQ          410
mZic4   283  ************GRS          298
Opa     363  ************GNV          378

D
XZic1    92  FNS--TRDFLF-RNR          103
XZic2   127  FNS--PRDFLF-RGR          138
XZic3    91  FNS--TRDFLF-RNR          102
mZic1    94  FNS--TRDFLF-RNR          105
mZic2   113  FNS--TRDFLF-RQR          124
mZic3   111  FNS--TRDFLF-RQR          122
Opa      79  FNSYASRDFLLGR-R           92
```

NEUROGENESIS INDUCING GENES

This application is a continuation-in-part and claims priority benefit of pending U.S. patent application Ser. No. 09/172,045, filed Sep. 28, 1998, now US. Pat. No. 6,277, 594, which claims priority benefit to Japanese patent application numbers 86979/1998, filed Mar. 31, 1998, and 121456/1998, filed Apr. 30, 1998.

FIELD OF THE INVENTION

The present invention relates to neurogenesis inducing genes.

BACKGROUND OF THE INVENTION

The early process of vertebrate neurogenesis is divided into several basic processes, such as differentiation into the neural plate (neural induction) and formation and maturation of the neural network from the ectoderm. This early process includes occurrence of neural precursor cells, pattern formation of the nervous system, and proliferation and differentiation of neural precursor cells.

It is known that the early neurogenesis of *Xenopus laevis* is induced by blockade of BMP4 (i.e., Bone Morphogenetic Protein 4) signals by noggin, chordin, etc. (Sasai et al., Nature, 376:333 [1995]; and Mizuseki et al., Development 125:579–587 [1998]). BMP4 is a factor which induces the ectoderm into epidermal cells. When BMP4 is activated, cells differentiate into the epidermis. Proneural genes (e.g., Neurogenin, NeuroD, XASH-3, XATH-3) which are involved in the control of neural induction (i.e., Neurogenesis, neural differentiation) and in the coding for basic helix-loop-helix(bHLH) transcription factors are also known. However, the factors involved in the blockade of BMP4 signals to proneural genes are still unknown.

Understanding the molecular basis of higher brain functions is important, not only to elucidate the universal principle of these processes, but also in the development of new therapeutic methods for treatment of diseases involving brain functions (i.e., neurogenesis).

SUMMARY OF THE INVENTION

The present invention provides neurogenesis inducing proteins, genes coding for the proteins; recombinant vectors comprising the genes, transformants comprising the vectors, an antibodies against the proteins; and therapeutic agents for nervous diseases.

In one embodiment, the present invention relates to a recombinant protein having a protein comprising at least a portion of the amino acid sequence set forth in SEQ ID NO:2. In some embodiments, the present invention provides a protein which consists of the amino acid sequence shown in SEQ ID NO: 2 having a deletion, substitution, or addition of at least one amino acid and which has neurogenesis inducing activity. In another embodiment, the present invention relates to a neurogenesis inducing gene encoding for a protein comprising at least a portion of the amino acid sequence set forth in SEQ ID NO:2 or a neurogenesis inducing gene encoding for a protein comprising at least a portion of the amino acid sequence set forth in SEQ ID NO:2 having a deletion, substitution, or addition of at least one amino acid and which has neurogenesis inducing activity. The present invention also relates to a gene which hybridizes with the neurogenesis inducing gene encoding for a protein comprising at least a portion of the amino acid sequence set forth in SEQ ID NO:2.

In another embodiment, the present invention relates to a gene comprising a DNA sequence having at least a portion of the nucleotide sequence set forth in SEQ ID NO: 1. The present invention also relates to a DNA which hybridizes with a DNA having at least a portion of the nucleotide sequence set forth in SEQ ID NO:1, and which codes for a protein having neurogenesis inducing activity.

In another embodiment, the present invention relates to an isolated nucleic acid encoding a protein having at least a portion of the amino acid sequence selected from the group consisting of SEQ ID NO: 2, SEQ ID NO: 42 and in SEQ ID NO: 44. In one embodiment, the nucleic acid comprises a nucleotide sequence having at least a portion of the sequence selected from the group consisting of SEQ ID NO: 1, SEQ ID NO: 41, and SEQ ID NO: 43. In preferred embodiments, the present invention provides a nucleic acid encoding a neurogenesis inducing gene (e.g., early neurogenesis inducing gene). In particular, the present invention provides a nucleic acid encoding a gene selected from the group consisting of Zic1, Zic 2, and Zic3 genes. In one embodiment, the gene is a Xenopus gene.

The present invention further relates to a nucleic acid capable of hybridizing to a nucleic acid comprising a nucleotide sequence having at least a portion of the sequence selected from the group consisting of SEQ ID NO:1, SEQ ID NO: 41, and SEQ ID NO: 43. In a preferred embodiment, the nucleic acid capable of hybridizing under stringent conditions.

In yet another embodiment, the present invention also relates to recombinant vectors comprising at least a portion of genes described above. The present invention further relates to transformants (e.g., a host cell) comprising the recombinant vectors of the present invention.

The present invention also relates to compositions comprising a protein having at least a portion of the amino acid sequence selected from the group consisting of SEQ ID NO: 2, SEQ ID NO: 42, and SEQ ID NO: 44. In one embodiment, the protein is selected from the group consisting of Zic1, Zic2, and Zic3 proteins. In another embodiment, the protein is a Xenopus protein. In yet another embodiment, the protein is a recombinant protein.

The present invention also provides antibodies against the above described proteins. In particular, the present invention relates to a purified antibody specific to a protein having at least a portion of the amino acid sequence selected from the group consisting of SEQ ID NO: 2, SEQ ID NO: 42, and SEQ ID NO: 44. The present invention further provides therapeutic agents for nervous diseases associated with the above proteins (e.g., in the presence or absence of the proteins). In preferred embodiments, the present invention relates to therapeutic agents or agents for gene therapy of nervous diseases including, but not limited to Alzheimer's disease, amyotrophic lateral sclerosis, spinocerebellar degeneration, Parkinson's disease and cerebral ischemia, although it is not intended that the present invention be limited to therapeutic agents related to these diseases.

Furthermore, the present invention relates to methods for producing a neurogenesis inducing protein, comprising, for example, the steps of culturing a transformant comprising a recombinant vector discussed above and recovering the neurogenesis inducing protein from the resultant culture. In one embodiment, the methods of the present invention comprises the steps of: a) providing a composition comprising a recombinant vector, wherein the recombinant vector comprises a nucleic acid having at least a portion of the sequence selected from the group consisting of SEQ ID NO:

1, SEQ ID NO: 41 and SEQ ID NO: 43, and a host cell; b) transforming the recombinant vector into the host cell to produce a transformant; and c) culturing the transformant to produce a neurogenesis inducing protein. In one embodiment, the methods of the present invention further comprises the step of d) isolating the neurogenesis inducing protein. In preferred embodiments, the neurogenesis inducing protein is an early neurogenesis inducing protein.

Further, the present invention relates to methods for gene therapy, comprising the steps of: a) providing i) a subject, and ii) a composition comprising a nucleic acid having at least a portion of the sequence selected from the group consisting of SEQ ID NO: 1, SEQ ID NO: 41 and SEQ ID NO: 43; and b) delivery the composition to the subject. In preferred embodiments, the subject suffers from a disease selected from the group consisting of Alzheimer's disease, amyotrophic lateral sclerosis, spinocerebellar degeneration, Parkinson's disease and cerebral ischemia.

BRIEF DESCRIPTION OF THE DRAWINGS

FIG. 8 shows the sequences of Xenopus Zic1 and Zic2. Panel A and Panel B provide the predicted amino acid sequences of Xenopus Zic1 (SEQ ID NO:42) and Zic2 (SEQ ID NO:44), respectively. In both panels, the underlining indicates the location of the zinc finger motif. Panel C shows the alignment of the zinc finger domain of Xenopus Zic1 (SEQ ID NO:50), Zic2 (SEQ ID NO:51), Zic3 (SEQ ID NO:52; and Nakata et al., "Xenopus Zic3, a primary regulator both in neural and neural crest development," Proc. Natl. Acad. Sci. USA 94:11980–11985 [1997]), mouse Zic1 (SEQ ID NO:53; and Aruga et al., "A novel zinc finger protein, Zic, is involved in neurogenesis, especially in the cell lineage of cerebellar granule cells," J. Neurochem. 63: 1880–1890 [1994]), Zic2 (SEQ ID NO:54), Zic3 (SEQ ID NO:55) and Zic 3 (SEQ ID NO:56; Aruga et al., "The mouse Zic gene family Homologues of the Drosophila pair-rule gene odd-paired," J. Biol. Chem. 271: 1043–1047 [1996]; Aruga et al., "Identification and characterization of Zic4, a new member of the mouse Zic gene family," Gene 172: 291–294 [1996]) and Opa (SEQ ID NO:57; and Benedyk et al., "Odd-paired: a zinc finger pair-rule protein required for the timely activation of engrailed and wingless in Drosophila embryos," Genes. Dev. 8: 105–117 [1994]). The asterisks indicate the amino acids conserved among all eight proteins. The bold letters and asterisks indicate the cysteine and histidine residues of the C2H2 motif. Panel D shows a conserved portion of the N-terminal region among Zic family (SEQ ID NOS:58–63) and Opa (SEQ ID NO:64).

GENERAL DESCRIPTION OF THE INVENTION

Figure 1:
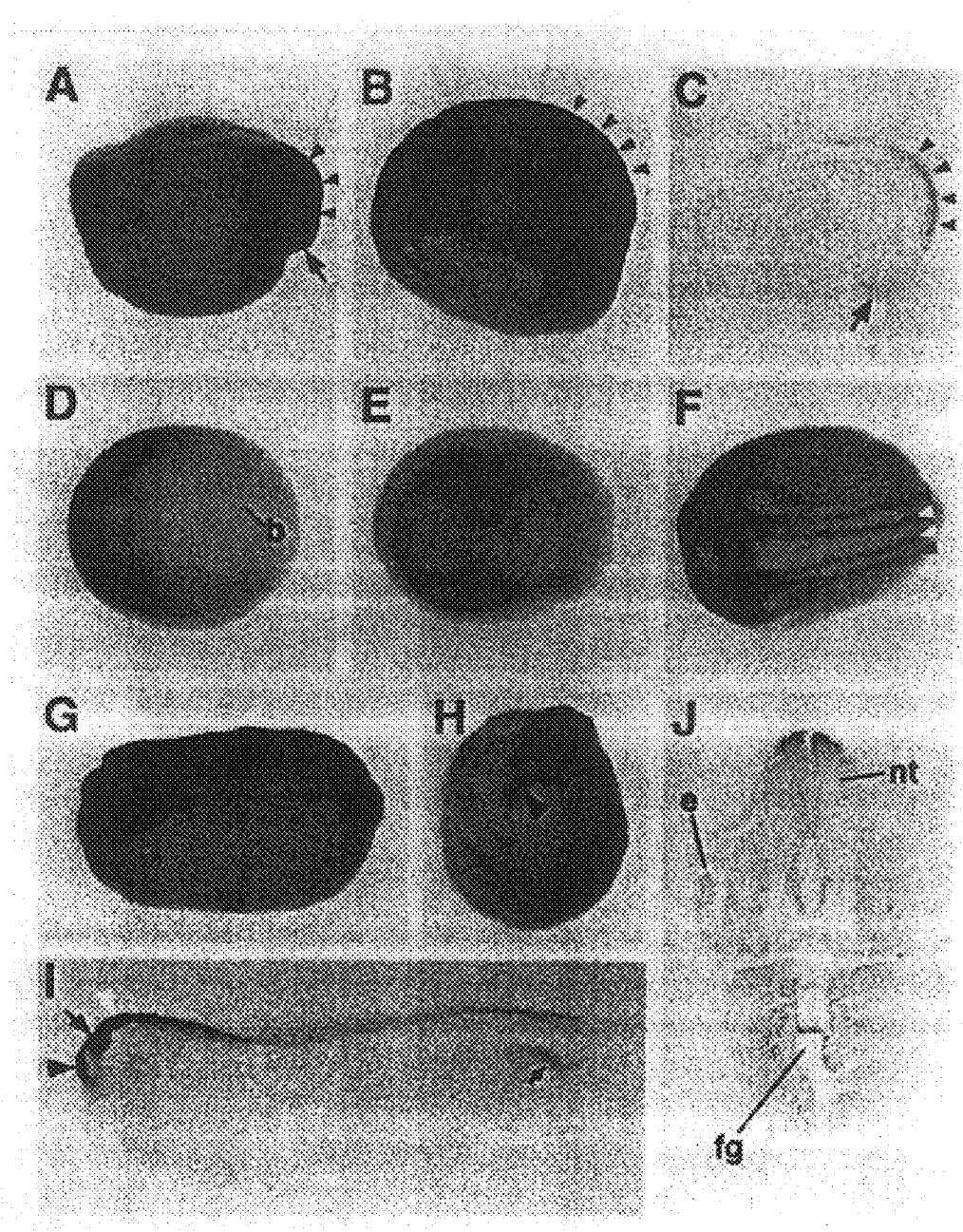
FIG. 1 panels a–j, present photographs showing the results of expression tests of the Zic3 gene of the invention (morphology of an organism).

The present invention relates to genes capable of inducing neurogenesis (e.g., early neurogenesis). In particular, the present invention relates to Zic1, Zic2, and Zic 3 genes, vectors containing such genes, host cells containing such vectors, proteins produced by such host cells, antibodies raised to such proteins, and therapeutic agents or agents for gene therapy of nervous diseases.

The Zic family was originally identified as a group of genes encoding zinc finger proteins expressed in adult mouse cerebella (Aruga et al., J. Neurochem 63: 1880–1890 [1994], supra). In mice, at least four kinds of Zic genes have been identified (Aruga et al., J. Neurochem 63: 1880–1890 [1994], supra; Aruga et al., J. Biol. Chem. 271: 1043–1047 [1996], supra; Aruga et al., Gene 172: 291–294 [1996], supra). These zinc finger proteins share a highly conserved domain consisting of five tandemly repeated $C_2H_2$-type zinc finger motifs. The motifs are highly conserved among various species (Benedyk et al., supra; Cimbora and Sakonju, "Drosophila midgut morphogenesis requires the function of the segmentation gene odd-paired," Dev. Biol. 169: 580–595 [1995]; Yokota et al., "Predominant expression of human Zic in cerebellar granule cell lineage and medulloblastoma," Cancer Res. 56: 377–383 [1996]; Gebbia et al., "X-linked situs abnormalities result from mutations in ZIC3," Nature Genet. 17: 305–308 [1997]; Nakata et al., supra), including their Drosophila homologue odd-paired, which plays important roles in parasegmental subdivision and visceral mesoderm development of the Drosophilia embryo.

The mouse Zic1, Zic 2, and Zic3 genes are expressed in a similar but distinct manner during gestational development (Nagai et al., "The expression of the mouse Zic1, Zic2 and Zic3 gene suggests an essential role for Zic genes in body pattern formation," Dev. Biol. 182: 299–313 [1997]). The expression of these genes was detectable at the primitive streak stage and later in neural tissue, somites and limb buds. Although they are expressed in overlapping sites, their respective expression patterns are not identical. These findings suggest that each Zic gene has specific roles in vertebrate development. This has been confirmed in functional studies. For example, the disruption of mouse Zic1 gene results in malformation of the central nervous system, particularly, the cerebellum (Aruga et al., "Mouse Zic1 is involved in cerebellar development," J. Neurosci. 18: 284–293 [1998]), whereas a mutation in human Zic3 results in disturbance of the left to right body axis (Gebbia et al., supra). The present invention contemplates that Zic genes constitute a multigene family in other vertebrates, and that their respective roles are not identical, although an understanding of the mechanism is not necessary in order to practice the present invention, nor is it intended that the present invention be so limited.

In some embodiments, the present invention relates to the role of Xenopus Zic genes in early vertebrate development. Xenopus Zic3 gene has been cloned (Nakata et al., supra). Expression of Xenopus Zic3 is detected in the prospective neural plate region at gastrulation. The onset of its expression is earlier than those of most proneural genes and follows chordin expression. Zic3 expression is induced by blockade of the BMP4 signal. Overexpression of Zic3 results in hyperplastic neural and neural crest-derived tissue. In an animal cap explant, overexpression of Zic3 induces expression of proneural genes such as Neurogenin (Xngnr-1) and neural crest genes. These findings show that Xenopus Zic3 can determine ectodermal cell fate and promote the earliest step of neural and neural crest development.

Experiments conducted during the development of the present invention further identified and characterized Xenopus Zic-related genes, Zic1 and Zic2, and examined their expression patterns and functions. At least three Zic genes exist in *Xenopus laevis*, and their respective homologues in mice had been reported. The homologues of Zic1, Zic2 and Zic3 have also been confirmed in some other vertebrates (See e.g., Yokota et al., supra; and Gebbia et al., supra), suggesting that Zic1, Zic2 and Zic3 is important in the vertebrate development.

The present invention has determined the expression patterns of the three Zic genes in Xenopus embryos (Table 1) (See also, Nakata et al., supra). Table 1 shows several similarities and differences among the three Zic genes. First of all, Zic2 was maternally expressed. The definitive roles of Zic2 during this period remains unclear at this time. Although an understanding of the mechanisms is not necessary for the practice of the present invention and the present invention is not limited to any particular mechanism, post-transcriptional regulatory mechanisms may work. Some other genes involved in early neural development have also been detected as maternal messages (e.g., Otx2, Neurogenin; See also, Pannese et al., "The Xenopus homologue of Otx2 is a maternal homeobox gene that damarcates and specifies anterior body regions," Development 121: 707–720 [1995]). The role of Zic1 and Zic2 before zygotic transcription is clarified further below.

The three Xenopus Zic genes have similar expression patterns in neural tissue. All three genes are expressed in the prospective neural plate region at the time of neural induction. Expression in the medial part of the neural plate was diminished while that in the neural plate border region increased. Thereafter, expression increased on the anterior and dorsal side with regard to the anterior-posterior and dorsal-ventral axes, respectively. These patterns of expression show that Zic genes play a role in neural induction and the patterning of neural tissues in the early phase of neural development.

TABLE 1

Comparative summary of the expression of the three Zic genes:

| Stage | Tissues | Zic1 | Zic2 | Zic3 |
|---|---|---|---|---|
| 9 (blastula) | Ectoderm | +++ | +++ | − |
| 10.5 (gastrula) | Prospective neural plate | ++ | ++ | +++ |
| | Prospective epidermis | − | + | − |
| 14–16 (neurula) | Neural fold | +++ | +++ | +++ |
| 20 (early tailbud) | Dorsal brain | ++ | ++ | ++ |
| | Dorsal spinal cord | ++ | ++ | + |
| | Eye vesicle | − | +++ | − |
| | Somite | +++ | ++ | − |
| 30 (tailbud) | Telencephaon | ++ | + | − |
| | Diencephalon | ++ | + | +++ |
| | Mesencephalon | ++ | + | ++ |
| | Rhombencephalon | ++ | + | ++ |
| | Dorsal spinal cord | ++ | ++ | + |
| | Eye (ciliary marginal zone) | − | +++ | − |
| | Somite | +++ | ++ | − |
| | Lateral mesoderm (tail) | − | − | ++ |
| | Cement gland | − | + | − |
| | Posterior ventral epidermis | − | + | − |

The differences in spatial Zic gene expression in neural tissues were principally different levels of expression along the anterior-posterior axis and expression in the eye (see Table 1). In addition to the expression in neural tissues, that in somites and their derivatives showed variability. In particular, Xenopus Zic1 is strongly expressed in the somites. It was found that mouse Zic1 is similarly expressed in the somites and plays a critical role in the development of somite derivatives (Nagai et al., supra), suggesting that the Xenopus Zic1 may also play a role in somite development.

The expression in somites is well correlated between Xenopus and mouse Zic genes in that the expression is high for Zic1 moderate for Zic2 and very low for Zic3 both in Xenopus and mouse. As a consequence, the expression patterns of Xenopus Zic1, Zic2, and Zic3 correspond to those of mouse Zic1, Zic2, and Zic3, respectively. Thus, the present invention contemplates that the roles of Zic1, Zic2, and Zic3 are generally well conserved between Xenopus and mouse.

Xenopus Zic1 and Zic2 are novel neuralizing factors. Experiments conducted during the development of the present invention showed that Xenopus Zic1 and Zic2 were capable of inducing neural and neural crest tissues. Zic1 or Zic2 overexpression in embryos resulted in the enlargement of neural plates and neural plate border regions in neurula and the appearance of ectopic pigment cells which were derived from the neural crest. Furthermore, overexpression leads to the induction of neural and neural crest markers in the animal cap explants. Thus, the present invention provides compositions that serve as regulators of neural and neural crest development.

Figure 11:
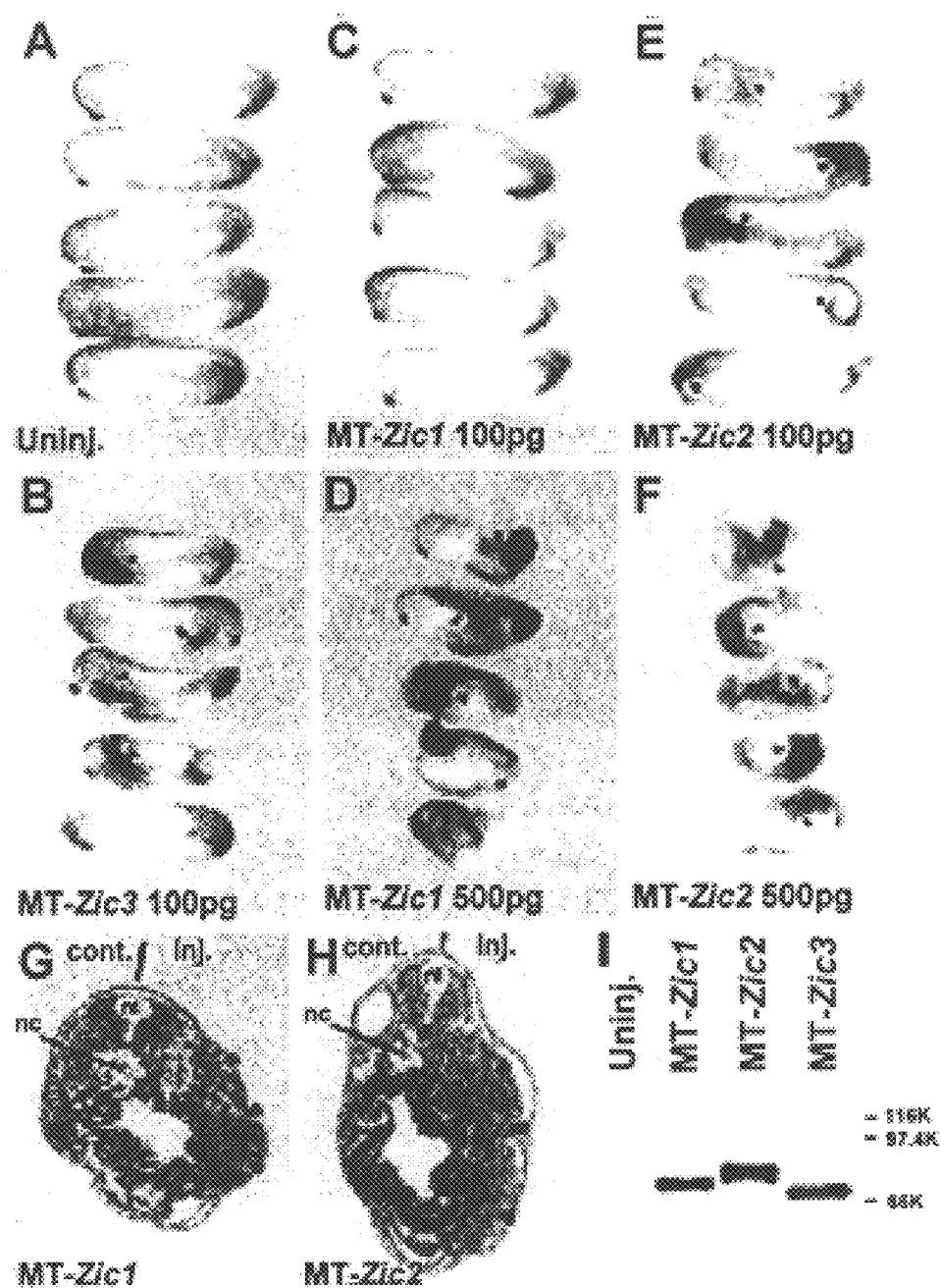
FIG. 11 panels A–I shows Zic1 or Zic2 overexpression induces ectopic pigment cell expression in embryo, as does overexpression of Zic3. A total of 100 or 500 pg of MT-Zic3 (B), MT-Zic1 (C, D), or MT-Zic2 (E, F) mRNA was injected into two blastomeres of 2-cell stage embryos, which were then cultured to stage 28–29. Clusters of pigment cells appeared in MT-Zic3, MT-Zic1 or MT-Zic2 mRNA-injected embryos (B,D,E,F, arrowheads). Transverse sections of MT-Zic1 (G) or MT-Zic2 (H) mRNA-injected embryos. A total of 250 pg of MT-Zic1 (G) or 125 pg of MT-Zic2 (H) mRNA was injected into one blastomere of 2-cell stage embryos and embryos were cultured to stage 35–36. Ectopic expression of presumptive mesenchymal tissues was observed in the MT-Zic1 or MT-Zic2 mRNA-injected side (G,H, arrow-heads). (I) Western blot analysis of each Zic protein level in MT-Zic3, MT-Zic1 or MT-Zic2 mRNA-injected embryos. A total of 100 pg of MT-Zic3, MT-Zic1 or MT-Zic2 mRNA was injected into two blastomeres of 2-cell stage embryos and cultured to stage 10.5. A total of 10 pg of protein prepared from whole embryo was analyzed by Western blot analysis using an anti-myc antibody.
Figure 14:
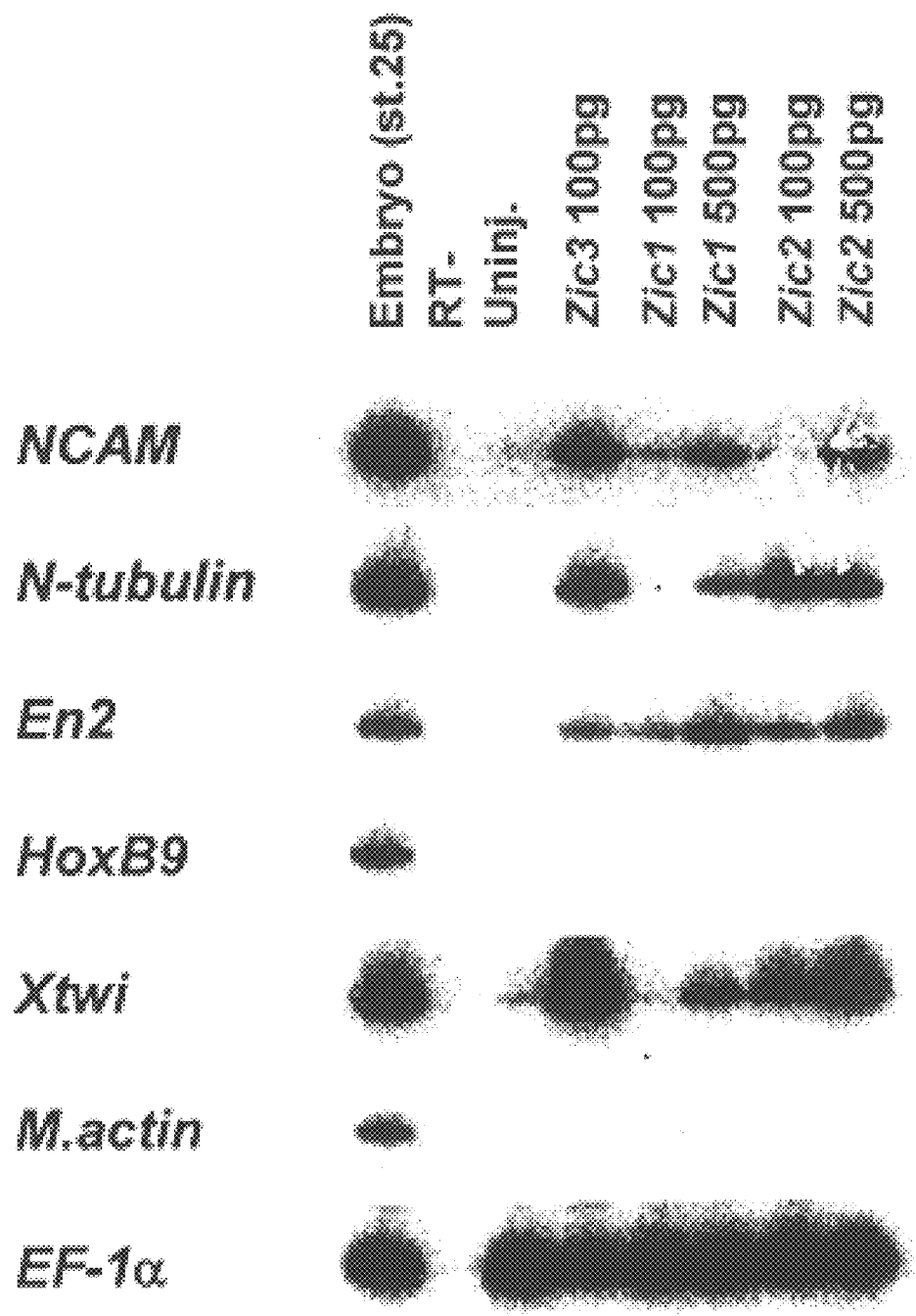
FIG. 14 shows that Zic1 and Zic2-induced anterior neural marker genes and a neural crest marker gene without mesoderm induction in animal cap explants, as seen with Zic3. Embryos were injected with MT-Zic3 or MT-Zic1 mRNA at the two-cell stage. Animal caps were explanted at stage 9 and cultured. When sibling embryos reached stage 25, the expression of anterior-posterior marker genes (En2 and HoxB9 [=Xlhbox6]), a pan-neural marker gene (NCAM), a neuronal differentiation marker (N-tubulin), a neural crest marker (Xtwi), and a dorsal mesodermal marker (M. actin; muscle actin) were examined by RT-PCR. Although uninjected (Uninj.) animal caps expressed none of these markers, animal caps injected with Zic1, Zic2, or Zic3 mRNA expressed the anterior marker (En2) and the neural crest marker (Xtwi) while expressing neither the posterior marker (HOXB9) nor the dorsal mesodermal marker (M.actin). In each experiment, sibling control embryos served as a positive control (Embryo) and PCR on the same RNA without reverse transcription was done to verify the absence of genomic DNA (RT-PCR).

The present invention demonstrates that Xenopus Zic3 is a primary regulator of neural and neural crest development (See also, Nakata et al., supra). The present invention also shows that Zic1 or Zic2 overexpression yielded essentially the same results as observed with Zic3 overexpression. Ectopic pigment cells in embryos overexpressing Zic2 were equivalent to those found in Zic3-overexpressing embryos. However, the induced ectopic pigment cells were less dense in the Zic1 -overexpressed embryos than in the Zic2 or Zic3-overexpressed embryos (FIG. 11). In addition, a larger amount of RNA was required to induce neural and neural crest markers in animal cap explants to the same extent (FIG. 14). Although an understanding of the mechanisms is not necessary for the practice of the present invention and the present invention is not limited to any particular mechanism, these results indicate that the potency of neural and neural crest induction by Zic1 is less than that of Zic2 and Zic3. This finding suggests that Zic1 may play a supportive role in the Zic2 and Zic3-mediated neural and neural crest induction. This situation is analogous to the relationship between mouse En1 and En2, in which the En1 and En2 proteins play the same roles in midbrain and hindbrain development (Hanks et al., "Rescue of the En-1 mutant phenotype by replacement of En-1 with En-2," Science 269, 679–682 [995]).

Definitions

To facilitate an understanding of the present invention, a number of terms and phrases are defined below:

As used herein, the term "early neurogenesis" refers to the process of neurogenesis related to the formation of the neural plate from the ectoderm (e.g., from the late blastula stage to the neurula stage of Xenopus embryos). The term "early neurogenesis inducing activity" refers to an activity which gives rise to the neural plate and other tissues (e.g., the neural crest) from the ectoderm. The term "neurogenesis" refers to the process of neurogenesis as a whole, including the development, differentiation, and maturation of the nervous system after the early neurogenesis.

The term "agonist," as used herein, refers to a molecule which, when interacting with an biologically active molecule, causes a change (e.g., enhancement) in the biologically active molecule, which modulates the activity of the biologically active molecule. Agonists may include proteins, nucleic acids, carbohydrates, or any other molecules which bind or interact with biologically active molecules. For example, agonists can alter the activity of gene transcription by interacting with RNA polymerase directly or through a transcription factor.

The terms "antagonist" or "inhibitor," as used herein, refer to a molecule which, when interacting with a biologically active molecule, blocks or modulates the biological activity of the biologically active molecule. Antagonists and inhibitors may include proteins, nucleic acids, carbohydrates, or any other molecules that bind or interact with biologically active molecules. Inhibitors and antagonists can effect the biology of entire cells, organs, or organisms (e.g., an inhibitor that slows neuron degeneration).

The term "modulate," as used herein, refers to a change in the biological activity of a biologically active molecule. Modulation can be an increase or a decrease in activity, a change in binding characteristics, or any other change in the biological, functional, or immunological properties of biologically active molecules.

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide or precursor (e.g., Zic1, Zic2, and Zic3). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mNRA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mNRA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., *Molecular Cloning: A Laboratory Manual*, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6–16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Also, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition below for "stringency").

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the. G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids which may be amplified by any amplification method. It is contemplated that "amplifiable nucleic acid" will usually comprise "sample template." As used herein, the term "sample template" refers to nucleic acid originating from a sample that is analyzed for the presence of "target". In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "antisense" is used in reference to DNA or RNA sequences that are complementary to a specific DNA or RNA sequence (e.g., mNRA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mNRA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mNRA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and antisense strands (i.e., the oligonucleotide or polynucleotide may be double-stranded).

As used herein, the term "purified" or "to purify" refers to the removal of contaminants from a sample. For example, antibodies are purified by removal of contaminating non-immunoglobulin proteins; they are also purified by the removal of immunoglobulin that does not bind to the target molecule. The removal of non-immunoglobulins proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "recombinant DNA molecule" as used herein refers to a DNA molecule that is comprised of segments of DNA joined together by means of molecular biological techniques. For example, "recombinant DNA vector" refers to DNA sequences containing a desired coding sequence and appropriate DNA sequences necessary for the expression of the operably linked coding sequence in a particular host organism.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will, in general, also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873191 describes a method for the micro-injection of zygotes; the disclosure of this patent is incorporated herein in its entirety.

Retroviral infection can also be used to introduce transgenes into an animal. The developing embryo can be cultured in vitro to the blastocyst stage. During this time, the blastomeres can be targets for retroviral infection (Janenich, Proc. Natl. Acad. Sci. USA 73:1260–1264 [1976]). Efficient infection of the blastomeres is obtained by enzymatic treatment to remove the zona pellucida (Hogan et al., in *Manipulating the Mouse Embryo,* Cold Spring Harbor Laboratory Press, Cold Spring Harbor, N.Y. [1986]). The viral vector system used to introduce the transgene is typically a replication-defective retrovirus carrying the transgene (D. Jahner et al., Proc. Natl. Acad Sci. USA 82:6927–693 [1985]). Transfection is easily and efficiently obtained by culturing the blastomeres on a monolayer of virus-producing cells (Van der Putten, supra; Stewart, et al., EMBO J. 6:383–388 [1987]). Alternatively, infection can be performed at a later stage. Virus or virus-producing cells can be injected into the blastocoele (D. Jahner et al., Nature 298:623–628 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

A third type of target cell for transgene introduction is the embryonal stem (ES) cell. ES cells are obtained by culturing pre-implantation embryos in vitro under appropriate conditions (Evans et al, Nature 292:154–156 [1981]; Bradley et al., Nature 309:255–258 [1984]; Gossler et al., Proc. Acad. Sci. USA 83:9065–9069 [1986]; and Robertson et al., Nature 322:445–448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468–1474 [1988]). Prior to the introduction of transfected ES cells into the blastocoel, the transfected ES cells may be subjected to various selection protocols to enrich for ES cells that have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

The terms "overexpression" and "overexpressing" and grammatical equivalents, are used in reference to levels of mNRA to indicate a level of expression approximately 3-fold higher than that typically observed in a given tissue in a control or non-transgenic animal. Levels of mNRA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene that is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp.16.9–16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "test compound" refers to any chemical entity, pharmaceutical, drug, and the like that can be used to treat or prevent a disease, illness, sickness, or disorder of bodily function. Test compounds comprise both known and potential therapeutic compounds. A "known therapeutic compound" refers to a therapeutic compound that has been shown (e.g., through animal trials or prior experience with administration to humans) to be effective in such treatment or prevention.

As used herein, the terms "host," "expression host," and "transformant" refer to organisms and/or cells which harbor an exogenous DNA sequence (e.g., via transfection), an expression vector or vehicle, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host.

As used herein, the term "antigen" refers to any agent (e.g., any substance, compound, molecule [including macromolecules], or other moiety), that is recognized by an antibody, while the term "immunogen" refers to any agent (e.g., any substance, compound, molecule [including macromolecules], or other moiety) that can elicit an immunological response in an individual. These terms may be used to refer to an individual macromolecule or to a homogeneous or heterogeneous population of antigenic macromolecules. It is intended that the term encompasses protein molecules or at least one portion of a protein molecule, which contains one or more epitopes. In many cases, antigens are also immunogens, thus the term "antigen" is often used interchangeably with the term "immunogen." The substance may then be used as an antigen in an assay to detect the presence of appropriate antibodies in the serum of the immunized animal.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or specifically binding-"when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The term "monovalent" when used in reference to a vaccine refers to a vaccine which is capable of provoking an immune response in a host animal directed against a single type of antigen. In contrast, a "multivalent" vaccine provokes an immune response in a host animal directed against several (i.e., more than one) toxins and/or enzymes associated with disease (e.g., glycoprotease and/or neuraminidase). It is not intended that the vaccine be limited to any particular organism or immunogen.

The present invention further contemplates immunization with or without adjuvant. As used herein, the term "adjuvant" is defined as a substance known to increase the immune response to other antigens when administered with other antigens. If adjuvant is used, it is not intended that the present invention be limited to any particular type of adjuvant—or that the same adjuvant, once used, be used all the time. It is contemplated that adjuvants may be used either separately or in combination. The present invention contemplates all types of adjuvant, including but not limited to agar beads, aluminum hydroxide or phosphate (alum), Incomplete Freund's Adjuvant, as well as Quil A adjuvant commercially available from Accurate Chemical and Scientific Corporation, Gerbu adjuvant also commercially available (GmDP; C.C. Biotech Corp.), and bacterin (i.e., killed preparations of bacterial cells). It is further contemplated that the vaccine comprise at least one "excipient" (i.e., a pharmaceutically acceptable carrier or substance) suitable for administration to a human or other animal subject. It is intended that the term "excipient" encompass liquids, as well as solids, and colloidal suspensions.

As used herein the term "immunogenically-effective amount" refers to that amount of an immunogen required to invoke the production of protective levels of antibodies in a host upon vaccination.

The term "protective level," when used in reference to the level of antibodies induced upon immunization of the host with an immunogen means a level of circulating antibodies sufficient to protect the host from challenge with a lethal dose of the organism or other antigenic material (e.g., toxins, etc.).

A "B cell epitope" generally refers to the site on an antigen to which a specific antibody molecule binds. The identification of epitopes which are able to elicit an antibody response is readily accomplished using techniques well known in the art (See e.g., Geysen et al. *Proc. Natl. Acad. Sci. USA* 81:3998–4002 [1984], for general method of rapidly synthesizing peptides to determine the location of immunogenic epitopes in a given antigen; U.S. Pat. No. 4,708,871 for procedures for identifying and chemically synthesizing epitopes of antigens; and Geysen et al., *Mol. Immunol.*, 23:709–715 [1986] for a technique for identifying peptides with high affinity for a given antibody).

A "T cell epitope" refers generally to those features of a peptide structure capable of inducing a T cell response. In this regard, it is accepted in the art that T cell epitopes comprise linear peptide determinants that assume extended conformations within the peptide-binding cleft of MHC molecules, (See, Unanue et al., *Science* 236:551–557 [1987]). As used here, a T cell epitope is generally a peptide having about 3–5, preferably 5–10 or more, amino acid residues.

The term "self antigen" or "autoantigen," means an antigen or a molecule capable of being recognized during an immune response as self (i.e., an antigen that is normally part of the individual). This is in contrast to antigens which are foreign, or exogenous, and are thus not normally part of the individual's antigenic makeup.

As used herein, the term "autoimmune disease" means a set of sustained organ-specific or systemic clinical symptoms and signs associated with altered immune homeostasis that is manifested by qualitative and/or quantitative defects of expressed autoimmune repertoires. Autoimmune diseases are characterized by antibody or cytotoxic immune responses to epitopes on self antigens found in the diseased individual. The immune system of the individual then activates an inflammatory cascade aimed at cells and tissues presenting those specific self antigens. The destruction of the antigen, tissue, cell type, or organ attacked by the individual's own immune system gives rise to the symptoms of the disease. Clinically significant autoimmune diseases include, for example, rheumatoid arthritis, multiple sclerosis, juvenile-onset diabetes, systemic lupus erythematosus (SLE), autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, and autoimmune thrombocytopenic purpura.

Another aspect of cellular immunity involves an antigen-specific response by helper T lymphocytes ($T_H$ cells). $T_H$ cells act to help stimulate the function, and focus the activity of, nonspecific effector cells against cells displaying peptide antigens in association with MHC molecules on their surface. In addition, various subsets of $T_H$ cells produce distinct cytokines in response to antigenic stimulation. Particularly, antigenic stimulation of naive $T_H$ cells leads to differentiation of the lymphocyte cells into subsets termed "$T_H1$" and "$T_H2$" which have relatively restricted cytokine production profiles and effector functions. $T_H1$ cells secrete IL-2 and IFN-γ, and are the principal effectors of cell-mediated immunity against intracellular microbes and of delayed type hypersensitivity (DTH) reactions. Antibody isotypes stimulated by $T_H1$ cells are effective at activating complement and opsonizing antigens for phagocytosis. $T_H2$ cells produce IL-4 (which stimulates IgE antibody production), IL-5 (eosinophil-activating factor), and IL-10 and IL-13 (which suppress cell-mediated immunity). Thus, the nature of an immune response can be characterized by the profile of antigen-specific lymphocytes that are stimulated by the immunogen, and can be referred to as a "$T_H1$-like" or a "$T_H2$-like" immune response.

The ability of a particular antigen to stimulate a cell-mediated immunological response may be determined by a number of assays, such as by lymphoproliferation (lymphocyte activation) assays, CTL cytotoxic cell assays such as chromium-release assays, or by assaying for T lymphocytes specific for the antigen in a sensitized subject. Such assays are well known in the art (See e.g., Erickson et al., *J Immunol.*, 151:4189–4199 [1993], and Doe et al., *Eur. J Immunol.*, 24:2369–2376 [1994]).

The term "sample" in the present specification and claims is used in its broadest sense. On the one hand it is meant to include a specimen or culture (e.g., microbiological cultures). On the other hand, it is meant to include both biological and environmental samples.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water, and industrial samples, as well as samples obtained from food and dairy processing instruments, apparatus, equipment, utensils, disposable, and non-disposable items. These examples are not to be construed as limiting the sample types applicable to the present invention.

DETAILED DESCRIPTION OF THE INVENTION

In one embodiment, the present invention relates to Zic related genes. In particular, three Zic related genes, Zic1, , Zic2, and Zic3 are provided, identified, and compared with respect to their expression patterns and effects of overexpression. The expression patterns of Xenopus Zic1, Zic2, and Zic3 were found to be distinct, although all three genes expressed in the prospective neural plate region in gastrula. Zic1 and Zic2 were functionally related to Zic3 in that these genes induce neural and neural crest tissues when overexpressed.

Xenopus Zic1 and Zic2 were also found to be very similar to mouse Zic1 and Zic2 in the protein coding region including the zinc finger domain. In early gastrula, Zic1 expression was restricted to the prospective neural plate region whereas Zic2 was expressed widely in the ectoderm. Enhanced neural and neural crest-derived tissue formation were observed in Zic1 or Zic2 overexpressed embryos, as well as in the neural and neural crest marker induction in Zic1 or Zic2 overexpressed animal cap explants. These findings suggest that Zic1 and Zic2 have essentially the same properties as Zic3, and that the Xenopus Zic family act cooperatively in the initial phase of neural and neural crest development.

The Detailed Description of the Invention is divided into seven parts: I) Cloning of Neurogenesis Genes; II) Preparation of Recombinant Vectors and Transformants; III) Analysis of Gene Expression; IV) Protein Production; V) Antibodies Against Zic Proteins; VI) Therapeutic Agents and Agents for Gene Therapy for Nervous Diseases; and VII) Isolation and Characterization of Zic1 and Zic2.

I. Cloning of Neurogenesis Genes mRNA can be prepared by conventional methods. For example, tissue or cells are treated with a guanidine reagent, phenol reagent or the like to obtain the total RNA. Subsequently, poly(A+)RNA (mNRA) is obtained therefrom by the affinity column method using oligo dT-cellulose or poly U-Sepharose carried on Sepharose 2B or by the batch method. Further, the resultant poly(A+)RNA may be further fractionated by sucrose gradient centrifugation or the like.

A single-stranded cDNA is synthesized using the thus obtained mRNA as a template, an oligo(dT) primer and a reverse transcriptase. Then, a double-stranded cDNA is synthesized from the resultant single-stranded cDNA. The resultant double-stranded cDNA is integrated into an appropriate cloning vector to prepare a recombinant vector. A cDNA library can be obtained by transforming *Escherichia coli* or the like with the resultant recombinant vector and selecting the transformant using tetracycline or ampicillin resistance as an indicator.

The transformation of *E. coli* can be performed by the method of Hanahan (Hanahan, J. Mol. Biol. 166: 557–580 [1983]) or the like. Briefly, a method in which a recombinant vector is added to competent cells prepared under the co-existence of calcium chloride, magnesium chloride or rubidium chloride may be used. When a plasmid is used as a vector, the plasmid should contain a drug resistance gene such as tetracycline or ampicillin resistance. Alternatively, a cloning vector other than plasmids (e.g. a phage or the like) may be used.

As a screening method to select clones containing the DNA of interest from the resultant transformants, a method may be given, for example, in which a sense primer and an anti-sense primer corresponding to the amino acid sequence of the zinc finger motif of the mouse Zic gene family are synthesized and a polymerase chain reaction (PCR) is performed using these primers.

As a template DNA to be used in the above PCR, a cDNA which is synthesized from the above-described mRNA by reverse transcription may be given. As primers, 5'-GAGAACCTCAAGATCCACAA-3' (SEQ ID NO: 5) synthesized based on Glu Asn Leu Lys Ile His Lys (SEQ ID NO: 3) may be used for the sense strand; and 5'-TT(C/T)CCATG(A/G)ACCTTCATGTG-3' (SEQ ID NO: 6) synthesized based on His Met Lys Val His Glu Glu (SEQ ID NO: 4) may be used for the anti-sense strand, for example. However, the present invention is not limited to the use of these primers.

The amplified DNA fragment obtained by the above procedures is labelled with $^{32}P$, $^{35}S$, biotin or the like, to obtain a probe. This probe is hybridized to a nitrocellulose filter on which the DNA of the transformant is denatured and fixed. Then, screening can be performed by searching for positive clones.

For the resultant clone, the nucleotide sequence is determined. This sequencing is performed by conventional methods such as the chemical modification method of Maxam-Gilbert or the dideoxynucleotide chain termination method using M13 phage. In preferred embodiments, the sequencing is carried out with an automated DNA sequencer (e.g., PerkinElmer Model 373A DNA Sequencer).

SEQ ID NO: 1 illustrates by example of a nucleotide sequence for the Zic3 gene of the present invention, and SEQ ID NO: 2 illustrates by example an amino acid sequence for the associated protein. The present invention contemplates variation of this amino acid sequence. Proteins find use with the present invention as long as the protein has neurogenesis inducing activity, and in particular early neurogenesis inducing activity. Thus, the amino acid sequence may have one or more mutations, such as deletions, substitutions, or additions, of at least one amino acid.

For example, at least 1 amino acid, preferably 1 to about 10 amino acids, more preferably 1 to 5 amino acids may be deleted in the amino acid sequence shown in SEQ ID NO:2; or at least 1 amino acid, preferably 1 to about 10 amino acids, more preferably 1 to 5 amino acids may be added to the amino acid sequence shown in SEQ ID NO:2; or at least 1 amino acid, preferably 1 to about 10, amino acids, more preferably 1 to 5 amino acids may be substituted with other amino acid(s) in the amino acid sequence shown in SEQ ID NO:2.

Accordingly, a gene coding for a polypeptide having the amino acid sequence into which the above-mentioned mutation has been introduced is included in the gene of the invention as long as it has neurogenesis inducing activity (e.g., early neurogenesis inducing activity). Also, a DNA which can hybridize with the gene described above under stringent conditions is provided by the present invention. For example, in some embodiments of the present invention, stringent conditions refers to those conditions in which sodium concentration is 600–900 mM and temperature is 60–68° C., preferably 65° C.

The introduction of a mutation into a gene may be performed by conventional methods such as the method of Kunkel, the gaped duplex method, or variations thereof using a mutation introducing kit (e.g., Mutant-K [Takara] or Mutant-G [Takara]) utilizing site-specific mutagenesis or using a LA PCR in vitro Mutagenesis Series Kit manufactured by Takara, or the like.

Once the nucleotide sequence of the gene of the invention has been determined definitely, the gene of the invention may be obtained by chemical synthesis, by PCR using the cDNA or genomic DNA of the gene of the invention as a template, or by hybridization of a DNA fragment having the above nucleotide sequence as a probe.

II. Preparation of a Recombinant Vector and a Transformant

A. Preparation of a Recombinant Vector

The recombinant vector of the invention may be obtained by ligating (i.e., inserting) the gene of the invention to an appropriate vector. The vector into which the gene of the invention is to be inserted is not particularly limited as long as it is replicable in a desired host. For example, plasmid DNA, phage DNA or the like may be used.

Specific examples of plasmid DNA include *E. coli*-derived plasmids (e.g., pBR322, pBR325, pUC118, pUC119, etc.), *Bacillus subtilis*-derived plasmids (e.g., pUB110, pTP5, etc.) and yeast-derived plasmids (e.g., YEp13, YEp24, YCp50, etc.). Specific examples of phage DNA include λ phage and the like. Further, an animal virus vector such as retrovirus or vaccinia virus; or an insect virus vector such as baculovirus may also be used.

For insertion of the gene of the invention into a vector, a method may be employed in which the purified DNA is digested with an appropriate restriction enzyme and then inserted into the restriction site or the multi-cloning site of an appropriate vector DNA for ligation to the vector.

The gene of the invention should be operably linked to the vector. For this purpose, the vector of the invention may contain, if desired, cis elements such as an enhancer, splicing signal, poly(A) addition signal, selection marker, ribosome binding sequence (SD sequence) or the like in addition to a promoter and the gene of the invention. As the selection marker, dihydrofolate reductase gene, ampicillin resistance gene, neomycin resistance gene, or the like may be used.

B. Preparation of a Transformant

In some embodiments of the present invention, the transformant is obtained by introducing the recombinant vector of the invention into a host so that the gene of interest is expressed. The host is not particularly limited as long as it can express the DNA of the invention. Specific examples of the host include Escherichia bacteria such as *E. coli;* Bacillus bacteria such as *Bacillus subtilis;* Pseudomonas bacteria such as *Pseudomonas putida;* Rhizobium bacteria such as *Rhizobium meliloti;* yeasts such as *Saccharomyces cerevisiae, Schizosaccharomyces pombe;* animal cells such as COS cells, CHO cells; or insect cells such as Sf9 and Sf21 cells.

When a bacterium such as *E. coli* is used as the host, the recombinant vector of the invention is capable of autonomous replication in the host and, at the same time, it is constituted preferably by a promoter, a ribosome binding sequence, the gene of the invention and a transcription termination sequence. The vector may also contain a gene to control the promoter.

Examples of *E. coli* that find use with the present invention include, but are not limited to, K12 or DH1 strains. Examples of *Bacillus subtilis* that find use with the present invention include, but are not limited to, MI 114 or 207-21 strains.

As the promoter, any promoter may be used as long as it can direct the expression of the gene of interest in a host such as *E. coli*. For example, an *E. coli*- or phage-derived promoter such as trp promoter, lac promoter, $P_L$ promoter or $P_R$ promoter may be used. An artificially designed and altered promoter such as tac promoter may also be used.

As a method for introducing the recombinant vector into a bacterium, any method of DNA introduction into bacteria may be used. For example, a method using calcium ions (Cohen et al., Proc. Natl. Acad. Sci., USA, 69: 2110–2114 [1972]) electroporation, or the like may be used.

In some embodiments of the present invention, when a yeast is used as the host, *Saccharomyces cerevisiae, Schizosaccharomyces pombe, Pichia pastoris* or the like is used. In this case, the promoter to be used is not particularly limited. Any promoter may be used as long as it can direct the expression of the gene of interest in yeast. For example, gal1 promoter, gal10 promoter, heat shock protein promoter, MF α1 promoter, PH05 promoter, PGK promoter, GAP promoter, ADH promoter, AOX1 promoter or the like may be used.

As a method for introducing the recombinant vector into the yeast, any method of DNA introduction into yeasts may be used. For example, electroporation (Becker et al, Methods Enzymol., 194: 182–187 [1990]), the spheroplast method (Hinnen et al, Proc. Natl. Acad. Sci., USA, 75: 1929–1933 [1978]), the lithium acetate method (Itoh, Bacteriol., 153: 163168 [19893]) or the like may be used.

When an animal cell is used as the host, simian COS-7 or Vero cells, Chinese hamster ovary cells (CHO cells), mouse L cells, rat GH3 cells, human FL cells or the like may be used, although a variety of other cells find use with the present invention. As a promoter, SRα promoter, SV40 promoter, LTR promoter, CMV promoter or the like may be used. The early gene promoter of human cytomegalovirus may also be used.

As a method for introducing the recombinant vector into the animal cell, electroporation, the calcium phosphate method, lipofection or the like may be used.

When an insect cell is used as the host, Sf9 cells, Sf21 cells or the like may be used. As a method for introducing the recombinant vector into the insect cell, the calcium phosphate method, lipofection, electroporation or the like may be used.

The recombinant vector of the invention incorporated in *E. coli* DH5 (designation: *Escherichia coli* pXenopus Zic3) was deposited at the National Institute of Bioscience and Human Technology, Agency of Industrial Science and Technology (1-3, Higashi 1-Chome, Tsukuba City, Ibaraki Pref., Japan) as FERM BP-6519 under the Budapest Treaty on Mar. 26, 1998.

III. Analysis of Gene Expression

Since the gene of the invention has neurogenesis inducing activity, the expression of this gene can be examined by using embryos of specific developmental stages.

The time of expression of the Zic3 gene of the invention in the embryo can be confirmed by analyzing, for example, expression of the mRNA or the protein in embryos of individual developmental stages. For example, as a method for confirming expression of Zic3 mRNA, RT-PCR, or northern analysis may be used; as a method for confirming expression of ZIC3 protein, western analysis using an antibody against this protein may be used.

Further, the distribution of Zic3 expression in the embryo can be confirmed by analyzing the mRNA by in situ hybridization or the like, or by analyzing the protein by immunohistochemical techniques using an antibody. In situ hybridization can be performed, for example, as described previously (Chitnis et al., Nature 375: 761–766 [1995]) by staining the embryo with digoxigenin or a radioisotope labelled RNA probe.

IV. Protein Production

In some embodiments of the present invention, for example, the protein of the invention is a protein having the amino acid sequence encoded by the Zic3 gene of the invention, or a protein which has the above amino acid sequence having the mutation of at least at 1 amino acid and which has neurogenesis inducing activity. This protein is also called "ZIC3 protein".

ZIC3 protein of the present invention can be obtained by culturing the transformant described above and recovering the protein from the resultant culture. The term "culture" includes any of the following materials: culture supernatant, cultured cells, cultured microorganisms, or crushed cells or microorganisms. The cultivation of the transformant of the invention in a medium is carried out by conventional methods used for culturing a host.

As a medium to culture the transformant obtained from a microorganism host such as *E. coli* or yeast, either a natural or a synthetic medium may be used as long as it contains carbon sources, nitrogen sources and inorganic salts assimilable by the microorganism and is capable of effective cultivation of the transformant. As carbon sources, carbohydrates such as glucose, fructose, sucrose, starch; organic acids such as acetic acid, propionic acid; and alcohols such as ethanol and propanol may be used. As nitrogen sources, ammonia; ammonium salts of inorganic or organic acids such as ammonium chloride, ammonium sulfate, ammonium acetate, ammonium phosphate; other nitrogen-containing compounds; Peptone; meat extract; corn steep liquor and the like may be used. As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

In preferred embodiments, the cultivation is carried out under aerobic conditions (such as shaking culture or aeration agitation culture) at 37° C. for 6 to 24 hrs. During the cultivation, the pH is maintained at 7.0 to 7.5. The pH adjustment is carried out using an inorganic or organic salt, an alkali solution or the like. During the cultivation, an antibiotic such as ampicillin or tetracycline may be added to the medium if necessary.

When a microorganism transformed with an expression vector using an inducible promoter is cultured, an inducer may be added to the medium if necessary. For example, when a microorganism transformed with an expression vector using Lac promoter is cultured, isopropyl-O-D-thiogalactopyranoside (IPTG) or the like may be added. When a microorganism transformed with an expression vector using trp promoter is cultured, indoleacetic acid (IAA) or the like may be added.

As a medium to culture a transformant obtained from an animal cell as a host, commonly used RPMI 1640 medium or DMEM medium, or one of these media supplemented with fetal bovine serum, etc. may be used. Usually, the cultivation is carried out in the presence 5% $CO_2$ at 37° C. for 1 to 30 days. During the cultivation, an antibiotic such as kanamycin or penicillin may be added to the medium if necessary.

After the cultivation, ZIC3 protein of the invention is extracted by disrupting the microorganisms or cells if the protein is produced in the microorganisms or cells. If ZIC3 protein of the invention is produced outside of the microorganisms or cells, the culture fluid is used directly or is subjected to centrifugation to remove the microorganisms or cells. Thereafter, the resultant supernatant is subjected to conventional biochemical techniques used for isolating/purifying a protein. These techniques include ammonium sulfate precipitation, gel chromatography, ion exchange chromatography, and affinity chromatography. These techniques may be used independently or in an appropriate combination to thereby isolate and purify ZIC3 protein of the invention from the above culture.

V. Antibody Against Zic Proteins

In the present invention, antibody against ZIC proteins of the invention can also be prepared. The term "antibody" means an antibody molecule as a whole which can bind to the peptide of the invention that is an antigen, or a fragment thereof (e.g., Fab or F(ab')$_2$ fragment). The antibody may be either polyclonal or monoclonal.

The antibody of the invention may be prepared by various methods. Such methods of antibody preparation are well known in the art (See e.g., Sambrook, J. et al., Molecular Cloning, Cold Spring Harbor Laboratory Press [1989]).

A. Preparation of a Polyclonal Antibody against the Protein of the Invention

The following description is provided for the ZIC3 protein and is applicable to other ZIC proteins. In some embodiments of the present invention, ZIC3 protein of the invention is genetically engineered as described above or a fragment thereof is administered as an antigen to a mammal such as rat, mouse or rabbit. The dosage of the antigen administered per animal is 0.1 to 10 mg when no adjuvant is used, and 1 to 100 µg when an adjuvant is used. As an adjuvant, Freund's complete adjuvant (FCA), Freund's incomplete adjuvant (FIA), aluminium hydroxide adjuvant or the like may be used. Immunization is performed mainly by intravenous, subcutaneous or intraperitoneal injection. The interval of immunization is not particularly limited. In preferred embodiments, immunization is carried out one to 10 times, preferably 2 to 5 times, at intervals of several days to several weeks, preferably at intervals of 2 to 5 weeks. Subsequently, 6 to 60 days after the final immunization, antibody titer is determined by, preferably, enzyme immunoassay (EIA), radioimmunoassay (RIA) or the like. Blood is collected from the animal, on the day when the maximum antibody titer is shown, to thereby obtain antiserum. When purification of an antibody from the antiserum is necessary, the antibody is purified by appropriately selecting a conventional method such as ammonium sulfate salting out, ion exchange chromatography, gel filtration, affinity chromatography, or using these methods in combination.

B. Monoclonal Antibodies (i) Recovery of Antibody-Producing Cells

In some embodiments of the present invention, ZIC3 protein of the invention genetically engineered as described above or a fragment thereof is administered as an antigen to a mammal such as rat, mouse or rabbit. The dosage of the antigen administered per animal is, for example, 0.1 to 10 mg when no adjuvant is used, and 1 to 100 $\mu$g when an adjuvant is used. As an adjuvant, Freund's complete adjuvant (FCA), Freund's incomplete adjuvant (FIA), aluminium hydroxide adjuvant or the like may be used. Immunization is performed mainly by intravenous, subcutaneous or intraperitoneal injection. The interval of immunization is not particularly limited. In preferred embodiments, immunization is carried out one to 10 times, preferably 2 to 5 times, at intervals of several days to several weeks, preferably at intervals of 2 to 5 weeks. Subsequently, 1 to 10 days, preferably 3 days after the final immunization, antibody-producing cells are collected. As antibody-producing cells, spleen cells, lymph node cells, peripheral blood cells, etc. may be enumerated. Among them, spleen cells and local lymph node cells are preferable.

(ii) Cell Fusion

In order to obtain hybridomas, cell fusion between antibody-producing cells and myeloma cells is performed. As the myeloma cells to be fused to the antibody-producing cells, a commonly available cell strain of an animal such as mouse may be used. Preferably, a cell strain to be used for this purpose is one which has drug selectivity, cannot survive in HAT selective medium (i.e., containing hypoxanthine, aminopterin and thymidine) when unfused, and can survive there only when fused to antibody-producing cells. As myeloma cells, mouse myeloma cell strains including, but not limited to, P3X63Ag.8.U1(P3U1), Sp2/0, NS-1 may be used.

Subsequently, the myeloma cells and the antibody-producing cells described above are subjected to cell fusion. Briefly, $1\times10^9$ cells/ml of the antibody-producing cells and $1\times10^8$ cells/ml of the myeloma cells are mixed together in equal volumes in an animal cell culture medium such as serum-free DMEM or RPMI-1640, and reacted in the presence of a cell fusion promoting agent. In some embodiments, as the cell fusion promoting agent, polyethylene glycol with an average molecular weight of 1,500 Da may be used. Alternatively, the antibody-producing cells and the myeloma cells may be fused in a commercial cell fusion apparatus utilizing electric stimulation (e.g., electroporation).

(iii) Selection and Cloning of a Hybridoma

A hybridoma of interest is selected from the cells after the cell fusion. As a method for this selection, the resultant cell suspension is appropriately diluted with fetal bovine serum-containing RPMI-1640 medium or the like and then plated on microtiter plates at a density of about $2\times10^5$ cells/well. A selective medium is added to each well. Then, the cells are cultured while appropriately exchanging the selective medium. As a result, about 14 days after the start of cultivation in the selective medium, the growing cells are obtained as hybridomas.

Subsequently, screening is performed as to whether the antibody of interest is present in the culture supernatant of the grown hybridomas. The screening of hybridomas may be performed by any of conventional methods. For example, a part of the culture supernatant of a well in which a hybridoma is grown is collected and subjected to enzyme immunoassay or radioimmunoassay.

Cloning of the fused cell is performed by the limiting dilution method or the like. Finally, the hybridoma of interest which is a monoclonal antibody-producing cell is established.

(iv) Recovery of the Monoclonal Antibody

In some embodiments of the present invention, a method for recovering the monoclonal antibody from the thus established hybridoma such as conventional cell culture methods or the abdominal dropsy formation method may be employed.

In the cell culture method, the hybridoma is cultured in an animal cell culture medium such as 10% fetal bovine serum-containing RPMI-1640 medium, MEM medium or a serum-free medium under conventional culture conditions (e.g., at 37° C. under 5% $CO_2$) for 2 to 10 days. Then, the monoclonal antibody is recovered from the culture supernatant.

In the abdominal dropsy formation method, about $1\times10^7$ cells of the hybridoma is administered into the abdominal cavity of an animal syngeneic to the mammal from which the myeloma cells were derived, to thereby propagate the hybridoma greatly. One to two weeks thereafter, the abdominal dropsy or serum is collected.

In the above-mentioned method of recovery of the antibody, if purification of the antibody is necessary, the antibody can be purified by appropriately selecting a conventional method such as ammonium sulfate salting out, ion exchange chromatography, gel filtration, affinity chromatography, or using these methods in combination.

Once the polyclonal or monoclonal antibody is thus obtained, in some embodiments of the present invention, the antibody is bound to a solid carrier as a ligand to thereby prepare an affinity chromatography column. With this column, the peptides of the present invention can be purified from the above mentioned source or other sources. These antibodies further find use in Western blotting to detect the proteins of the present invention.

VI. Therapeutic Agents and Agents for Gene Therapy for Nervous Diseases

Since the proteins and the genes of the present invention have neurogenesis inducing activity, they are useful as a therapeutic agents and as agents for gene therapy, respectively, for nervous diseases. In some embodiments of the present invention, the therapeutic agents or the agents for gene therapy of the present invention is administered to a subject orally or parenterally and systemically or locally.

When the protein or the gene of the present invention is used as a therapeutic agent or an agent for gene therapy for nervous diseases, the disease to be treated is not particularly limited. For example, the proteins or the genes may be used, alone or in combination, for diseases including, but not limited to, Alzheimer's disease, amyotrophic lateral sclerosis, spinocerebellar degeneration, Parkinson's disease, cerebral ischemia or the like for the specific purpose of treatment or prevention. These diseases may be in the form of a single disease or may be complicated by one of these diseases or by some disease other than those mentioned above. Any of such forms may be treated with the proteins or the genes of the invention.

In preferred embodiments of the present invention, when the therapeutic agent of the invention is administered orally, the agent may be formulated into a tablet, capsule, granule, powder, pill, troche, internal liquid agent, suspension, emulsion, syrup or the like. Alternatively, the therapeutic agent may be prepared into a dry product which is re-dissolved just before use. In preferred embodiments, when the therapeutic agent of the invention is administered parenterally, the agent may be formulated into a intravenous injection (including drops), intramuscular injection, intraperitoneal injection, subcutaneous injection, suppository, or the like. Injections are supplied in the form of unit dosage ampules or multidosage containers. These formulations may be prepared by conventional methods using appropriate excipients, fillers, binders, wetting agents, disintegrating agents, lubricating agents, surfactants, dispersants, buffers, preservatives, dissolution aids, antiseptics, flavoring/ perfuming agents, analgesics, stabilizers, isotonicity inducing agents, etc. conventionally used in pharmaceutical preparations.

Each of the above-described formulations may contain pharmaceutically acceptable carriers or additives. Specific examples of such carriers or additives include water, pharmaceutically acceptable organic solvents, collagen, polyvinyl alcohol, polyvinylpyrrolidone, carboxyvinyl polymers, sodium alginate, water-soluble dextran, sodium carboxymethyl amylose, pectin, xanthan gum, gum arabic, casein, gelatin, agar, glycerol, propylene glycol, polyethylene glycol, vaseline, paraffin, stearyl alcohol, stearic acid, human serum albumin, mannitol, sorbitol and lactose. One or a plurality of these additives are selected or combined appropriately depending of the form of the preparation.

The dosage levels of the therapeutic agent of the invention will vary depending on the age of the subject, the route of administration and the number of times of administration and may be varied in a wide range. When an effective amount of the protein of the invention is administered in combination with an appropriate diluent and a pharmaceutically acceptable carrier, the effective amount of the protein can be in the range from 0.01 to 1000 mg/kg per administration, although other amounts are contemplated, where appropriate. One skilled in the art is capable of determining the therapeutically effective amount appropriate any given circumstances. In some embodiments, the therapeutic agent is administered once a day or in several dosages per day for at least one day.

In some embodiments of the present invention, when the gene of the invention is used as an agent for gene therapy for nervous diseases, the gene of the invention may be directly administered by injection. Alternatively, a vector incorporating the gene of the invention may be administered. Specific examples of a suitable vector for this purpose include an adenovirus vector, adeno-associated virus vector, herpes virus vector, vaccinia virus vector and retrovirus vector. The gene of the invention can be administered efficiently by using such a virus vector. Alternatively, the gene of the invention may be enclosed in phospholipid vesicles such as liposomes, and the resultant liposomes may be administered to the subject. Briefly, since liposomes are biodegradable material-containing closed vesicles, the gene of the invention is retained in the internal aqueous layer and the lipid bilayer of liposomes by mixing the gene with the liposomes (i.e., a liposome-gene complex). Subsequently, when this complex is cultured with cells, the gene in the complex is taken into the cells (i.e., lipofection). Then, the resultant cells may be administered by the methods described below.

In some embodiments of the present invention, as a method for administering the agent for gene therapy of the invention, local administration to tissues of the central nervous system (brain, spiral cord) may be performed in addition to conventional systemic administration such as intravenous or intra-arterial administration. Further, an administration method combined with catheter techniques and surgical operations may also be employed.

The dosage levels of the agent for gene therapy of the invention vary depending on the age, sex and conditions of the subject, the route of administration, the number of times of administration, and the type of the formulation, among other considerations. One skilled in the art is capable of determining the therapeutically effective amount appropriate any given circumstances. Usually, it is appropriate to administer the gene of the invention in an amount of 0.1–100 mg/adult body/day, although other concentrations are contemplated, where appropriate.

According to the present invention, there are provided neurogenesis inducing proteins; a neurogenesis inducing genes (e.g., Zic1, Zic2, and/or Zic3) coding for the proteins; recombinant vectors comprising the genes; transformants comprising the vectors; antibodies against the above proteins; and therapeutic agents for nervous diseases. The Zic genes of the invention find use as a diagnostic agents for nervous diseases, as therapeutic agents for Alzheimer's disease and the like, and as probes to detect nervous diseases, among other applications.

VII. Isolation and Characterization of Zic1 and Zic2

A. Isolation of Xenopus Zic 1 and Zic2

To isolate additional Zic related genes in Xenopus, the Xenopus neurula cDNA library was further screened with the cDNA fragments generated by PCR. Two novel Xenopus Zic-related genes were identified (FIGS. 8A, B). A comparison of their predicted amino acid sequences to those of Xenopus Zic3, mouse Zic1, Zic2, Zic3, Zic4 and Drosophila Opa (Nakata et al., supra; Aruga et al., J. Neurochem. 63: 1880–1890 [1994]; Aruga et al., J. Biol. Chem. 271: 1043–1047 [1996]; Aruga et al., Gene 172: 291–294 [1996], supra; Benedyk et al., supra) revealed that one was the most similar to mouse Zic1, and the other was similar to Zic2. Therefore these genes were designated Xenopus Zic1 (SEQ ID NO: 41) and Zic2 (SEQ ID NO: 43). Although significant homology was found in the entire protein coding region, the most extensive homology was found in the zinc finger domains (98% between Xenopus Zic1 [SEQ ID NO: 42] and mouse Zic1, 97% between Xenopus Zic2 [SEQ ID NO: 44] and mouse Zic2) (FIG. IC). In addition, these novel genes showed significant similarity to Drosophila pair-rule gene, odd-paired (opa).

The zinc finger region, particularly from the 3rd to the 5th zinc finger motif is highly similar to those of the Gli-Ci zinc finger proteins (Ruiz i Altaba, "Catching a Gli-mpse of Hedgehog," Cell 90: 193–196 [1997]), which mediate the hedgehog signal. A crystallographic analysis of Gli protein indicated that the same region actually interacts with the DNA (Pavletich and Pabo, Pavletich, "Crystal structure of a five-finger GLI-DNA complex: new perspectives on zince fingers," Science 261, 1701–1707 [1993]). Taken together with previous data indicating that mouse Zic1 can bind to the Gli-binding sequence (Aruga et al., J. Neurochem. 63: 1880–1890 [1994]), the current evidence suggests that the two protein families, Gli-Ci and Zic-Opa, can bind to highly similar target sequences, although an understanding of the mechanism is not necessary to practice the present invention and the present invention is not limited to any particular mechanism.

In addition to the zinc finger domain, it is noted that there were short domains which are conserved in the Xenopus Zic, mouse Zic and Drosophila opa genes. In particular, an amino acid sequence motif, FNSTRDFRXR (SEQ ID NO: 49), which was found in the N-terminal region, was highly conserved (FIG. 8D).

B. Temporal Expression Profiles of Zic1 and Zic2 During Xenopus Development

Figure 9:
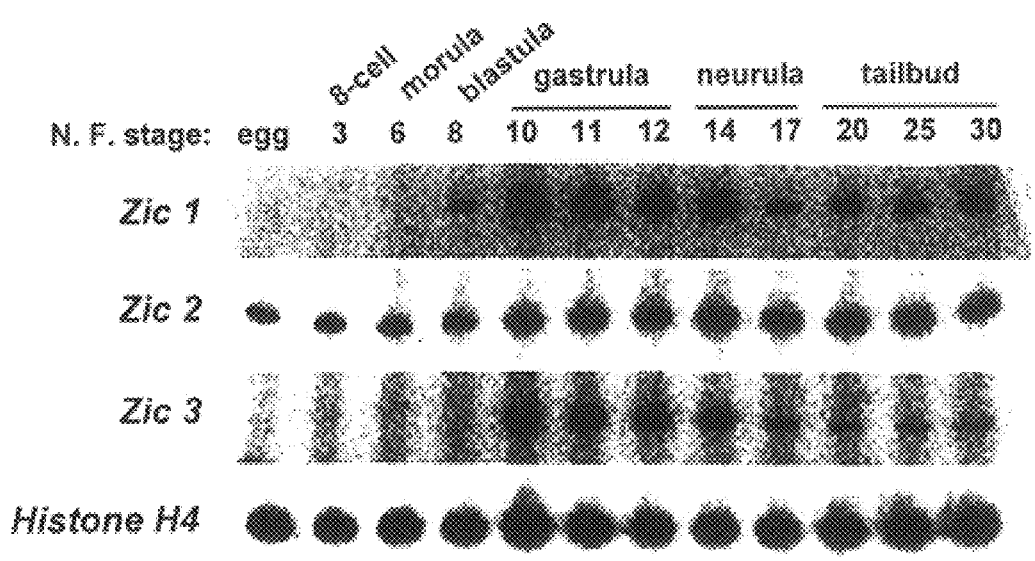
FIG. 9 shows the temporal expression profiles of Xenopus Zic1, Zic2 and Zic3 during Xenopus development. RNA was extracted from embryos at the indicated stage of development and Zic1, Zic2, and Zic3 mRNA expression levels were measured by RT-PCR. The ubiquitous marker Histone H4 served as a control.

RT-PCR analyses was performed to compare the temporal expression patterns of the Xenopus Zic genes (FIG. 9). Zic2 was maternally expressed, in contrast to Zic3, which was detected from late blastula but not at earlier stages (Nakata et. al., 1997). Zic1 mRNA was detected from the blastula stage (stage 8) and was peaked in the gastrula. The expression profile is similar to that of Zic3. Zic2 was continuously expressed from the egg to the tailbud stage (stage 30) with an increase in expression at the early gastrula stage (stage 10).

C. Spatial Expression Patterns of Zic1 and Zic2 During Xenopus Embryogenesis

Figure 10:
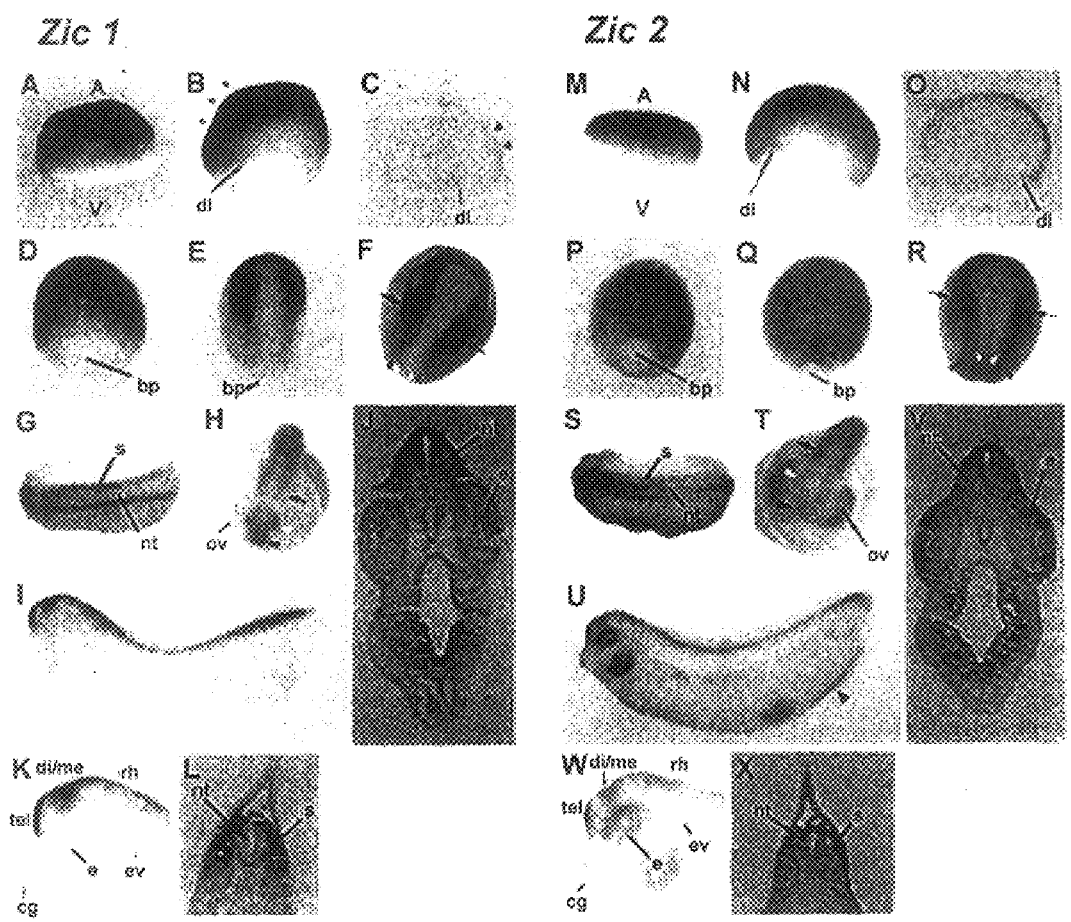
FIG. 10 panels A–X show the spatial expression patterns of Zic1 and Zic2 in Xenopus embryos. Series of embryos were hybridized with digoxigenin-labeled antisense Zic1 (A–L) and Zic2 (M–X) RNA (A, m) blastula stage (stage 9). In the blastula stage, Zic1 and Zic2 were expressed throughout the ectoderm (A, animal side; V, vegetal side) (B,C,N,O) mid-gastrula stage (stage 10.5). (C) The expression of Zic1 in the prospective neural plate was confirmed in a cross-section of the same embryo as in B (arrowhead). However, Zic2 was expressed in a broader region of the ectoderm (N,O). (D,P) Stage 11–12 (E,Q) Stage 12.5–13.5 (F,R) Stage 14–15. White and black arrowheads indicate the lateral edge of the neural plate and the neural crest, respectively. Arrows indicate the neural plate border region of the prospective rhombencephalon (G,H,S,T) Stage 20. The black arrowhead, white arrowhead and arrow indicate the telencephalon, diencephalon and mesencephalon, respectively. (I–L,U–X) Stage 30. Transverse section through the head (J,V) and trunk region (L,X) of the same embryo as in (I,U). (K,W) magnified views in the head legion of I and U. (A,M,I,U) are lateral views. The upper side of the panel is the animal side in (A,M). (B,N) Dorsal-vegetal views, (D–G,P–S) Dorsal views. (D–F,P–R) anterior side is upper side. (G,S) The anterior side is toward the left. (H.T) Anterior views of (G,S). The upper side is dorsal (dl), dorsal lip; blastopore (bp); somite (s.); neural tube (nt); optic vesicle (ov); telencephalon (tel); diencephalon and midbrain boundary (di/mi); rhombencephalon (rh); eye (e); ear vesicle (ev); cement gland (cg).

To determine the spatial expression patterns of Xenopus Zic1 and Zic2, whole mount in situ hybridization was performed. At the blastula stage (stage 9), Zic1 and Zic2 were expressed throughout the ectoderm (FIGS. 10 A, M). At the gastrula stage (stage 10.5), Zic1 expression became restricted to the prospective neural plate, as observed for the Zic3 expression (FIGS. 10 B, C; arrowhead, Nakata et.al., supra), whereas Zic2 was expressed throughout the ectoderm in the gastrula (FIGS. 10 N, O).

During the late gastrula to neurula stages, both Zic1 and Zic2 expression gradually diminished in the midline region of the neural plate and increased in the anterior neural folds (FIGS. 10 D–F, P–R). However, Zic2 continued to be expressed in the posterior medial part of the neural plate (FIG. 10 Q, arrowhead). At the neurula stage, staining was seen as four longitudinal lines in the trunk, similar to that of Zic3 (FIGS. 10 F, R, white and black arrowheads, Nakata, et. al., supra).

In the early tailbud stages (stages 22–23, FIGS. 10 G, H, S, T), Zic1 and Zic2 were expressed in the dorsal forebrain, midbrain, and hindbrain (FIGS. 10 H, T). Subsequently, expression was seen in the telencephalon and diencephalon/mesencephalon boundary (stage 30; FIGS. 10 K, W). In the spinal cord, expression was restricted to the dorsal most region including the roof plate (FIGS. 10 J, L, V, X). These expression patterns in the central nervous system are essentially the same as Zic3 except for a slight difference in the expression level along the anterior to posterior axis (Nakata et. al., supra).

However, the expression patterns of the three Zic genes varied in somites and eye vesicles. Both Zic1 and Zic2 were expressed in the somites. The level of Zic1 expression was higher than that of Zic2, in comparison to the expression in neural tubes (FIGS. 10G, S), and Zic2 expression extended more ventrally than Zic1. (FIGS. 10 L, X). In contrast, Zic3 expression in the somites was negligible (Nakata et. al., supra). As to the expressions in eye vesicles, Zic2 was expressed whereas Zic1 and Zic3 were not (FIGS. 10 H, T, Nakata et. al., supra). Zic2 expression in the eyes was restricted to the Ciliary marginal zone of neural retina, with no expression in the lens (FIG. 10 J, V).

These expression patterns, when compared to that of Zic3, show that each of the three Xenopus Zic genes is involved in several developmental processes including those of the nervous system and somites.

D. Zic1 and Zic2 Induce Neural and Neural Crest Tissues

The effects of the Zic1 or Zic2 overexpression on the embryos was examined. First, MT-Zic1 (Zic1 tagged with myc epitopes) or MT-Zic2 mRNA were injected into both blastomeres of 2-cell stage embryos (FIGS. 11 A–F). Ectopic pigment cells appeared in these embryos (FIGS. 11 C–F). The appearance of ectopic pigment cells was also found in the MT-Zic3 or Zic3 mRNA injected embryos (FIG. 11 B, Nakata et. al., supra). However, the pigment cells induced by MT-Zic1 overexpression were apparently less dense and less frequent than those induced by MT-Zic3 or MT-Zic2 overexpression (FIG. 11) [Ectopic pigment cells were found in 0/10 of MT-Zic1 (100 pg), 16/16 of MT-Zic1 (500 pg), 16/20 of MT-Zic2 (100 pg), 19/19 of MT-Zic2 (500 pg) and 13/13 of MT-Zic3 (100 pg) injected embryos]. Each of the Zic proteins was expressed at equivalent levels in each Zic mRNA injected embryo, suggesting that each Zic protein may have different pigment cell-inducing activities (FIG. 11 I).

Figure 12:
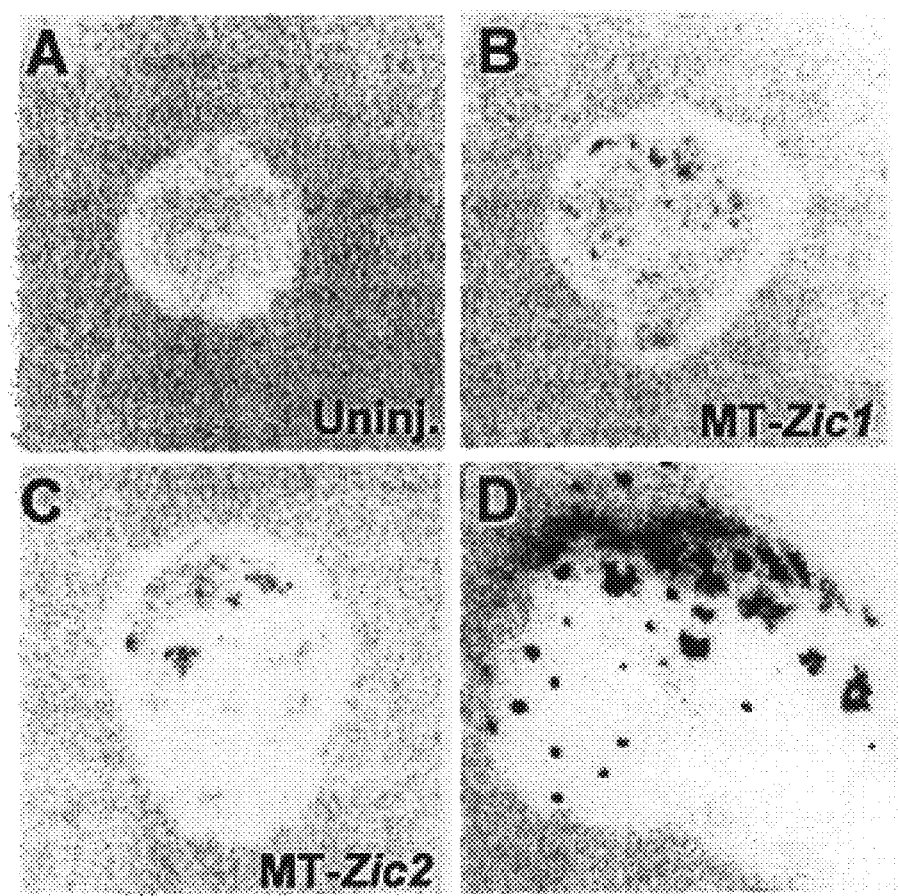
FIG. 12 panels A–D shows the pigment cells expressed by Zic1 or Zic2 overexpression in animal cap explant. (A) Uninjected animal cap explant. A total of 250 pg of MT-Zic1 (B) or a total of 125 pg MT-Zic2 (C) mRNA was injected into two animal blastomeres of 2-cell stage embryos obtained by the mating between albino female and wild type males. Animal caps were explanted at stage 9 and cultured. (D) A magnified view of the abdominal region of the control embryo at the same time as animal cap explant (stage 45). The pigment cells appeared in the MT-Zic1 or MT-zic2 overexpressed animal cap explants are similar to the melanocytes which are derived from neural crest.

Next, MT-Zic1 (250 pg) or MT-Zic2 (125 pg) mRNA were injected into a blastomere of a 2-cell stage embryo and sectioned at stages 35–36. Thickening of the neural tubes and the ectopic presumptive mesenchymal tissue with ectopic pigment cells in the injected side of these embryos was observed (FIGS. 11 G, H). The ectopic pigment cells were also found in animal cap explants overexpressing Mt-Zic1 (8/12), or Mt-Zic2 (11/11) (FIG. 12). To clarify whether these pigment cells were melanocytes derived from neural crest, the animal cap explants derived from the embryos obtained by the mating between albino female and wild type males were used. In this case, the shapes of the pigmented cells appearing in the explants could clearly be observed. As expected, the pigment cells had elaborate processes which were typically found in the melanocytes (FIG. 12). In addition, a neural crest marker twist (Xtwi, Hopwood et. al., "A Xenopus mRNA related to Drosophila twist is expressed in response to induction in the mesoderm and the neural crest," Cell 59, 893–903 [1989]) was expressed in the mesenchymal tissue beneath the ectopic pigment cells in embryos in which Zic1 or Zic2 were overexpressed as observed with Zic3 overexpression (Nakata et. al., supra). These findings suggest that pigment cells expressed in Zic1 or Zic2 injected embryos were derived from neural crest.

Figure 13:
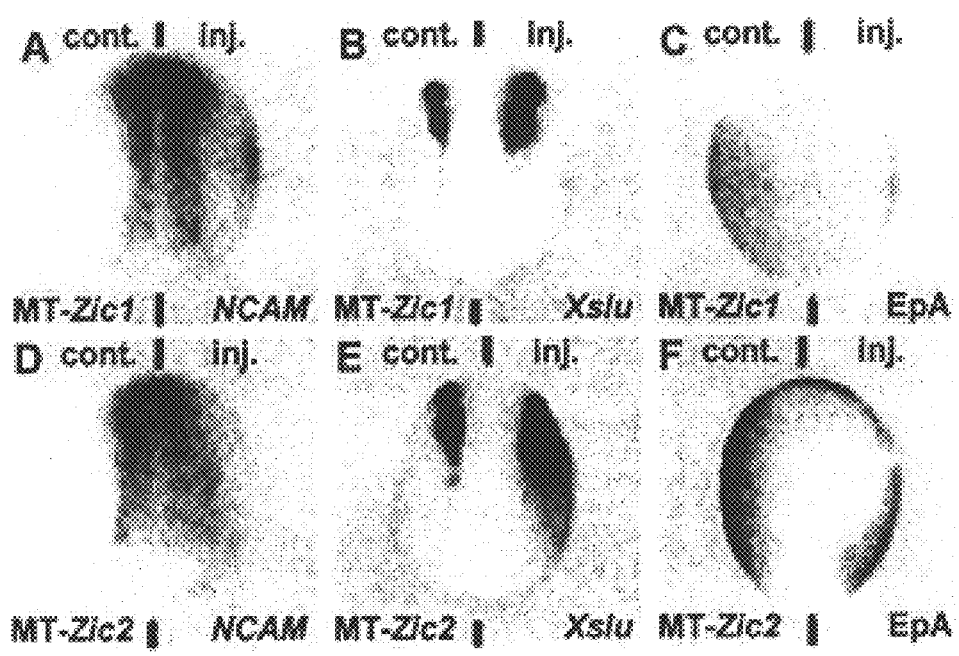
FIG. 13 panels A–P shows that Zic1 and Zic2 induced NCAM and Xslu expression but reduced epidermis in early stage embryos. A total of 250 pg of MT-Zic1 mRNA (A–C) or 125 pg of MT-Zic2 (D–F) was injected into one blastomere of 2-cell stage embryos. In situ hybridization was performed with a pan-neural marker gene (NCAM; A,D), a neural crest marker (Xslu; B,E) probe, and immunohistochemistry was performed with an epidermal marker (EpA) monoclonal antibody (C,F). Dorsal view of a stage 13–14 embryo. NCAM and Xslu expressing regions show lateral expansion of the injected side (A,B,D,E). EpA staining in the epidermis is reduced on the injected side (C,F).

To examine whether Zic1 and Zic2 overexpression results in alterations in cell fate, the expression of a neural marker (NCAM) (Kintner and Melton, "Expression of Xenopus NCAM RNA in ectoderm is an early response to neural induction," Development 99: 311–325 [1987]), a neural crest marker (Xslu) (Mayor et. al., "Induction of the prospective neural crest of Xenopus," Development 121: 767–777 [1995]), and an epidermal antigen (EpA) (Jones and Woodland, "Development of the ectoderm in Xenopus: tissue specification and the role of cell association and division," Cell 44: 345–355 [1986]) were examined at an early neurula stage (stage 14) (FIG. 13). The NCAM-expressing neural plate region increased in the Zic1 or Zic2 mRNA injected side [8/8 of MT-Zic1 (250 pg), 10/14 of MT-Zic2 (125 pg) injected embryos] (FIGS. 13A, D). Xslu expression was also increased in the Zic1 or Zic2 mRNA injected side [6/9 of MT-Zic1 (250 pg), 18/18 of MT-Zic2 (125 pg) injected embryos] (FIGS. 13 B, E). In contrast, the expression of EpA was significantly reduced on the Zic1 or Zic2 mRNA injected side [18/22 of MT-Zic1 (250 pg), 20/24 of MT-Zic2 (125 pg) injected embryos] (FIGS. 13 C, F). These observations suggest that misexpressed Zic1 or Zic2 altered epidermal cell fate to neural and neural crest cell fate.

Next, the expression of several marker genes in the animal cap explants from Zic1 or Zic2 overexpressing blastula were examined (stage 9) (FIG. 14). Zic1 and Zic2 overexpression induced NCAM, a neuronal differentiation marker (N-rubulin; Chitnis et. al., "Primary neurogenesis in Xenopus embryos regulated by a homologue of the drosophila neurogenic gene Delta," Nature 375, 761–766 [1995]) and Xtwi expression in the explants, as expected based on the above results. In addition, a mid-hindbrain junction marker (En2; Hemmati-Brivanlou et. al., "Cephalic expression and molecular characterization of Xenopus En-2," Development 3: 715–724 [1991]), but not a spinal cord marker [HoxB9 (which is the same as Xlhbox6); Wright et. al., "The Xenopus XlHbox6 homeo protein, a marker of posterior neural induction, is expressed in proliferating neurons," Development 109: 225–234 [1990]) was induced by Zic1 or Zic2 overexpression. These findings indicate that neural tissue generated by the Zic1 or Zic2 overexpression has characteristics of anterior neural tissue similar to those observed with Zic3 overexpression. These inductions appeared to occur without mesoderm induction since no mesodermal marker (M. actin; muscle actin) was induced in this case.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); 1 or L (liters); ml (milliliters); µl (microliters); cm (centimeters); mm (millimeters); µm (micrometers); nm (nanometers); and ° C. (degrees Centigrade).

Example 1

Cloning of the Zic3 Gene (1) Preparation of Poly(A+) RNA from Xenopus Laevis Neurula Eggs of *Xenopus laevis* (Hamamatsu Seibutsu Kyozai, Shizuoka Pref.) were incubated artificially according to the method of Newport et al. (Newport et al., "A major developmental transition in early Xenopus embryos: I. characterization and timing of cellular changes at the midblastula stage," Cell 30:675–686 [1982]) to obtain embryos. The embryo was dipped in 2% cysteine-HCl (pH 7.8) to remove the jelly coat and then cultured in 0.1× Steinberg's solution (60 mM NaCl, 0.67 mM KCl, 0.34, mM Ca(NO$_3$)$_2$, 0.83 mM MgSO$_4$, 10 mM Hepes, pH 7.4), followed by recovery of the neurula.

From the recovered neurula, total RNA was extracted according to AGPC method. Subsequently, poly(A+) RNA was separated and purified therefrom using Oligotex dT30 (Roche).

(2) Preparation of a cDNA Library cDNA was synthesized using the poly(A+) RNA from (1) above and TIME SAVER cDNA Synthesis Kit (Pharmacia). Briefly, single-stranded cDNA fragments were synthesized using the poly(A+) RNA as a template, oligo(dT)$_{12-18}$ primers and a cloned mouse reverse transcriptase. Then, double-stranded cDNA fragments were synthesized using *E. coli* RNase H and *E. coli* DNA polymerase.

The resultant double-stranded cDNA fragments were blunt-ended using Klenow fragment (Nippon Gene). Thereafter, an adaptor having an EcoRI restriction site at one end and a blunt end at the other end was ligated to the cDNA fragments using T4 DNA ligase. After phosphorylation of the EcoRI restriction site with T4 polynucleotide kinase, the cDNA fragments were introduced into the EcoRI site in the multicloning site of A ZAP II (a phage cloning vector) using a commercial kit (ZAP II VECTOR KIT; Stratagene). Thus, the packaging of cDNA was performed. Subsequently, the resultant phage vector was transformed into *E. Coli* XL-1 blue, a host, to thereby prepare a CDNA library.

(3) Preparation of Primers Specific to the Amino Acid Sequence of the Zinc Finger Motif of the Zic Gene Family Primers were synthesized based on well conserved amino acid sequences in the mouse zinc finger domain. Briefly, 5' primer, 5'-GAGAACCTCAAGATCCACAA-3' (SEQ ID NO: 5) was synthesized based on Glu Asn Leu Lys Ile His Lys (SEQ ID NO: 3). The 3' primer, 5'-TT(C/T)CCATG(A/G)ACCTTCATGTG-3' (SEQ ID NO: 6) was synthesized based on His Met Lys Val His Glu Glu (SEQ ID NO: 4).

The synthetic oligonucleotides were chemically synthesized with an automated synthesizer (Applied Biosystem).

(4) Preparation of a cDNA Probe for Clone Isolation by PCR

PCR was performed using the cDNA from (2) above as a template and the 5' and 3' primers from (3) above. The composition of the PCR reaction solution was as follows.

First strand cDNA solution 1 µl
Sterilized water 70 µl
10× PCR buffer 10 µl
25 mM MgCl$_2$ 6 µl
2 mM dNTP mix 10 µl
100 µM 5' primer (sense) 1 µl
100 µM 3' primer (antisense) 1 µl
5 U/µl Taq polymerase 1 µl After the above reaction solution was thoroughly mixed, 50 µl of mineral oil was layered over the solution. PCR was performed in a DNA thermal cycler for 30 cycles, one cycle consisting of reaction at 94° C. for 1 min, at 55° C. for 1 min and at 74° C. for 2 min. As a result, a fragment of 208 bp was obtained. This fragment was labelled with β-$^{32}$P-dCTP using a random primer labeling kit (Takara) to obtain a cDNA probe for clone isolation.

(5) Isolation of a Clone

The cDNA library obtained in (2) above was plated on 12 NYZ plates (Falcon) so that ca. 150,000 plaques would be formed per plate. Upon this plate, a nylon filter Colony/Plaque Screen (Dupont NEN) was placed and fixed with 0.5 N NaOH aqueous solution. Next, hybridization was performed in a hybridization buffer (50% formamide, 1 M NaCl, 10% dextran sulfate, 1% sodium dodecyl sulfate, 100 µg/ml denatured salmon sperm DNA) containing the labelled probe from (4) above at 42° C. for 18 hours.

One clone was obtained from this screening. XL1-Blue was co-infected with the resultant clone and a helper phage R408 (Stratagene) to thereby cut out the cDNA insert from AZAP II to pBluescriptSK(-), which was then transformed into XL1-Blue. As a result, one clone having an insert of ca. 2.4 kb was obtained.

(6) Determination of the cDNA Nucleotide Sequence

The nucleotide sequence of the clone obtained in (5) above was analyzed using ABI PRISMum Dye Cycle Ready Reaction Kit (Perkin-Elmer) and a fluorescent automated DNA sequencer (Applied Biosystems). As a result, the nucleotide sequence for Zic3 gene with a length of 2364 bases was obtained (SEQ ID NO: 1). This cDNA had a deduced amino acid sequence consisting of 441 amino acids (SEQ ID NO: 2).

A homology search was performed against GenBank/EMBL nucleic acid databases using FESTA homology search program (Pearson et aL, Proc. Natl. Acad. Sci. USA 85: 2444–2448 [1988]). As a result, the nucleotide sequence of the gene of the invention exhibited 76% homology to that of mouse Zic3 gene (Aruga, J. et al, J. Biol. Chem. 271: 1043–1047 [1996]). With respect to the amino acid sequence, the gene of the invention exhibited 66% and 35% homology to other Zic (Aruga, J. et al., J. Biol. Chem. 271: 1043–1047 [1996]) and opa (Benedyk et al., Genes Dev. 8: 105–117 [1994]), respectively. Accordingly, the gene of the invention was designated Xenopus Zic3 (also called the "Zic3 gene" or "Zic3").

Example 2

Functions of the Zic3 Gene (1) Analysis of the Expression Pattern of Zic3 in Xenopus Embryos In order to elucidate the expression pattern of the Zic3 gene of the invention in Xenopus embryos, whole mount in situ hybridizations were performed (Daniel, H.S. et al., J. Biochem. Biophys. Methods 31: 185–188 [1996]).

A digoxigenin (DIG)-labelled RNA probe for hybridization was synthesized according to the method of Harland (Harland, R. M., Methods in Cell Biology 36: 685–694 [1991]). Briefly, RNA was synthesized from 2.5 µg of the cDNA clone containing the Zic3 gene obtained in Example I using RNA polymerase, followed by DIG labelling. After the resultant DIG-labelled RNA probe was treated with DNase, sodium acetate solution was added thereto to give a final concentration of 0.5 M and then the probe was ethanol-precipitated with 3 volumes of ethanol. The resultant mixture was micro-centrifuged for 5 min at 12,000 rpm to precipitate the probe, which was re-suspended in 20 µl of 80% formamide and stored at −20° C.

Also, Xenopus embryos cultured up to individual stages in the same manner as described in section (1) in Example 1 were fixed with a formalin fixative and stored in methanol at −20° C. For the purpose of in situ hybridization, the embryos were distributed into 5 ml screw vials. The vial was shaken on Nutator (Becton-Dickinson) at room temperature.

The embryo was dipped in 50% methanol/50% 0.1 M triethanolamine (TEA, pH 7.5) for 5 min and then washed with TEA for 5 min. The embryo was incubated for 16 min in a mixture of TFA and acetic anhydride mixed at a ratio of 1 ml:5 µSubsequently, the embryo was dipped in a mixed solution of TEA and 3.7% formaldehyde for fixation. Pre-hybridization was performed by adding thereto a prehybridization solution (50% formamide, 5×SSPE, 5% SDS, 1 mg/ml Torula RNA) and allowing it to stand at 60° C. for 1 hr and 10 min. Then, the prehybridization solution was replaced with a sufficient amount of a hybridization solution (obtained by adding the DIG-labelled RNA probe to the prehybridization solution at 1 µg/ml) . An overnight incubation was performed at 60° C. for hybridization.

After the hybridization, the embryo was washed twice with 2× SSC containing 50% formamide at 60° C. for 30 min each time. Subsequently, the embryo was rinsed with maleate buffer (MAB; 100 mM maleic acid, 150 mM NaCl, pH 7.5) for 5 min and then blocked with MAB containing 2% BMB (Boehringer-Mannheim Blocking Reagent) for 1 hr. The embryo was further incubated in MAB containing 2% BMB and 20% thermally-treated sheep serum for 1 hr. Next, anti-dioxigenin antibody-conjugated alkaline phosphatase (Boehringer-Mannheim) was added thereto at 0.5 µl/ml, and incubation was continued for another 4 hr at room temperature. The resultant embryo was washed with MAB for 1 hr at least 5 times, and then dipped in alkaline phosphatase buffer (100 mM Tris, 50 mM $MgCl_2$, 100 mM NaCl, pH 9.5) for 10 min at room temperature for equilibration.

Per ml of the above buffer, 4.5 µl of nitroblue tetrazolium solution (NTB; 75 mg/ml of 70% dimethylformamide) and 3.5 µl of 5-bromo-4-chloro-3-indolylphosphoric acid (BCIP; 50 mg/ml of dimethyformamide) were added. The resultant mixture was incubated to induce coloring reaction. The coloring was terminated by adding TE (10 mM Tris-HCl, 1 mM EDTA, pH 8.0). Re-fixing and mounting were carried out according to the method of Harland (Harland, R. M., Methods in Cell Biology 36: 685–694 [1991]).

As a result, Zic3 expression was detected at early gastrula in the dorsal lip and in the prospective neural plate [FIG. 1A (stage 10.25) and B (stage 10.5)]. In FIG. 1, an arrow indicates the gastrula and arrowheads indicate the prospective neural plate.

As gastrulation proceeded, expression of the Zic3 gene of the present invention decreased in the dorsal lip and increased in the prospective neural plate [FIGS. 1B and C (stage 10.5)]. FIG. 1C shows a cross section of the embryo shown in FIG. 1B.

In late gastrula, Zic3 expression diminished gradually in the central region (FIG. 1D, stage 12) . At the neural plate stage (FIG. 1E, stage 14), Zic3 was expressed strongly in the prospective regions of mesencephalon and anterior rhombencephalon. Thereafter, Zic3 expression became stronger in the anteriorneural holds, whereas that in the trunk neural folds remained weak (FIG. 1F, stage 16).

At early tailbud stage (FIGS. 1G and H, stage 20), Zic3 expression became gradually restricted to the dorsal region of the forebrain (telencephalon and diencephalon), the midbrain and the hindbrain, and its expression was weak in the dorsal region of the trunk.

After mid-tailbud stage, Zic3 expression disappeared in the diencephalon, but additional expression could be definitely confirmed in the lateral mesoderm of the tailbud region (FIG. II, stage 30). The cross section through the head at stage 30 showed that Zic3 expression was restricted to the dorsal part of the neural tube (FIG. 1J). In FIG. 1J, "nt" represents the neural tube; "e" represents eyes; "fg" represents fore-gut. From these results, it was found that Zic3 is expressed in those regions which are closely related to early neurogenesis.

(2) RT-PCR Analysis of the Temporal Expression Profiles of Zic3 and Various Neural Marker Genes Because Zic3 is expressed in the prospective neural plate region during gastrulation, the temporal expression profile of Zic3 was compared with those of other neural marker genes.

The marker genes used in this experiment were genes coding for NCAM, *N-tubulin* and transcription factors XASH-3, XATH-3, X1POU2 and NeuroD [Lee, J. E. et al., Science 268: 836–844 (1995); Ferreiro, B. et al., Development 120: 3649–3655 (1994); Turner et al., "Expression of achaete-scute homolog 3 in Xenopus embryos converts ectodermal cells to a neural fate," Genes Dev. 8:1434–1447 (1994); Takebayashi, K. et al., EMBO J. 16:384–395 (1997); Witta, S. E. et al., Development 121: 721–730 (1995); Chitnis, A. et al., Nature 375: 761–766 (1995); Kintner, C. R. et al., Development 99: 321325 (1987); Zimmerman, K. et al., Development 119: 221–231(1993); Oschwald, R. et al., Int. J. Dev. Biol. 35: 399–405(1991)].

These genes can be obtained by synthesizing primers from the nucleotide sequence of the relevant gene described in the above references, using genomic DNA from Xenopus or the like as a template and utilizing PCR techniques known in the art to amplify the relevant gene.

Comparison of temporal expression profiles was performed by RT-PCR. Briefly, total RNA was extracted separately from embryos at individual stages of egg, 8-cell, morula, blastula, gastrula, neurula and tailbud, and subjected to RT-PCR. As an indicator for RNA recovery ratio, Histone H4 was used (Turner et al., Nucleic Acids Res. 10:3769–3780 [1980]). As a positive control, sibling control embryos were used. As a control to check the absence of genomic DNA, PCR was performed without reverse transcription.

Specifically, each embryo of the above-indicated stage was suspended in 100 µl of a denaturing solution (4 M guanidine thiocyanate, 25 mM sodium citrate, 0.1 M 2-mercaptoethanol, 0.5% N-lauroyl sodium sarcosine) in a 1.5 ml microtube and shaken vigorously. To this suspension, 10 µl of 2 M sodium acetate (pH 4.0) was added and mixed thoroughly. Subsequently, 100 µl of water-saturated phenol was added thereto and mixed. Next, 30 µl of CIA (chloroform: isoamyl alcohol =49:1 by volume) and 1 µl of Etachinmate (Nippon Gene) were added to the mixture and shaken vigorously. The resultant mixture was left stationary on ice for 15 min. After centrifugation at 4° C. at 15,000 rpm for 20 min, the resultant upper layer was recovered into a fresh tube. Next, 250 µl of ethanol was added to the tube, which was centrifuged at 4° C. at 15,000 rpm for 10 min to thereby pellet the RNA. The supernatant was discarded, and the tube was air-dried. Next, 88 µl of sterilized water, 10 µl of 10× DNase buffer (BRL), 1 µl of RNasin (Promega), and 1 µl of DNaseI (Takara) were added to the tube and reacted at 37° C. for 1 hr to thereby degrade the DNAs mixed therein. Subsequently, 100 µl of ethanol was added to the tube, which was centrifuged at 40° C. at 15,000 rpm for 10 min to thereby pellet the RNA.

The supernatant was discarded. After the tube was air dried, 100 µl of solution K (0.01 M Tris, 0.005 M EDTA, 0.5% SDS, pH 7.8) and 1 µl of 20 mg/ml proteinase K solution were added to the tube and reacted at 37° C. for 1 hr to thereby degrade the proteins mixed therein. Next, 100 µl of phenol/CIA were added to the tube and mixed. The resultant mixture was centrifuged at 4° C. at 15,000 rpm for 10 min. Thereafter, 100 µl of CIA was added further and mixed. The resultant mixture was centrifuged at 4° C. at 15,000 rpm for 10 min. The resultant upper layer was recovered into a fresh tube, to which 250 µl of ethanol was added. Next, the tube was centrifuged at 4° C. at 15,000 rpm for 10 min to thereby pellet the RNA. The supernatant was discarded. The tube was air-dried and then allowed standing at room temperature.

The resultant RNA sample was dissolved in 10 µl of DPEC-treated water (obtained by adding 0.2 ml of diethylpyrocarbonate to 100 ml of distilled water, shaking the mixture vigorously and autoclaving it), and 3 µl of this solution was placed into a microtube. To the microtube, 1 µl of 100 pmol/µl random hexamer (Takara) and 7 µl of sterilized water were added and mixed thoroughly. The resultant mixture was incubated at 72° C. for 2 min and at 37° C. for 5 min. Subsequently, 4 µl of 5× RT buffer, 0.1 M DTT, 2 µl of 5 mM dNTP mix, and 0.5 µl of mouse leukemia virus (MMLV)-derived reverse transcriptase (BRL) were added thereto and mixed thoroughly. Next, a reverse transcription reaction was performed at 37° C. for 1 hr. Subsequently, the reaction solution was maintained at 98° C. for 10 min to terminate the reaction. Thus, a solution of the first strand cDNA was obtained and stored at −20° C. until use for the PCR synthesis of the second strand.

PCR was performed using the first strand CDNA solution obtained above as a template. The composition of the PCR reaction solution was as follows.

| | |
|---|---|
| First strand cDNA solution | 1 µl |
| Sterilized water | 70 µl |
| 10× PCR buffer | 10 µl |
| 25 mM MgCl$_2$ | 6 µl |
| 2 mM dNTP mix | 10 µl |
| 100 µM primer (sense) | 1 µl |
| 100 µM primer (antisense) | 1 µl |
| 5 U/µl Taq polymerase | 1 µl |

After the above reaction solution was mixed thoroughly, 50 µl of mineral oil was layered over the solution. PCR was performed 25–36 cycles, one cycle consisting of thermal denaturation at 94° C. for 0.5 min, annealing at 55° C. for 0.5 min and extension at 72° C. for 1 min. After completion of the reaction, 4 µl of the reaction solution was subjected to agarose gel electrophoresis to examine the amplified product. Thus, expression of each gene was investigated.

| Gene | | Primer | SEQ ID |
|---|---|---|---|
| Zic3 | (sense) | 5'-TTCTCAGGATCTGAACACAT-3' | (SEQ ID NO: 7) |
| | (antisense) | 5'-CCCTATAAGACAAGGAATAC-3' | (SEQ ID NO: 8) |
| XASH-3 | (sense) | 5'-GGACTCTCGCCTTGTGGC-3' | (SEQ ID NO: 9) |
| | (antisense) | 5'-GATATGTTCTTGTAATAGTCAGT-3' | (SEQ ID NO:10) |
| XATH-3 | (sense) | 5'-TGGACCTCAGGCCATGTTC-3' | (SEQ ID NO:11) |
| | (antisense) | 5'-GATGCTGAGTGGAGGTGTTA-3' | (SEQ ID NO:12) |
| XlPOU 2 | (sense) | 5'-ACCCAACGACCACGTGGACCTG-3' | (SEQ ID NO:13) |
| | (antisense) | 5'-AGCTCATTGCAGGAGGTGTCTG-3' | (SEQ ID NO:14) |
| NeuroD | (sense) | 5'-GTGAAATCCCAATAGACACC-3' | (SEQ ID NO:15) |
| | (antisense) | 5'-TTCCCCATATCTAAAGGCAG-3' | (SEQ ID NO:16) |
| NCAM | (sense) | 5'-CACAGTTCCACCAAATGC-3' | (SEQ ID NO:17) |
| | (antisense) | 5'-GGAATCAAGCGGTACAGA-3' | (SEQ ID NO:18) |
| IV-tubulin | (sense) | 5'-ACACGGCATTGATCCTACAG-3' | (SEQ ID NO:19) |
| | (antisense) | 5'-AGCTCCTTCGGTGTAATGAC-3' | (SEQ ID NO:20) |
| Histone H4 | (sense) | 5'-CGGGATAACATTCAGGGTATCACT-3' | (SEQ ID NO:21) |
| | (antisense) | 5'-ATCCATGGCGGTAACTGTCTTCCT-3' | (SEQ ID NO:22) |

Figure 2:
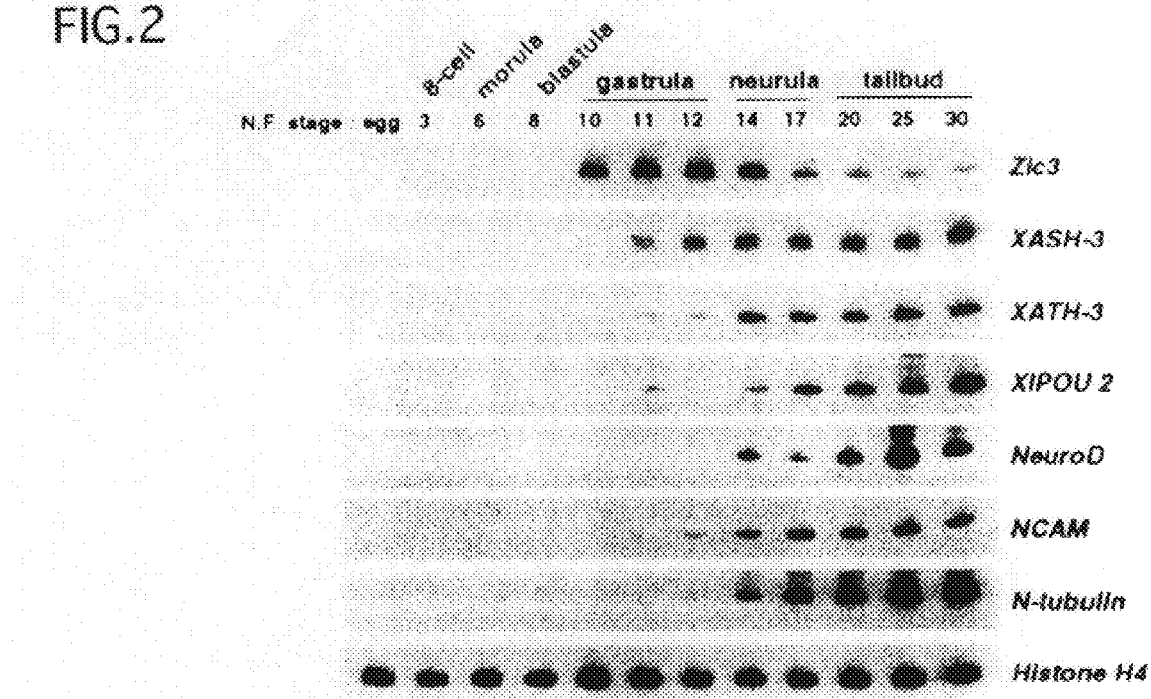
FIG. 2 presents autoradiographs showing the results of expression tests of the Zic3 gene.

The results are shown in FIG. 2. As is clear from FIG. 2, Zic3 expression was detected in early gastrula (stage 10). With respect to the expression of other neural marker genes, XATH-3 and NCAM were detected at mid-gastrulastage; and NeuroD and *N-tubulin* were detected at late gastrula stage. Although XASH-3 and X1POU 2 were detected also at early gastrula stage, their expression was extremely weak compared to Zic3 expression.

Zic3 was first detected in the prospective neural plate region immediately after neural induction (FIG. 1A). Therefore, the onset of expression of Zic3 and a neural inducer gene chordin which is known to be expressed at an early stage of neurogenesis (Sasai, Y. et al., Cell 79:779–790 [1994]) were precisely compared. This comparison was made with the following techniques.

Xenopus eggs were artificially fertilized with sperms in a culture plate, and the embryonic development of all the fertilized eggs was allowed to proceed in a synchronized manner. After the artificial fertilization, the eggs were cultured at 23° C. for 6 to 10.5 hr. Next, embryos were collected and immediately frozen. Zic3 RNA was extracted from these samples in the same manner as described in Section (1), Example 1, and subjected to RT-PCR. For chordin, an RT-PCR was performed using the following primers.

```
Chordin (sense)      5'-AACTGCCAGGACTGGATGGT-3'    (SEQ ID NO:23)

(antisense) 5'-GGCAGGATTTAGAGTTGCTTC-3'    (SEQ ID NO:24)
```

Figure 3:
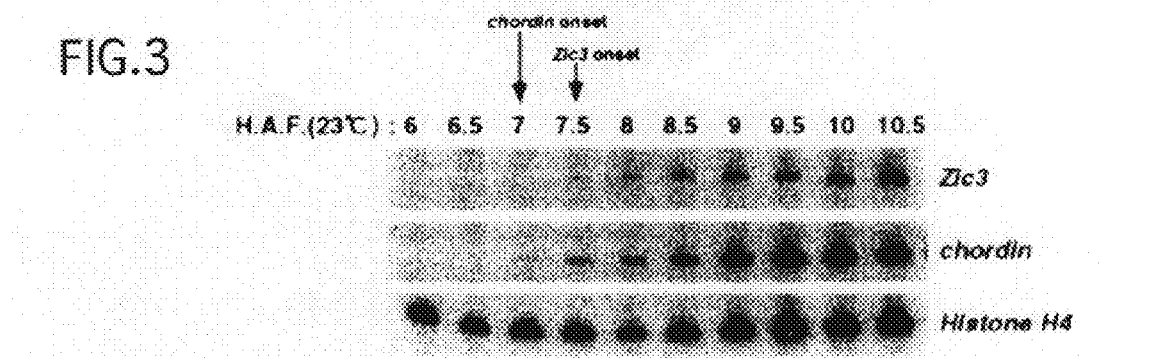
FIG. 3 presents autoradiographs showing the results of expression tests of the Zic3 gene.

As a result, it was found that the onset of Zic3 expression is 7.5 hr after the fertilization, whereas that of chordin is 7 hr after the fertilization (FIG. 3). The numbers indicated above the lanes represent hours of cultivation after the artificial fertilization. Since the onset of Zic3 expression is only 30 min later than that of chordin, it was found that, like chordin, Zic3 also induces the initial step of neural induction.

(3) Zic3 Expression-Inducing Mechanism

The ectoderm (animal cap) of *Xenopus laevis oocyte* can be neuralized by prolonged culture in dispersal (Grunz, H. et al., Cell Differ. Dev.28:211–218 [1989]; Godsave, S. F. et al., Dev. Biol. 134:486–490 [1989]). This occurs because ectoderm cells are relieved from neuralization repressors as a result of dispersion of the cells.

Next, whether Zic3 is induced in animal cap explants was examined. Briefly, an animal cap explant was dipped in a buffer without $Ca^{2+}$ and $Mg^{2+}$ ions and pipetted lightly to thereby obtain dispersed cells. The cells were cultured under such condition in a medium without $Ca^{2+}$ and $Mg^{2+}$ ions at 23° C. for 4 hr. Next, the cells were allowed to form a cell mass again, and the mass was cultured up to a time point equivalent to the neurula stage.

Subsequently, the expression of Zic3 and other genes (epidermal keratin, NCAM, Xtwi, Xslu and Histone H4) was tested by RT-PCR. Briefly, RNA was extracted from non-dispersed animal cap explants and dispersed animal cap explants. As primers for individual genes, the above-mentioned primers and those described below were used. A series of RT-PCRs were performed under the same conditions as in Section (1) in this Example (animal cap assay).

The results are shown in FIG. 4A. In each lane, "Intact" represents animal cap explants (non-dispersed cells); "Dispersed" represents animal caps cultured in dispersal; "Embryo" represents embryos; and "RT___" represents the results without reverse transcriptase. Zic3 expression was not detected in intact animal cap explants, though the expression of epidermal keratin (an epidermal marker gene) was detected on the other hands, expression of Zic3 and a neural marker gene NCAM was detected in dispersed cells, but expression of epidermal keratin was not detected.

The neuralization that occurs in animal cap-derived dispersed cells is considered to be due to the attenuation of BMP4-mediated signals which induce ectodermal cells into epidermal cells (Wilson, P. A. et al., Nature 376:331–333 [1995]). Therefore, the following experiment was performed on the assumption that Zic3 expression can actually be induced in vivo by blocking the BMP4-mediated signals, although an understanding of the mechanism is not necessary to practice the present invention and the present invention is not limited to any particular mechanism.

Briefly, a dominant negative form of BMP receptor (dnBMPR) mRNA (Suzuki, A. et al., Devlop. Growth. Differ. 37:581588 [1995]) was injected into embryos to over-express dnBMPR therein. Next, Zic3 expression in early gastrula stage embryos was examined by in situ hybridization in the same manner as described above.

Specifically, Zic3 mRNA and dnBMPR mRNA were synthesized by in vitro transcription. Zic3 mRNA (100 pg) was injected into a two-cell stage embryo with a glass microneedle. As a control, LacZ mRNA-injected early gastrula was used. dnBMPR mRNA (500 pg) was injected into the ventral region of a two-cell stage embryo, which was developed in 1× Steinberg's solution containing 5% Ficoll up to the early gastrula of stage 10.25. The resultant embryo was subjected to whole mount in situ hybridization which was performed in the same manner as described above to thereby examine Zic3 expression.

As a result, in both the dnBMPR mRNA-injected embryo and the dnBMPR mRNA non-injected embryo, Zic3 expression was observed at naturally expected sites (arrowheads, FIG. 4B). In the dnBMPR mRNA-injected embryo, expression of ectopic Zic3 was induced in the ventromarginal zone of the gastrula (arrows, FIG. 4B). This shows that injection of dnBMPR mRNA causes expression of excessive dnBMPR in cells, which in turn inhibits the BMP4 signals and induces the neuroectoderm (Zimmerman, L. B. et al., Cell 86:599–606 (1996)]. Thus, it was found that Zic3 expression can be induced in vivo by blocking the BMP4 signals.

```
Epidermal keratin (sense)      5'-CACCAGAACACAGAGTAC-3'      (SEQ ID NO:25)

(antisense)  5'-CAACCTTCCCATCAACCA-3'      (SEQ ID NO:26)

Xtwi              (sense)      5'-AGTCCGATCTCAGTGAAGGGCA-3'  (SEQ ID NO:27)

(antisense)  5'-TGTGTGTGGCCTGAGCTGTAG-3'   (SEQ ID NO:28)

Xslu              (sense)      5'-GCCCTATTTCCTTGTTGC-3'      (SEQ ID NO:29)

(antisense)  5'-AACCCTTCTTGGTTGCAC-3'      (SEQ ID NO:30)
```

(4) Zic3 Overexpression Test in Early Embryos

The expression pattern of Zic3 in Xenopus and its activity to regulate neural induction suggest that Zic3 plays some role in early steps of neurogenesis. Thus, the function of Zic3 was examined by overexpression experiment in embryos. First, Zic3 mRNA was injected into one blastomere of two cell stage embryos so that Zic3 would be overexpressed in the left or right hemilateral body alone.

Briefly, Zic3 mRNA, LacZ mRNA and dnBMPR mRNA were synthesized by in vitro transcription in the same manner as described above. Zic3 mRNA was injected into one blastomere of two-cell stage embryos or two blastomeres of eight-cell stage embryos independently or in combination with LacZ mRNA. The dnBMPR mRNA (500 pg) was injected into the ventral region of two-cell stage embryos. For the animal cap assay, Zic3 mRNA was injected into the animal hemisphere of the two blastomeres of two-cell stage embryos. As a control, embryos injected with LacZ mRNA alone or $H_2O$ alone or non-injected embryos were also tested. Injected embryos were cultured in 1× Steinberg's solution containing 5% Ficoll until mid-blastula stage. Next, they were transferred into 0.1× Steinberg's solution and subjected to animal pole assay at stage 9 or in situ hybridization at various stages in the same manner as described above.

Figure 5:
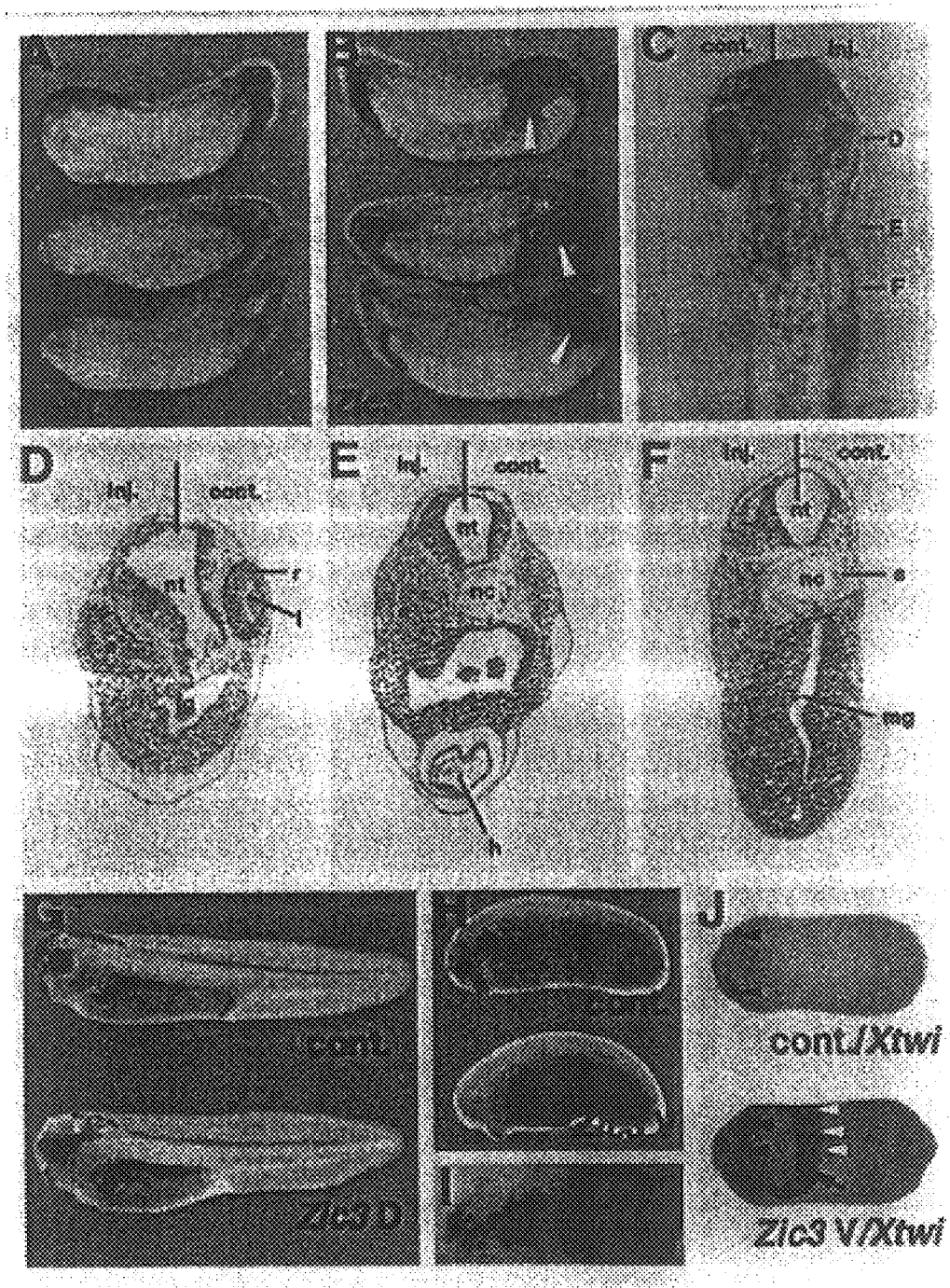
FIG. 5 panels A–J presents photographs showing the results of expression tests of the Zic3 gene (morphology of an organism).

The results are shown in FIG. 5. FIG. 5, panel A shows Zic3 mRNA uninjected control side of the embryo (stage 27); panel B shows Zic3 mRNA injected side (stage 27). Panel C shows a dorsal view of the anterior region of Zic3 mRNA injected embryo (stage 36). Panels D–F are microscopic photographs of transverse sections of the embryo shown in panel C. Panels G–J show overexpression of Zic3 when 100 pg of Zic3 mRNA or control LacZ mRNA was injected into two blastomeres of eight-cell stage embryos. In panel G (stage 36), mRNA was injected into two dorsoanimal blastomeres; in panels H–J (H, I: stage 25, J: stage 20), mRNA was injected into two ventroanimal blastomeres. In panels G and H, upper figures show lateral views of control LacZ mRNA injected embryos; and lower figures show lateral views of Zic3 mRNA injected embryos. Panel I shows higher magnification of the clusters in panel H. Panel J shows Xtwi expression in the embryos injected with LacZ mRNA or Zic3 mRNA into ventroanimal two blastomeres at eight-cell stage.

In almost all cases, the head side of the Zic3 mRNA injected embryos was enlarged and exhibiting poorly formed eyes (FIGS. 5B, C), whereas Zic3 mRNA uninjected embryos exhibited normally formed eyes (FIGS. 5A, C).

The sections through the head region of the Zic3 mRNA injected embryos showed that neural walls were considerably thickened in the injected side (FIGS. 5D–F). In addition to this change in neural walls, presumptive mesenchymal tissue, which may derive from the neural crest in the cephalic region, showed a remarkable hyperplasia. In most cases, however, neural retinas were considerably distorted and less hyperplastic (FIG. 5D). Additionally, retinal pigment cells diminished and, in particular, lenses were not induced at all (FIGS. 5C, D). Further, eye abnormalities were observed in the embryos injected with Zic3 mRNA into dorsal blastomeres (FIG. 5G, lower). Remarkable clusters of ectopic pigment cells appeared in the embryos injected with Zic3 mRNA into ventral blastomeres (FIG. 5H, lower). In contrast, no such abnormalities were observed in Zic3 mRNA uninjected embryos.

On the other hand, Xtwi expression was observed in the head neural crest of the control embryo (FIG. 5J, upper, arrowhead). In contrast, expression of ectopic Xtwi was induced near the ectopic clusters of pigment cells in the ventral side of Zic3 mRNA injected embryos (FIG. 5J, lower, white arrowheads). The expansion of the Xtwi expressing cephalic neural crest (FIG. 5J, lower, black arrowheads) was observed in eight-cell stage embryos, and ectopic clusters of pigment cells were observed in the cephalic region (FIG. 5B).

Subsequently, Zic3 mRNA was injected into two dorsoanimal or ventroanimal blastomeres of eight-cell stage embryos to express Zic3 restrictedly at the dorsal or ventral side (FIGS. 5G–J). This experiment was performed in the same manner as described above using 80 embryos.

When Zic3 mRNA was injected into dorsoanimal blastomeres, heads of the embryos were enlarged, and the eyes showed abnormalities in the neuroepithelium of retina, diminishing of retinal pigment cells and loss of lens (these changes are the same as observed in the embryos injected at two-cell stage) (58/80 embryos tested) (FIG. 5G). In the anterior region, neural tube closure was delayed. Pigment cells were found in the dorsal head (58/80 embryos tested).

In contrast, when Zic3 mRNA was injected into ventroanimal blastomeres, clusters of ectopic pigment cells appeared in the ventral epidermis (90/111 embryos tested). The clusters of the ventral pigment cells were arrayed remarkably on the ridge of the hyperplastic tissue which transverses the ventral side. These pigment cells were considered to be melanocytes which are derived from the neural crest. Therefore, in situ hybridization of Zic3 mRNA injected embryos using a neural crest marker Xtwi as a probe was performed. The in situ hybridization techniques used were the same as described in (1) above.

As a result, ectopic Xtwi expression was observed near the ectopically appearing clusters of pigment cells in addition to the expansion of the Xtwi-expressing region in the cephalic neural crest.

(5) The Role of Zic3 in Early Embryogeny

In order to examine how the overexpression of Zic3 alters cell fate in early stage embryos, the inventors tested the expression of NCAM, Xtwi, Xslu and EpA (an epidermal antigen gene) (Jones, E. A. & Woodland, H. R.: Cell 44:345–355 [1986]) in early neurulas.

Briefly, a total of 100 pg of Zic3 mRNA was injected into a blastomere of two-cell stage embryos. The expression patterns of the above genes were examined at stage 14 by in situ hybridization using NCAM and Xslu probes and by immunohistochemical staining using EpA monoclonal antibody (obtained from Mr. E. Jones of Univ. of Warwick, UK).

Figure 6:
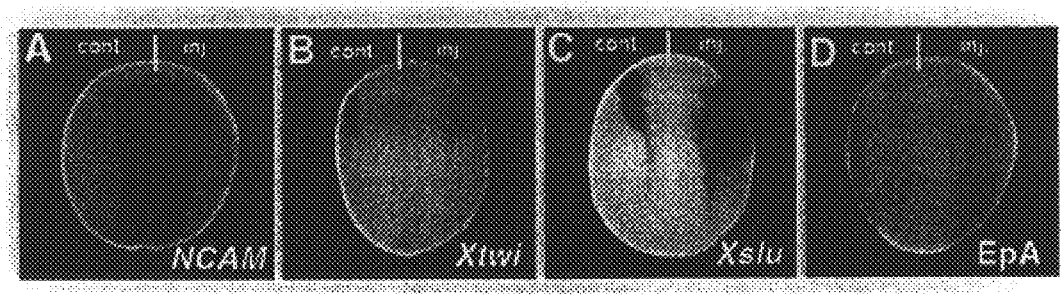
FIG. 6 panels A–D present photographs showing the results of expression tests of the Zic3 gene (morphology of an organism).

The results are shown in FIG. 6. In FIGS. 6A–D, any of the panels shows a dorsal view of a stage 14 embryo. Panel A, panel B and panel C show the results when NCAM, Xtwi and Xslu were used as a probe, respectively. Panel D shows the results when EpA monoclonal antibody was used.

NCAM expression increased markedly in the anterior neural plate region of the Zic3 mRNA injected side (31/45 embryos tested) (FIG. 6A). Xtwi (43/45 embryos tested) and Xslu (12/12 embryos tested) expression in neural crest cells was also increased by the injection (FIGS. 6B and C). However, in the Zic3 mRNA injected site of the epidermis, EpA staining was decreased (FIG. 6D).

If it is assumed that epidermal fate changes into neural and neural crest fate as a result of the injection of Zic3 mRNA, the epidermis should be reduced at the site of Zic3 mRNA injection. To test this possibility, the expression of EpA in Zic3 mRNA injected embryos was determined as described below. Briefly, embryos were dipped in Dent's fixative (20% dimethyl sulfoxide, 80% methanol) and shaken gently several times. Next, they were left at −20° C.

overnight for fixation. After removal of the fixative, a bleach (10% H$_2$O$_2$, 47% methanol, 20% DMSO) was added to the embryos, which were then left standing for 1 to 2 days for bleaching. After removal of the bleach, 100% methanol was added to the embryos, which were then stored at −20° C. Thereafter, the embryos were washed with TBS (50 mM Tris-HCl (pH 7.5), 150 mM NaCl, 0.05% Tween 20) for 20 min twice. On the other hand, EpA monoclonal antibody was diluted to 1/100 to 1/1000 with TBS containing 20% normal goat serum. Using the resultant dilution, the embryos were primarily stained at 4° C. overnight. Subsequently, the embryos were washed with TBS for 1 hr 5 times. Next, using ca. 200-fold dilution of peroxidase conjugated secondary antibody in TBS containing 20% normal goat serum, the embryos were secondarily stained at 4° C. overnight. After 1 hr staining with TBS 5 times, the embryos were secondarily stained with a coloring solution (TBS containing 0.5 mg/ml diaminobenzidine and 0.02% H$_2$O$_2$). After a color of an appropriate density was formed, the embryos were washed with 100% methanol for 10 min twice. Subsequently, the embryos were dipped in BABB solution (benzyl alcohol:benzylbenzoate=1:2) to make them transparent, followed by storing in 100% methanol.

| En-2 | (sense) | 5'-CACAAGGGGTTAAAGGCAAG-3' | (SEQ ID NO:37) |
| --- | --- | --- | --- |
|  | (antisense) | 5'-CCCAGTGTCTCTCTCAGTAT-3' | (SEQ ID NO:38) |
| XlHbox6 | (sense) | 5'-TACTTACGGGCTTGGCTGGA-3' | (SEQ ID NO:39) |
|  | (antisense) | 5'-AGCGTGTAACCAGTTGGCTG-3' | (SEQ ID NO:40) |

As a result, expression of EpA was significantly reduced in the Zic3 injected site (FIG. 6D). This fact indicates that Zic3 alters epidermal cell fate into neural and neural crest cell fate.

(6) Function Expression Test for Zic3

The above studies suggest that Zic3 plays important roles in early neural and neural crest development. In order to examine how Zic3 acts in these processes, the expression of several marker genes were tested by RT-PCR in Zic3 mRNA injected animal cap explants.

One hundred pg of Zic3 or LacZ mRNA (control) was injected into two-cell stage embryos. The animal cap of each embryo was explanted at stage 9 and cultured. When the sibling embryos reached stage 20, the expression of neural marker genes (NCAM, Neurogenin, NeuroD, XASH-3, XATH3, XIPOU 2) and neural crestmarkers (Xtwi, Xslu) was examined by RT-PCR. Also, the expression of an early mesodermal marker Xbra (*Xenopus brachyury*) and a dorsal mesodermal marker M. actin (muscle actin) was examined by RT-PCR when the sibling embryos reached stage 10.5 and stage 20, respectively, in the same manner as describe above. For Neurogenin, Xbra and *M. actin,* an RT-PCR was performed using the following primers.

Neurogenin
(sense) 5'-CAAGAGCGGAGAAACTGTGT-3' (SEQ ID NO:31)
(antisense) 5'-GAAGGAGCAACAAGAGGAAG-3' (SEQ ID NO:32)

Xbra
(sense) 5'-GTCCGTACACTCACAGAAAC-3' (SEQ ID NO:33)
(antisense) 5'-GAGGTGTAGAGCCAAGTAAG-3' (SEQ ID NO:34)

*M. actin*
(sense) 5'-GCTGACAGAATGCAGAAG-3' (SEQ ID NO:35)
(antisense) 5'-TTGCTTGGAGGAGTGTGT-3' (SEQ ID NO:36)

Figure 7:
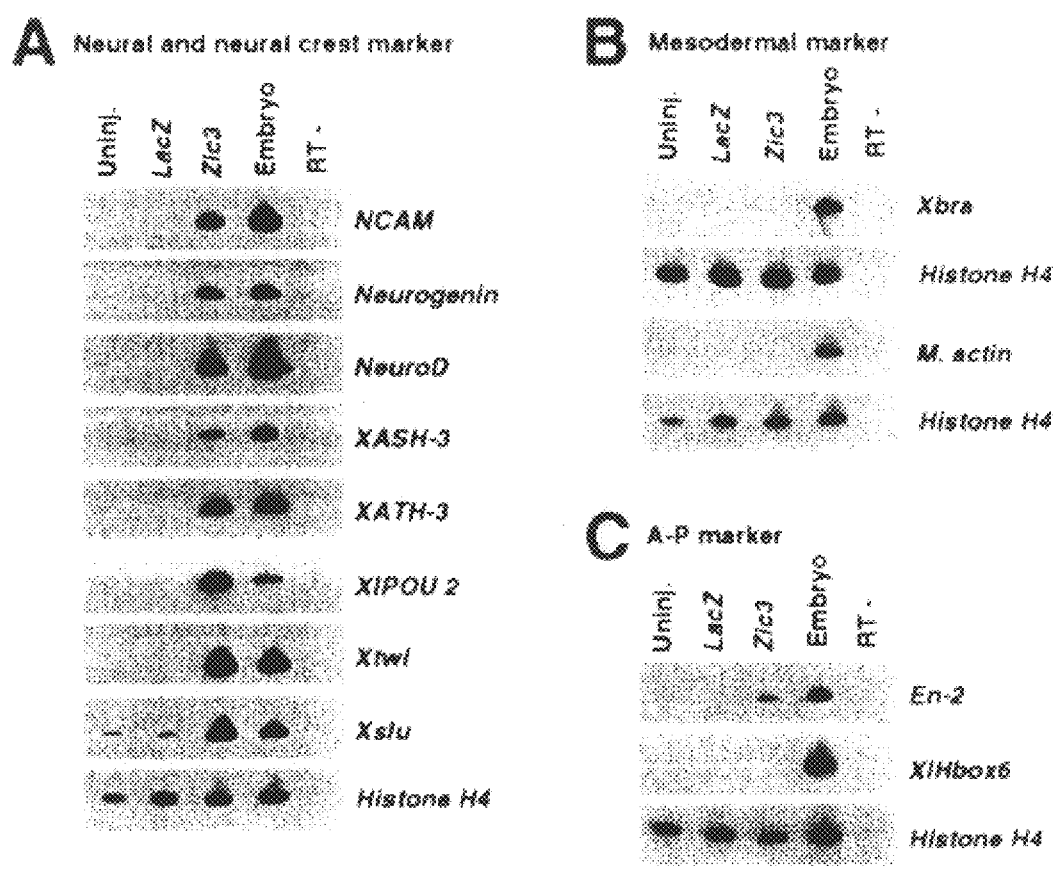
FIG. 7 panels A–C present autoradiographs showing the results of expression tests of the Zic3 gene.

The results are shown in FIG. 7. Zic3 induced all of the neural and neural crest marker genes tested. Although uninjected (Uninj.) or LacZ injected (LacZ) caps did not express any of these markers, animal caps injected with Zic3 mRNA (Zic3) expressed all of the neural and neural crest marker genes tested (FIG. 7A). However, Zic3 did not induce mesodermal markers (FIG. 7B).

These results demonstrate that Zic3 is able to direct the induction of neural tissues except mesoderm and that Zic3 is able to change directly the epidermal fate of cells to neural and neural crest fate. Further, the expression of a molecular marker En-2 expressed in anterior neural plate (Hemmati Brivanlou, A. et al., Development 111:715–724 [1991]) and a posterior marker X1Hbox6 (Wright, C. V. E. et al., Development 109:225–234 [1990]) was tested by RT-PCR in the same manner as described above. For En-2 and X1Hbox6, an RT-PCR was performed using the following primers.

As a result, though the anterior neural marker En-2 was induced, the posterior marker X1Hbox6 was not induced (FIG. 7C). This result is consistent with the previous finding that the neural tissue generated by the blockage of BMP4 signals is anterior neuroectoderm (Hemmati-Brivanlou, A. et al., Cell 77:283–295 [1994]; Sasai, Y. et al., Nature 376:333–336 [1995]; Lamb, T. M. et al., Science 262:713–718 [1993]). Therefore, it has become clear that Zic3 has an activity to induce anterior neuroectoderm.

Figure 4:
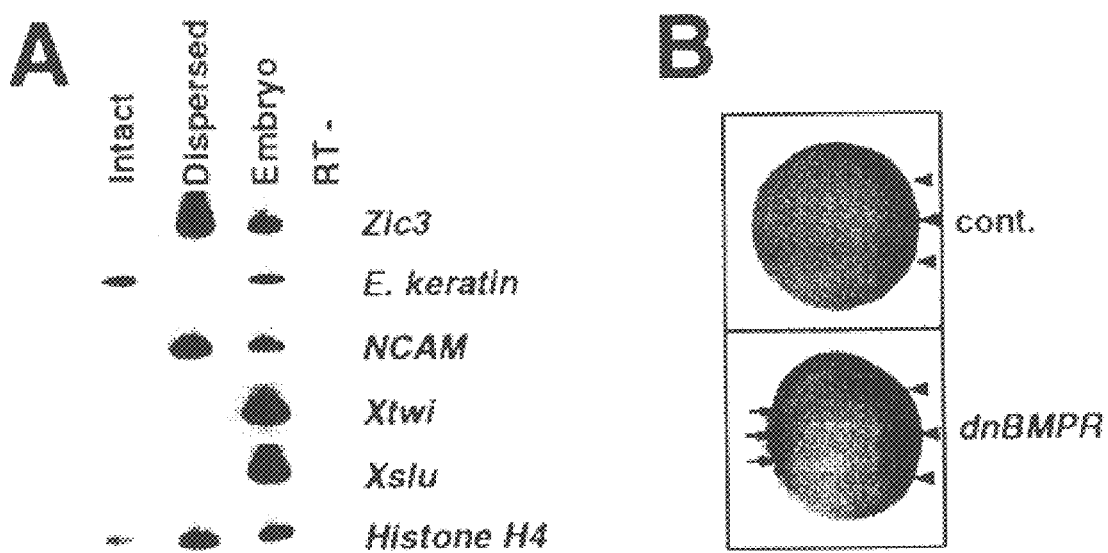
FIG. 4 panels A and B present autoradiographs showing the results of expression tests of the Zic3 gene and photographs showing morphology of an organism.

Zic3 overexpression induced the neural marker NCAM and the neural crest markers Xtwi and Xslu in explants (FIG. 7A). This presents a contrast to the result that Zic3 was expressed, but Xtwi and Xslu were not, in dispersed animal cap cells (FIG. 4).

From the results described above, it has been shown that Zic3 induces the so-called proneural genes and that Zic3 acts upstream of these proneural genes. Therefore, Zic3 has neurogenesis-inducing activity, and in particular, early neurogenesis-inducing activity and thus, can be called a master gene for neural induction.

Example 3

Isolation of Xenopus Zic1 and Zic2 cDNA Clones

Xenopus neurula (stage 17) cDNA was subjected to 30 cycles of PCR (at 94° C., 1 min.; 55° C., 1 min and 74° C., 1 min, respectively) (Nakata et al., 1997). The 5' primer was a 5'-GAGAACCTCAAGATCCACAA-3' (SEQ ID NO: 5), derived from ENLKIHK (SEQ ID NO: 3); sequence based on zinc finger domain of the mouse Zic family genes), and the 3' primer was 5'-TT(C/T)CCATG(A/G)ACCTTCATGTG-3' (SEQ ID NO: 6), which was the reverse translation of HMKVHEE (SEQ ID NO: 4). A 208 bp PCR product was sequenced. The fragment was used to screen a lambda ZAP cDNA library prepared from Xenopus neurula embryos (Pharmacia Biotech; TIME SAVER cDNA Synthesis Kit, Strategene; Lambda ZAP$^R$II Vector Kit) under low stringency conditions. Two cDNA clones were isolated (Zic1, 1.8 kb: Zic2, 2.9 kb) and these were auto-sequenced by ABI PRISM Dye Primer Cycle Sequencing Ready Reaction Kit (Perkin-Elmer).

Example 4

Plasmid Construction

The Zic1 open frame reading (275–1825, pZic1) (end-filled) fragment was cloned into the StuI site of the pCS2+ vector (Turner and Weintraub, 1994) (pCS2+Zic1). The full-length Zic2 coding region was cloned into the EcoRI-XbaI site of the pCS2+ vector by PCR amplification of pZic2 (452–1957) (pCS2+Zic2).

The Zic3 open reading frame (EcoRI [−10: that lies in the vector immediately 5' to the end of the cDNA]-StuI [1460]; pZic3) fragment was cloned into the EcoRI and StuI sites of the pCS2 vector (pCS2+Zic3). The full-length coding region of each Zic gene family was also cloned in-frame into the EcoRI-XbaI site of the pCS2+MT (myc-tag) vector (Turner and Weintraub, 1994) by PCR amplification from the original cDNA phagemid (pCS2+MT-Zic1, pCS2+mT-Zic2, and pCS2+MT-Zic3).

Example 5

Embryo Manipulations

*Xenopus laevis* were purchased from Hamamatsu Seibutsu Kyozai, (Shizuoka, Japan). Embryos were obtained by artificial fertilization (Newport and Kirschner, 1982). The jelly coats were removed by immersing the embryos in 2% cystein-HCl (pH 7.8). Embryos were cultured in 0.1× Steinberg's solution and staged according to Nieuwkoop and Faber (Nieuwkoop, P. D., Faber, J., "Normal Table of *Xenopus laevis* (Daudin) North-Holland, Amsterdam [1967]).

Microinjection was carried out as previously described (Moon and Christian, "Microinjection and expression of synthetic mRNAs in Xenopus embryos," Technique 1: 76–89 [1989]). mRNA for injection was synthesized by in vitro transcription. Xenopus Zic1, Zic2 or Zic3 mRNA was injected with or without LacZ mRNA (a gift from Dr. A. Muto) into one or two blastomeres of 2-cell stage embryos or two blastomeres of 8-cell stage embryos. For animal cap assay, mRNA was injected into the animal side of two blastomeres of 2-cell stage embryos. Injection of LacZ mRNA alone or no injection was done as a control in these experiments. Injected embryos were cultured in 5% Ficoll in 1×Steinberg's solution. The embryos were replaced in 0.1× Steinberg's solution at midblastula stage and were subjected to animal cap assay at stage 9 or whole-mount in situ hybridization at various stages.

For preparation of animal cap explants, 6 animal caps were dissected from Xenopus Zic1, Zic2 or Zic3 mRNA injected or uninjected embryos in 1× MMR at stage 9 and cultured in 0.5× MMR.

Example 6

RNA Isolation and RT-PCR Assay

Preparation of total RNA and RT-PCR assay were carried out as previously described (Nakata et al., 1997). Histone H4 or EF-1a was used to monitor RNA recovery. Sibling control embryos served as positive controls. PCR was performed with RNA that had not been reversed-transcribed to check for DNA contamination. Some primer sequences were obtained from The Xenopus Molecular Marker Resource (See e.g., http://vize222.zo.utexas.edu/). In addition, the following primers were used:

Zic1:

5'-ATGAAGGTCCACGAAGCATC-3' (SEQ ID NO:45)

5'-CGTGCTGTGATTGGACGTGT-3' (SEQ ID NO:46)

Zic2:

5'-ACGGCAGCGTTATCTCCTAG-3' (SEQ ID NO:47)

5'-TATACACCGAGGGAGGCATC-3' (SEQ ID NO:48)

Example 7

Histology and Whole-mount in Situ Hybridization

Whole-mount in situ hybridization was performed essentially as described previously (Chitnis et al., 1995; Shain and Zuber, "Sodium dodecyl sulfate (SDS)-based whole-mount in situ hybridization of Xenopus laevis embryos," J. Biochem. Biophys. Methods 31, 185–188 [1996]) using digoxigenin-labeled antisense probes for Zic1, Zic2, NCAM (Kinter and Melton, 1987), and Xslu (Mayor et al., 1995). Some stained embryos were then embedded in paraplast and sectioned at 5 $\mu$m using a microtome. Whole-mount immunohistochemistry was performed essentially as described previously using EpA monoclonal antibody (Jones and Woodland, 1986).

Example 8

Western Blotting

Pools of 20 embryos were homogenized in lysis buffer containing 10 mM Tris-HCl (pH 7.5), 100 mM NaCl, 1 mM EDTA, 0.1 mM PMSF and 0.1 mM leupeptin. Proteins were separated by 7.5% SDS-polyacrylamide gel electrophoresis and immunoblotted with the anti-c-myc antibody (9E10, Santa Cruz Biotechnology) diluted 1:1000 (0.1 mg/ml).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular and cellular biology, biochemistry, or related fields are intended to be within the scope of the following claims.

We claim:

1. An isolated nucleotide sequence encoding a protein having the amino acid sequence set forth in SEQ ID NO: 42.

2. The nucleotide sequence of claim 1, as set forth in SEQ ID NO: 41.

3. A recombinant vector comprising the nucleotide sequence of claim 2.

4. A host cell comprising the recombinant vector of claim 3.

5. A method for producing a neurogenesis inducing protein, comprising the steps of:
   a) providing:
      i) the recombinant vector of claim 3, and
      ii) a host cell;
   b) introducing said recombinant vector into said host cell to produce a transformed cell which contains said recombinant vector and expresses said neurogenesis inducing protein;
   c) culturing said transformed cell to produce said neurogenesis inducing protein; and
   d) isolating said neurogenesis inducing protein.

6. The recombinant vector of claim 3, wherein said vector comprises in operable linkage a promoter and the nucleotide sequence as set forth in SEQ ID NO:41, within a vector backbone, and wherein said vector backbone is a viral nucleotide sequence selected from the group consisting of adenovirus, adeno-associated virus, herpes virus, vaccinia virus and retrovirus.

7. A composition comprising the recombinant vector of claim 3 and liposomes.

* * * * *

SEQUENCE LISTING

<160> NUMBER OF SEQ ID NOS: 64

<210> SEQ ID NO 1
<211> LENGTH: 2364
<212> TYPE: DNA
<213> ORGANISM: Xenopus laevis

<400> SEQUENCE: 1

| | | | | | |
|---|---|---|---|---|---|
| ctcagttgga | gagggtgaac | tgtttccagg | attttcggaa | gcaaaggaa | ttaaaagata | 60 |
| acttttccc | cccgaacatt | ccacatgaac | tgtatccagt | gctgaccaca | gatcagcttg | 120 |
| tactgctcag | ctcattcatg | acaatgctat | tagatggagg | accgcagttt | cccaccctgg | 180 |
| gagttcgtgg | gtttgggaca | gctcgccatc | atgagatgtc | caaccgagat | gctggcatgg | 240 |
| ggcttaatcc | attcactgag | ccttctcatg | ctgcggcttt | taagctcagt | ccagcaagtc | 300 |
| atgatctttc | ttcaagccag | agctcagctt | ttaccccaca | ggcttctgga | tatgccaatt | 360 |
| cacttggaca | tcatgctggg | caggtgccat | cttacggtgg | tgcagccttt | aactcaacac | 420 |
| gcgatttcct | tttccgaaat | cgtaactctg | gaattgcaga | ctcatcttct | gcaggcagtc | 480 |
| aacatggact | ttttgccaac | catgggcccc | aggaattggg | tgagccccca | ggacacctga | 540 |
| tcttccccgg | acttcatgag | caaagttcca | gccatacatc | atccaatgga | catgtggtca | 600 |
| atggtcaaat | gcatttagga | ctcagaggag | atattttcgg | acgtccagat | ccttataggg | 660 |
| cagtgcccag | cccgaggaca | gatcattatg | ctgctgccca | attccataat | tataatcaca | 720 |
| tgaatatgag | catgaatgta | gctgctcacc | atggccccgg | ggctttcttt | agatacatga | 780 |
| ggcaacccat | caaacaagag | ttatcgtgta | aatggcttga | ggaatcaaca | atgaaccatc | 840 |
| ctcagaaaac | ctgtgacagg | acatttagca | gcatgcatga | actggttaca | catatgacaa | 900 |
| tggaacatgt | tgggggtcca | gaacaaaata | atcacatatg | ctactgggag | gaatgtccca | 960 |
| ggggaggtaa | atcttttaaa | gcaaagtata | aactagtgaa | tcatatcagg | gtgcataccg | 1020 |
| gagaaaaacc | ctttccatgc | cccttccctg | gatgtgggaa | aatctttgca | cgttcagaaa | 1080 |
| atctcaagat | ccacaaaaga | actcatacag | gtgagaagcc | attcaagtgt | gagtttgaag | 1140 |
| gctgcgatag | aaggtttgca | acagcagcg | acaggaaaaa | acatatgcat | gtgcacacgt | 1200 |
| cagataagcc | atatatctgc | aaagtgtgtg | ataaatccta | cactcacccc | agctccctaa | 1260 |
| gaaagcacat | gaaggttcat | gaatcacaag | ggtctgattc | ttcccctgct | gccagctcag | 1320 |
| ggtacgaatc | tgctacccca | ccagcaatgg | tttctgccaa | cagtgaggaa | ccttccaaaa | 1380 |
| attcatcagc | aacacatcag | actaacaaca | attctcataa | cacaggacta | cttccaccta | 1440 |
| attttaacga | atggtatgtc | tgagcaaaat | gtagagaggc | ctagtcatgc | tcaacaaaag | 1500 |
| gaccatgtgc | aaaaaaacag | aatccaattt | tttttatgtt | gaaccaaggc | ggaaatggaa | 1560 |
| tttaccacac | aagcaacagt | atagggcttc | atcttgttaa | aataatttac | caacattttc | 1620 |
| taaagatggc | tacagactaa | caaagcccctt | ttctcaggat | ctgaacacat | tttttggtgt | 1680 |
| ttgtatttcc | tctgattta | tgcccttttc | attttaacaa | cttcactcct | tttttttttt | 1740 |
| tttaaagaaa | ttaagaggtc | tttagctaat | gtacttaaaa | ttctcttcac | cttttgtggtg | 1800 |
| aatgttaaac | tctcacattc | ttaaacagtg | ccaaagtctt | gttatttctt | gaacctaact | 1860 |
| caaagcatta | cacttgtgaa | tgtattcctt | gtcttatagg | gtcaaagctg | ttgtgtggca | 1920 |
| tatttcaga | aatgggaatg | tgatgttcat | acacagattg | tgaccattta | gtacagttgc | 1980 |
| cttttgtaag | aacttttgta | aatacttatc | cacgatgcca | tatatttatc | atttgtaatt | 2040 |

-continued

```
taattattga tacaagtgcc gggaactgaa caatatttat gagaaaaaaa gtttttctaa    2100
caaaactctg tatagctttt ggttataact gctttagcat taaaaatgat tgttttgaag    2160
aattcccatt taagctgtct aacaaatgtt tgtttacgtc atgcaatgct gaaactaatg    2220
acaatattct gattctgctg tattaattgg tcatcaaaaa ctataatttt tcagcttgtt    2280
tgagcaatac ttgtagatat ataaaatatt taagataaaa tcctatttat tttgaagaat    2340
aaagtataac tgaagtactt gttg                                           2364
```

<210> SEQ ID NO 2
<211> LENGTH: 441
<212> TYPE: PRT
<213> ORGANISM: Xenopus laevis

<400> SEQUENCE: 2

```
Met Thr Met Leu Leu Asp Gly Gly Pro Gln Phe Pro Thr Leu Gly Val
 1               5                  10                  15

Arg Gly Phe Gly Thr Ala Arg His His Glu Met Ser Asn Arg Asp Ala
             20                  25                  30

Gly Met Gly Leu Asn Pro Phe Thr Glu Pro Ser His Ala Ala Ala Phe
         35                  40                  45

Lys Leu Ser Pro Ala Ser His Asp Leu Ser Ser Gln Ser Ser Ala
     50                  55                  60

Phe Thr Pro Gln Ala Ser Gly Tyr Ala Asn Ser Leu Gly His His Ala
 65                  70                  75                  80

Gly Gln Val Pro Ser Tyr Gly Ala Ala Phe Asn Ser Thr Arg Asp
                 85                  90                  95

Phe Leu Phe Arg Asn Arg Asn Ser Gly Ile Ala Asp Ser Ser Ser Ala
            100                 105                 110

Gly Ser Gln His Gly Leu Phe Ala Asn His Gly Pro Pro Gly Ile Gly
        115                 120                 125

Glu Pro Pro Gly His Leu Ile Phe Pro Gly Leu His Glu Gln Ser Ser
    130                 135                 140

Ser His Thr Ser Ser Asn Gly His Val Val Asn Gly Gln Met His Leu
145                 150                 155                 160

Gly Leu Arg Gly Asp Ile Phe Gly Arg Pro Asp Pro Tyr Arg Ala Val
                165                 170                 175

Pro Ser Pro Arg Thr Asp His Tyr Ala Ala Ala Gln Phe His Asn Tyr
            180                 185                 190

Asn His Met Asn Met Ser Met Asn Val Ala Ala His His Gly Pro Gly
        195                 200                 205

Ala Phe Phe Arg Tyr Met Arg Gln Pro Ile Lys Gln Glu Leu Ser Cys
    210                 215                 220

Lys Trp Leu Glu Glu Ser Thr Met Asn His Pro Gln Lys Thr Cys Asp
225                 230                 235                 240

Arg Thr Phe Ser Ser Met His Glu Leu Val Thr His Met Thr Met Glu
                245                 250                 255

His Val Gly Gly Pro Glu Gln Asn Asn His Ile Cys Tyr Trp Glu Glu
            260                 265                 270

Cys Pro Arg Gly Gly Lys Ser Phe Lys Ala Lys Tyr Lys Leu Val Asn
        275                 280                 285

His Ile Arg Val His Thr Gly Glu Lys Pro Phe Pro Cys Pro Phe Pro
    290                 295                 300

Gly Cys Gly Lys Ile Phe Ala Arg Ser Glu Asn Leu Lys Ile His Lys
```

```
305                 310                 315                 320
Arg Thr His Thr Gly Glu Lys Pro Phe Lys Cys Glu Phe Glu Gly Cys
                325                 330                 335
Asp Arg Arg Phe Ala Asn Ser Ser Asp Arg Lys Lys His Met His Val
                340                 345                 350
His Thr Ser Asp Lys Pro Tyr Ile Cys Lys Val Cys Asp Lys Ser Tyr
                355                 360                 365
Thr His Pro Ser Ser Leu Arg Lys His Met Lys Val His Glu Ser Gln
            370                 375                 380
Gly Ser Asp Ser Ser Pro Ala Ala Ser Ser Gly Tyr Glu Ser Ala Thr
385                 390                 395                 400
Pro Pro Ala Met Val Ser Ala Asn Ser Glu Glu Pro Ser Lys Asn Ser
                405                 410                 415
Ser Ala Thr His Gln Thr Asn Asn Asn Ser His Asn Thr Gly Leu Leu
                420                 425                 430
Pro Pro Asn Phe Asn Glu Trp Tyr Val
                435                 440

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic.
      Designed peptide based on amino acid sequence of the zinc finger
      motif of mouse Zic gene family.

<400> SEQUENCE: 3

Glu Asn Leu Lys Ile His Lys
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic.
      Designed peptide based on amino acid sequence of the zinc finger
      motif of mouse Zic gene family.

<400> SEQUENCE: 4

His Met Lys Val His Glu Glu
 1               5

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 5
gagaacctca agatccacaa                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 6
ttyccatgra ccttcatgtg                                              20
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 7
ttctcaggat ctgaacacat                                           20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 8
ccctataaga caaggaatac                                           20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 9
ggactctcgc cttgtggc                                             18

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 10
gatatgttct tgtaatagtc agt                                       23

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 11
tggacctcag gccatgttc                                            19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 12
gatgctgagt ggaggtgtta                                           20

<210> SEQ ID NO 13
<211> LENGTH: 22
<212> TYPE: DNA
<213> ORGANISM: Artificial Sequence
<220> FEATURE:

-continued

<223> OTHER INFORMATION: Description of Artificial Sequence: Synthetic

<400> SEQUENCE: 13
acccaacgac cacgtggacc tg                                          22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 14
agctcattgc aggaggtgtc tg                                          22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 15
gtgaaatccc aatagacacc                                             20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 16
ttccccatat ctaaaggcag                                             20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 17
cacagttcca ccaaatgc                                               18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 18
ggaatcaagc ggtacaga                                               18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 19
acacggcatt gatcctacag                                             20

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 20
agctccttcg gtgtaatgac                                              20

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 21
cgggataaca ttcagggtat cact                                         24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 22
atccatggcg gtaactgtct tcct                                         24

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 23
aactgccagg actggatggt                                              20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 24
ggcaggattt agagttgctt c                                            21

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 25
caccagaaca cagagtac                                                18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
```

<400> SEQUENCE: 26
caaccttccc atcaacca                                                    18

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 27
agtccgatct cagtgaaggg ca                                               22

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 28
tgtgtgtggc ctgagctgta g                                                21

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 29
gccctatttc cttgttgc                                                    18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 30
aacccttctt ggttgcac                                                    18

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 31
caagagcgga gaaactgtgt                                                  20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 32
gaaggagcaa caagaggaag                                                  20

<210> SEQ ID NO 33
<211> LENGTH: 20

```
<212> TYPE: DNA
<213> ORGANISM: Artificial Sequence
<220> FEATURE:
<223> OTHER INFORMATION: Description of Artificial Sequence: Synthetic

<400> SEQUENCE: 33
gtccgtacac tcacagaaac                                                    20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 34
gaggtgtaga gccaagtaag                                                    20

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 35
gctgacagaa tgcagaag                                                      18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 36
ttgcttggag gagtgtgt                                                      18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 37 cacaagggt taaaggcaag                                                     20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 38
cccagtgtct ctctcagtat                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 39
```

```
tacttacggg cttggctgga                                               20
```

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:  Synthetic

<400> SEQUENCE: 40

```
agcgtgtaac cagttggctg                                               20
```

<210> SEQ ID NO 41
<211> LENGTH: 1825
<212> TYPE: DNA
<213> ORGANISM: Xenopus laevis

<400> SEQUENCE: 41

```
caacggccgg ctgaggaggt gaaagtttct ccccaggaac ataaaccgca aaagacaata    60
ttgtgcgtga tttgcgcttc gcagggagag agggaaaaga aacaacaaca acaataataa   120
taataataat aacaagagcg gtgtcggtg agaagtggaa caaattggca tttcctagtc    180
agcccagtgt cagtggtcgg tgtgttgtag ctcagaggcg cgccatgcag cagtagatgc   240
gactgtcctg aagtcggtgc gattgtgcca tctgcacgtg cacaagtgta cgacccccc    300
tgctgcccgt gtggccgctc attcgctgcc cattgttgga agacttgcca ccatgctgct   360
ggacgccgga gcccaatacc cagcgatcgg agtgacgact ttcggttcct ccaggcacca   420
ctcggctggc gatgtgacgg atcgagaggt ggccctgggc atcaatccct tcgcagacgg   480
catgggagct ttcaaaactca acccgagtag ccacgatctc gcctcaggtc agaccgcttt   540
cacttcgcag gctccgggct acgctgcggc cgctctgggg caccatcatc acccgggaca   600
tgtcagctct tactccagcg ctgcctttaa ctccacccgg gactttctct tccgcaaccg   660
gggcttcggg gaggccgcca gcgcccagca cagtctattc gcctccgccg cgggggggctt   720
ccccggaccc catgggcccc acgctgatac cacgggccac ttgattttcc ctggactcca   780
cgagcaagca gccagccacg cttctcccaa tgtggtgaac ggacagatga ggctgggctt   840
ctcgggggac atgtatggca gcccgaccca gtacggacag gtgactagcc ccaggtctga   900
gcattatgcc tccagccaac tgcacggcta cggccctatg aacatgaaca tggctgccca   960
ccatggagca ggggctttct tccgttacat gaggcagccc atcaagcaag agctcatctg  1020
caaatggatt gagcccgagc agttggccaa ccccaaaaag tcgtgcaaca aaactttcag  1080
taccatgcac gagctggtca cccatgttac tgtggagcac gttgggggcc cagagcagtc  1140
caaccacatc tgtgtctggg aagaatgtcc aagagaaggg aaacctttca aggccaaata  1200
caaactgatc aaccacatca gagtgcacac aggcgaaaag cctttccctt gcccttccc   1260
tggatgtggc aaagtctttg cgcgatcaga aaatctcaag atccacaaaa gaactcacac  1320
aggtgaaaaa ccctttaagt gcgagtttga aggctgtgac agacgatttg ccaatagcag  1380
tgatcgtaaa aagcacatgc acgttcatac atcggacaag ccgtatctgt gtaaaatgtg  1440
cgacaagtcg tacacccacc ccagctccct caggaagcac atgaaggtcc acgaagcatc  1500
ttcccaaggg tctcagcctt ccccagcagc cagttcaggc tatgaatctt caacgccccc  1560
aacaatcgtt tctccttctg cagaaaacca gagcacaagt tccttatccc ccagctcctc  1620
agcagtacat cacacgtcca atcacagcac gctctcgtca aattttaacg aatggtacgt  1680
ttaaacacat atttaaaaca aaaagagactt caaataaatg aacacttcca aggtaatatc  1740
```

```
ctaaatctgc aatagaaacc gggaccgaat aaaatgaaga atgagacctt ttttttttaa    1800
ttcctgcagg cttggtaaga aaaaa                                         1825
```

<210> SEQ ID NO 42
<211> LENGTH: 443
<212> TYPE: PRT
<213> ORGANISM: Xenopus laevis

<400> SEQUENCE: 42

```
Met Leu Leu Asp Ala Gly Ala Gln Tyr Pro Ala Ile Gly Val Thr Thr
  1               5                  10                  15

Phe Gly Ser Ser Arg His His Ser Ala Gly Asp Val Thr Asp Arg Glu
             20                  25                  30

Val Ala Leu Gly Ile Asn Pro Phe Ala Asp Gly Met Gly Ala Phe Lys
         35                  40                  45

Leu Asn Pro Ser Ser His Asp Leu Ala Ser Gly Gln Thr Ala Phe Thr
     50                  55                  60

Ser Gln Ala Pro Gly Tyr Ala Ala Ala Leu Gly His His His His
 65                  70                  75                  80

Pro Gly His Val Ser Ser Tyr Ser Ser Ala Ala Phe Asn Ser Thr Arg
                 85                  90                  95

Asp Phe Leu Phe Arg Asn Arg Gly Phe Gly Glu Ala Ala Ser Ala Gln
            100                 105                 110

His Ser Leu Phe Ala Ser Ala Gly Gly Phe Pro Gly Pro His Gly
        115                 120                 125

Pro His Ala Asp Thr Thr Gly His Leu Ile Phe Pro Gly Leu His Glu
    130                 135                 140

Gln Ala Ala Ser His Ala Ser Pro Asn Val Val Asn Gly Gln Met Arg
145                 150                 155                 160

Leu Gly Phe Ser Gly Asp Met Tyr Gly Arg Pro Asp Gln Tyr Gly Gln
                165                 170                 175

Val Thr Ser Pro Arg Ser Glu His Tyr Ala Ser Ser Gln Leu His Gly
            180                 185                 190

Tyr Gly Pro Met Asn Met Asn Met Ala Ala His His Gly Ala Gly Ala
        195                 200                 205

Phe Phe Arg Tyr Met Arg Gln Pro Ile Lys Gln Glu Leu Ile Cys Lys
    210                 215                 220

Trp Ile Glu Pro Glu Gln Leu Ala Asn Pro Lys Lys Ser Cys Asn Lys
225                 230                 235                 240

Thr Phe Ser Thr Met His Glu Leu Val Thr His Val Thr Val Glu His
                245                 250                 255

Val Gly Gly Pro Glu Gln Ser Asn His Ile Cys Val Trp Glu Glu Cys
            260                 265                 270

Pro Arg Glu Gly Lys Pro Phe Lys Ala Lys Tyr Lys Leu Ile Asn His
        275                 280                 285

Ile Arg Val His Thr Gly Glu Lys Pro Phe Pro Cys Pro Phe Pro Gly
    290                 295                 300

Cys Gly Lys Val Phe Ala Arg Ser Glu Asn Leu Lys Ile His Lys Arg
305                 310                 315                 320

Thr His Thr Gly Glu Lys Pro Phe Lys Cys Glu Phe Glu Gly Cys Asp
                325                 330                 335

Arg Arg Phe Ala Asn Ser Ser Asp Arg Lys Lys His Met His Val His
            340                 345                 350
```

```
Thr Ser Asp Lys Pro Tyr Leu Cys Lys Met Cys Asp Lys Ser Tyr Thr
            355                 360                 365

His Pro Ser Ser Leu Arg Lys His Met Lys Val His Glu Ala Ser Ser
            370                 375                 380

Gln Gly Ser Gln Pro Ser Pro Ala Ala Ser Ser Gly Tyr Glu Ser Ser
385                 390                 395                 400

Thr Pro Pro Thr Ile Val Ser Pro Ser Ala Glu Asn Gln Ser Thr Ser
                405                 410                 415

Ser Leu Ser Pro Ser Ser Ser Ala Val His His Thr Ser Asn His Ser
            420                 425                 430

Thr Leu Ser Ser Asn Phe Asn Glu Trp Tyr Val
            435                 440

<210> SEQ ID NO 43
<211> LENGTH: 2901
<212> TYPE: DNA
<213> ORGANISM: Xenopus laevis

<400> SEQUENCE: 43
```

| | | | | | |
|---|---|---|---|---|---|
| ctcagtgctc | gtttgttatg | acccttttgc | tttctttttt | ttcctctcgg | tttctccaag |   60 |
| cagcacccccc | ttgtgaagct | tcctcccctc | tatccctccc | cctcccccca | ccatcctgag |  120 |
| ctgcaactta | agaaagaag | aagaggagag | agaggagcat | ctgccgcccg | gtccttcatc |  180 |
| tgggggaat | gtggactaag | ttccccgcat | gagaacgagg | cggaggcgga | tgataatgat |  240 |
| gagagcaagt | ggagcaggac | tcgtctagat | tcactcccag | caccaggata | cacatttata |  300 |
| ctcgcggcat | ctggaatccc | ttcatcaccc | gttattatta | tttgtagcat | tttgtatttg |  360 |
| tacgttttgc | ttttatgccc | atcctgtgca | cttccacagc | agagtctcgc | cactgacact |  420 |
| cagtactgac | cctgggcaca | gtcgcacgga | catgctacta | gacgctggtc | cccagttccc |  480 |
| ggccctgggt | gtgggcacat | ttgcccgaca | tcaccaccat | catcaccatg | cagcggtagc |  540 |
| ggcggcggca | gcagcagccg | cagagatgca | ggagagggag | ctgagtctgg | cgcagaacac |  600 |
| tttcgtggaa | cctactcaca | tgggcgcatt | taagctgaat | cccggcggtg | gctccggggg |  660 |
| agggagcggc | ggcggcggtg | gaggaggagg | agccggtcca | aatgggggag | ccggggccag |  720 |
| tggaccccac | gatttgtccc | ccccagggca | gacttctgct | ttcacctcac | aagccggtta |  780 |
| ccccacctcc | gccctggcac | cccattcagc | ctactctgga | gccgctgcct | tcaacagccc |  840 |
| acgggacttt | ttattccgcg | gacgcggttt | cgcagaggga | tcggcagctg | cgggcggggg |  900 |
| gcagcacggc | ttgtttgggc | ccccagcggg | aagtcttcac | caccatccgc | accaccacca |  960 |
| ccagctctcc | cacgcggagc | acccgcaagg | acacctacta | ttccccggga | ttcacgatca | 1020 |
| acacgcggct | gcctcccaga | acacattggg | tggccagatg | cgccttggtt | tgcccggaga | 1080 |
| ggtgttcggt | aggacggagc | aataccgcca | ggtatccagc | cccaggggg | acccatacac | 1140 |
| agccgcccag | ctgcacaacc | agtactcccc | tatgaacatg | ggcatgaaca | tggcagccca | 1200 |
| ccaccatcat | catcaccacc | accacccggg | ggccttcttc | aggtacatga | dacaaccgtg | 1260 |
| catcaagcag | gagctcatct | gtaagtggat | cgaccccgag | caactcaaca | accccaagaa | 1320 |
| aagctgcacc | aaaaccttca | gcacaatgca | cgaactcgtt | actcatgtgt | ctgtggagca | 1380 |
| cgtcgggggg | ccagagcaga | gcaaccatat | ctgcttctgg | gaggagtgtc | ctagggaggg | 1440 |
| aaagccgttc | aaagccaaat | acaaactggt | gaatcacatc | agagtacaca | ctggcgagaa | 1500 |
| gcccttccct | tgccccttcc | ctggatgcgg | caaagtcttt | gcaagatcgg | aaaatctcaa | 1560 |
| aatccacaaa | aggacgcaca | caggagagaa | gcccttccag | tgcgaatttg | aaggctgcga | 1620 |

-continued

```
caggcgattt gcgaacagca gcgacaggaa gaagcacatg cacgtgcaca cctcggacaa    1680
accctatctg tgtaagatgt gcgacaaaac gtacactcat cccagctctc taagaaaaca    1740
catgaaggtg catgaaactt ctccccaagg ctcagagtcc tctccggctg ccagttctgg    1800
ctatgaatcc tccaccccac caggtctggt ctccccaaat tctgaaacga gaacccccaa    1860
cttgtcccca gcagcagcgg cggtgtctgc agtacacaat gtgtccagcg gggctagcgg    1920
agccctcgca tcaaacttca atgaatggta tgtgtagggg acacgcttct acttccctgg    1980
gacaactgtt cggccactag agacttttt tgtggtcaca gcttcaccag cgataaaccc    2040
agaacttaaa caacggcagc gttatctcct aggagacacc caccagcaag gattacatcc    2100
gaaccattca gtgcgcacac agatatttat ccgcatggag agagtaaatc acccaacaga    2160
atgtatttat ttcccctccc caaaagaaaa cgtgttatta ctcctcaagg tgtgaataca    2220
gagttgataa aaaaaaacac ccgcaaagga catgttgatg gatgcctccc tcggtgtata    2280
tacaatttgt tcggttttta gattgtttta cataatatat gatggacgta cccttcattc    2340
acctgtttaa tatgaagctt atttaatttt cttttattag aggaatcctg acttgtcatt    2400
tttagtgccc cggaatggag ggggacacaa cgagtgccaa agtctccaga tggttcctac    2460
aaaactaaaa aaaaaaaagg caggcatttc tacaaaaggc ttgtgaatgt acttttctgt    2520
taaatgggct ttatgtgatg ttttctgtgc ttttgcaagt tgaatttgtt agttactgtt    2580
tggaaaagcg ccgaggcaaa aataagtagc cgttgtgcag tcaccctata gcagcctttc    2640
ttgtgtaaaa aataaatcgc taccatattt atccatttgt aattaaatta tggtatgaac    2700
ttgcaacaga ggaaacacta tttataaaga ttgtttcttg actataaata tgtacatttg    2760
tgagcataaa tgttttcaga tttttttttt tcttatttta tgtggtctct acattttgt    2820 gacatgtttt aaaagtaatg catacagacc tcctaataaa atgtgttgaa actgcgacat    2880
caaacaccaa aaaaaaaaa a                                               2901
```

<210> SEQ ID NO 44
<211> LENGTH: 501
<212> TYPE: PRT
<213> ORGANISM: Xenopus laevis

<400> SEQUENCE: 44

```
Met Leu Leu Asp Ala Gly Pro Gln Phe Pro Ala Leu Gly Val Gly Thr
 1               5                  10                  15

Phe Ala Arg His His His His His His Ala Ala Val Ala Ala Ala
                20                  25                  30

Ala Ala Ala Ala Glu Met Gln Glu Arg Glu Leu Ser Leu Ala Gln
        35                  40                  45

Asn Thr Phe Val Glu Pro Thr His Met Gly Ala Phe Lys Leu Asn Pro
    50                  55                  60

Gly Gly Gly Ser Gly Gly Gly Ser Gly Gly Gly Gly Gly Gly Gly Gly
65                  70                  75                  80

Ala Gly Pro Asn Gly Gly Ala Gly Ala Ser Gly Pro His Asp Leu Ser
                85                  90                  95

Pro Pro Gly Gln Thr Ser Ala Phe Thr Ser Gln Ala Gly Tyr Pro Thr
            100                 105                 110

Ser Ala Leu Ala Pro His Ser Ala Tyr Ser Gly Ala Ala Ala Phe Asn
        115                 120                 125

Ser Pro Arg Asp Phe Leu Phe Arg Gly Arg Gly Phe Ala Glu Gly Ser
    130                 135                 140
```

```
Ala Ala Ala Gly Gly Gly Gln His Gly Leu Phe Gly Pro Pro Ala Gly
145                 150                 155                 160

Ser Leu His His His Pro His His His Gln Leu Ser His Ala Glu
            165                 170                 175

His Pro Gln Gly His Leu Leu Phe Pro Gly Ile His Asp Gln His Ala
            180                 185                 190

Ala Ala Ser Gln Asn Thr Leu Gly Gly Gln Met Arg Leu Gly Leu Pro
            195                 200                 205

Gly Glu Val Phe Gly Arg Thr Glu Gln Tyr Arg Gln Val Ser Ser Pro
            210                 215                 220

Arg Gly Asp Pro Tyr Thr Ala Ala Gln Leu His Asn Gln Tyr Ser Pro
225                 230                 235                 240

Met Asn Met Gly Met Asn Met Ala Ala His His His His His His
                245                 250                 255

His His Pro Gly Ala Phe Phe Arg Tyr Met Arg Gln Pro Cys Ile Lys
            260                 265                 270

Gln Glu Leu Ile Cys Lys Trp Ile Asp Pro Glu Gln Leu Asn Asn Pro
            275                 280                 285

Lys Lys Ser Cys Thr Lys Thr Phe Ser Thr Met His Glu Leu Val Thr
            290                 295                 300

His Val Ser Val Glu His Val Gly Gly Pro Glu Gln Ser Asn His Ile
305                 310                 315                 320

Cys Phe Trp Glu Glu Cys Pro Arg Glu Gly Lys Pro Phe Lys Ala Lys
            325                 330                 335

Tyr Lys Leu Val Asn His Ile Arg Val His Thr Gly Glu Lys Pro Phe
            340                 345                 350

Pro Cys Pro Phe Pro Gly Cys Gly Lys Val Phe Ala Arg Ser Glu Asn
            355                 360                 365

Leu Lys Ile His Lys Arg Thr His Thr Gly Glu Lys Pro Phe Gln Cys
            370                 375                 380

Glu Phe Glu Gly Cys Asp Arg Arg Phe Ala Asn Ser Ser Asp Arg Lys
385                 390                 395                 400

Lys His Met His Val His Thr Ser Asp Lys Pro Tyr Leu Cys Lys Met
            405                 410                 415

Cys Asp Lys Thr Tyr Thr His Pro Ser Ser Leu Arg Lys His Met Lys
            420                 425                 430

Val His Glu Thr Ser Pro Gln Gly Ser Glu Ser Ser Pro Ala Ala Ser
            435                 440                 445

Ser Gly Tyr Glu Ser Ser Thr Pro Pro Gly Leu Val Ser Pro Asn Ser
            450                 455                 460

Glu Thr Gln Asn Pro Asn Leu Ser Pro Ala Ala Ala Val Ser Ala
465                 470                 475                 480

Val His Asn Val Ser Ser Gly Ala Ser Gly Ala Leu Ala Ser Asn Phe
            485                 490                 495

Asn Glu Trp Tyr Val
            500

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 45
```

```
atgaaggtcc acgaagcatc                                              20
```

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 46

```
cgtgctgtga ttggacgtgt                                              20
```

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 47

```
acggcagcgt tatctcctag                                              20
```

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 48

```
tataccccga gggaggcatc                                              20
```

<210> SEQ ID NO 49
<211> LENGTH: 10
<212> TYPE: PRT
<213> ORGANISM: Xenopus laevis
<220> FEATURE:
<221> NAME/KEY: SITE
<222> LOCATION: (9)
<223> OTHER INFORMATION: The amino acid at this position can be
      Asparagine, Glycine, or Glutamine.

<400> SEQUENCE: 49

```
Phe Asn Ser Thr Arg Asp Phe Arg Xaa Arg
 1               5                  10
```

<210> SEQ ID NO 50
<211> LENGTH: 179
<212> TYPE: PRT
<213> ORGANISM: Xenopus laevis
<220> FEATURE:
<223> OTHER INFORMATION: Zic1; zinc finger domain

<400> SEQUENCE: 50

```
Gly Ala Gly Ala Phe Phe Arg Tyr Met Arg Gln Pro Ile Lys Gln Glu
 1               5                  10                  15

Leu Ile Cys Lys Trp Ile Glu Pro Glu Gln Leu Ala Asn Pro Lys Lys
            20                  25                  30

Ser Cys Asn Lys Thr Phe Ser Thr Met His Glu Leu Val Thr His Val
        35                  40                  45

Thr Val Glu His Val Gly Gly Pro Glu Gln Ser Asn His Ile Cys Val
    50                  55                  60

Trp Glu Glu Cys Pro Arg Glu Gly Lys Pro Phe Lys Ala Lys Tyr Lys
65                  70                  75                  80
```

-continued

Leu Ile Asn His Ile Arg Val His Thr Gly Glu Lys Pro Phe Pro Cys
                85                  90                  95

Pro Phe Pro Gly Cys Gly Lys Val Phe Ala Arg Ser Glu Asn Leu Lys
            100                 105                 110

Ile His Lys Arg Thr His Thr Gly Glu Lys Pro Phe Lys Cys Glu Phe
        115                 120                 125

Glu Gly Cys Asp Arg Arg Phe Ala Asn Ser Ser Asp Arg Lys Lys His
    130                 135                 140

Met His Val His Thr Ser Asp Lys Pro Tyr Leu Cys Lys Met Cys Asp
145                 150                 155                 160

Lys Ser Tyr Thr His Pro Ser Ser Leu Arg Lys His Met Lys Val His
                165                 170                 175

Glu Ala Ser

<210> SEQ ID NO 51
<211> LENGTH: 180
<212> TYPE: PRT
<213> ORGANISM: Xenopus laevis
<220> FEATURE:
<223> OTHER INFORMATION: Zic2; zinc finger domain

<400> SEQUENCE: 51

His Pro Gly Ala Phe Phe Arg Tyr Met Arg Gln Pro Cys Ile Lys Gln
 1               5                  10                  15

Glu Leu Ile Cys Lys Trp Ile Asp Pro Glu Gln Leu Asn Asn Pro Lys
            20                  25                  30

Lys Ser Cys Thr Lys Thr Phe Ser Thr Met His Glu Leu Val Thr His
        35                  40                  45

Val Ser Val Glu His Val Gly Gly Pro Glu Gln Ser Asn His Ile Cys
    50                  55                  60

Phe Trp Glu Glu Cys Pro Arg Glu Gly Lys Pro Phe Lys Ala Lys Tyr
65                  70                  75                  80

Lys Leu Val Asn His Ile Arg Val His Thr Gly Glu Lys Pro Phe Pro
                85                  90                  95

Cys Pro Phe Pro Gly Cys Gly Lys Val Phe Ala Arg Ser Glu Asn Leu
            100                 105                 110

Lys Ile His Lys Arg Thr His Thr Gly Glu Lys Pro Phe Gln Cys Glu
        115                 120                 125

Phe Glu Gly Cys Asp Arg Arg Phe Ala Asn Ser Ser Asp Arg Lys Lys
    130                 135                 140

His Met His Val His Thr Ser Asp Lys Pro Tyr Leu Cys Lys Met Cys
145                 150                 155                 160

Asp Lys Thr Tyr Thr His Pro Ser Ser Leu Arg Lys His Met Lys Val
                165                 170                 175

His Glu Thr Ser
            180

<210> SEQ ID NO 52
<211> LENGTH: 179
<212> TYPE: PRT
<213> ORGANISM: Xenopus laevis
<220> FEATURE:
<223> OTHER INFORMATION: Zic3; zinc finger domain

<400> SEQUENCE: 52

Gly Pro Gly Ala Phe Phe Arg Tyr Met Arg Gln Pro Ile Lys Gln Glu
 1               5                  10                  15

```
Leu Ser Cys Lys Trp Leu Glu Glu Ser Thr Met Asn His Pro Gln Lys
            20                  25                  30

Thr Cys Asp Arg Thr Phe Ser Ser Met His Glu Leu Val Thr His Met
        35                  40                  45

Thr Met Glu His Val Gly Gly Pro Glu Gln Asn Asn His Ile Cys Tyr
    50                  55                  60

Trp Glu Glu Cys Pro Arg Gly Gly Lys Ser Phe Lys Ala Lys Tyr Lys
65                  70                  75                  80

Leu Val Asn His Ile Arg Val His Thr Gly Lys Pro Phe Pro Cys
            85                  90                  95

Pro Phe Pro Gly Cys Gly Lys Ile Phe Ala Arg Ser Glu Asn Leu Lys
            100                 105                 110

Ile His Lys Arg Thr His Thr Gly Glu Lys Pro Phe Lys Cys Glu Phe
        115                 120                 125

Glu Gly Cys Asp Arg Arg Phe Ala Asn Ser Ser Asp Arg Lys Lys His
    130                 135                 140

Met His Val His Thr Ser Asp Lys Pro Tyr Ile Cys Lys Val Cys Asp
145                 150                 155                 160

Lys Ser Tyr Thr His Pro Ser Ser Leu Arg Lys His Met Lys Val His
                165                 170                 175

Glu Ser Gln

<210> SEQ ID NO 53
<211> LENGTH: 179
<212> TYPE: PRT
<213> ORGANISM: Mus musculus
<220> FEATURE:
<223> OTHER INFORMATION: Zic1; zinc finger domain

<400> SEQUENCE: 53

Gly Ala Gly Ala Phe Phe Arg Tyr Met Arg Gln Pro Ile Lys Gln Glu
1               5                   10                  15

Leu Ile Cys Lys Trp Ile Glu Pro Glu Gln Leu Ala Asn Pro Lys Lys
            20                  25                  30

Ser Cys Asn Lys Thr Phe Ser Thr Met His Glu Leu Val Thr His Val
        35                  40                  45

Thr Val Glu His Val Gly Gly Pro Glu Gln Ser Asn His Ile Cys Phe
    50                  55                  60

Trp Glu Glu Cys Pro Arg Glu Gly Lys Pro Phe Lys Ala Lys Tyr Lys
65                  70                  75                  80

Leu Val Asn His Ile Arg Val His Thr Gly Glu Lys Pro Phe Pro Cys
            85                  90                  95

Pro Phe Pro Gly Cys Gly Lys Val Phe Ala Arg Ser Glu Asn Leu Lys
            100                 105                 110

Ile His Lys Arg Thr His Thr Gly Glu Lys Pro Phe Lys Cys Glu Phe
        115                 120                 125

Glu Gly Cys Asp Arg Arg Phe Ala Asn Ser Ser Asp Arg Lys Lys His
    130                 135                 140

Met His Val His Thr Ser Asp Lys Pro Tyr Leu Cys Lys Met Cys Asp
145                 150                 155                 160

Lys Ser Tyr Thr His Pro Ser Ser Leu Arg Lys His Met Lys Val His
                165                 170                 175

Glu Ser Ser
```

-continued

```
<210> SEQ ID NO 54
<211> LENGTH: 179
<212> TYPE: PRT
<213> ORGANISM: Mus musculus
<220> FEATURE:
<223> OTHER INFORMATION: Zic2; zinc finger domain

<400> SEQUENCE: 54

Gly Ala Gly Ala Phe Phe Arg Tyr Met Arg Gln Pro Ile Lys Gln Glu
 1               5                  10                  15

Leu Ile Cys Lys Trp Ile Glu Pro Glu Gln Leu Ala Asn Pro Lys Lys
            20                  25                  30

Ser Cys Asn Lys Thr Phe Ser Thr Met His Glu Leu Val Thr His Val
        35                  40                  45

Thr Val Glu His Val Gly Gly Pro Glu Gln Ser Asn His Ile Cys Phe
 50                  55                  60

Trp Glu Glu Cys Pro Arg Glu Gly Lys Pro Phe Lys Ala Lys Tyr Lys
 65                  70                  75                  80

Leu Val Asn His Ile Arg Val His Thr Gly Glu Lys Pro Phe Pro Cys
                85                  90                  95

Pro Phe Pro Gly Cys Gly Lys Val Phe Ala Arg Ser Glu Asn Leu Lys
            100                 105                 110

Ile His Lys Arg Thr His Thr Gly Glu Lys Pro Phe Lys Cys Glu Phe
        115                 120                 125

Glu Gly Cys Asp Arg Arg Phe Ala Asn Ser Ser Asp Arg Lys Lys His
130                 135                 140

Met His Val His Thr Ser Asp Lys Pro Tyr Leu Cys Lys Met Cys Asp
145                 150                 155                 160

Lys Ser Tyr Thr His Pro Ser Ser Leu Arg Lys His Met Lys Val His
                165                 170                 175

Glu Ser Ser

<210> SEQ ID NO 55
<211> LENGTH: 179
<212> TYPE: PRT
<213> ORGANISM: Mus musculus
<220> FEATURE:
<223> OTHER INFORMATION: Zic3; zinc finger domain

<400> SEQUENCE: 55

Gly Pro Gly Ala Phe Phe Arg Tyr Met Arg Gln Pro Ile Lys Gln Glu
 1               5                  10                  15

Leu Ser Cys Lys Trp Ile Glu Glu Ala Gln Leu Ser Arg Pro Lys Lys
            20                  25                  30

Ser Cys Asp Arg Thr Phe Ser Thr Met His Glu Leu Val Thr His Val
        35                  40                  45

Thr Met Glu His Val Gly Gly Pro Glu Gln Asn Asn His Val Cys Tyr
 50                  55                  60

Trp Glu Glu Cys Pro Arg Glu Gly Lys Ser Phe Lys Ala Lys Tyr Lys
 65                  70                  75                  80

Leu Val Asn His Ile Arg Val His Thr Gly Glu Lys Pro Phe Pro Cys
                85                  90                  95

Pro Phe Pro Gly Cys Gly Lys Ile Phe Ala Arg Ser Glu Asn Leu Lys
            100                 105                 110

Ile His Lys Arg Thr His Thr Gly Glu Lys Pro Phe Lys Cys Glu Phe
        115                 120                 125

Glu Gly Cys Asp Arg Arg Phe Ala Asn Ser Ser Asp Arg Lys Lys His
```

```
              130                 135                 140
Met His Val His Thr Ser Asp Lys Pro Tyr Ile Cys Lys Val Cys Asp
145                 150                 155                 160

Lys Ser Tyr Thr His Pro Ser Ser Leu Arg Lys His Met Lys Val His
                165                 170                 175

Glu Ser Gln

<210> SEQ ID NO 56
<211> LENGTH: 180
<212> TYPE: PRT
<213> ORGANISM: Mus musculus
<220> FEATURE:
<223> OTHER INFORMATION: Zic4; zinc finger domain

<400> SEQUENCE: 56

Gly Pro Gly Ala Phe Phe Arg Tyr Met Arg Gln Pro Ile Lys Gln Glu
  1               5                  10                  15

Leu Ile Cys Lys Trp Leu Gly Asp Asp Ser Pro Met Ser Pro Arg Pro
                 20                  25                  30

Cys Ser Lys Thr Phe Ser Thr Met His Glu Leu Val Thr His Val Thr
                 35                  40                  45

Val Glu His Val Gly Gly Pro Glu Gln Ala Asn His Ile Cys Phe Trp
 50                  55                  60

Glu Glu Cys Pro Arg Gln Gly Lys Pro Phe Lys Ala Lys Tyr Lys Leu
 65                  70                  75                  80

Val Asn His Ile Arg Val His Thr Gly Glu Lys Pro Phe Pro Cys Pro
                 85                  90                  95

Phe Pro Gly Cys Gly Lys Val Phe Ala Arg Ser Glu Asn Leu Lys Ile
                100                 105                 110

His Lys Arg Thr His Thr Gly Glu Lys Pro Phe Arg Cys Glu Phe Glu
                115                 120                 125

Gly Cys Glu Arg Arg Phe Ala Asn Ser Ser Asp Arg Lys Lys His Ser
                130                 135                 140

His Val His Thr Ser Asp Lys Pro Tyr Met Cys Lys Val Arg Gly Cys
145                 150                 155                 160

Asp Lys Cys Tyr Thr His Pro Ser Ser Leu Arg Lys His Met Lys Val
                165                 170                 175

His Gly Arg Ser
            180

<210> SEQ ID NO 57
<211> LENGTH: 192
<212> TYPE: PRT
<213> ORGANISM: Drosophila melanogaster
<220> FEATURE:
<223> OTHER INFORMATION: Opa; zinc finger domain

<400> SEQUENCE: 57

Gly Ala Gly Ala Phe Leu Arg Tyr Met Arg His Gln Pro Ala Ser Ser
  1               5                  10                  15

Ala Ser Ser Val Lys Gln Glu Met Gln Cys Leu Trp Ile Asp Pro Asp
                 20                  25                  30

Gln Pro Gly Leu Val Pro Pro Gly Gly Arg Lys Thr Cys Asn Lys Val
                 35                  40                  45

Phe His Ser Met His Glu Ile Val Thr His Leu Thr Val Glu His Val
                 50                  55                  60

Gly Gly Pro Glu Cys Thr Thr His Ala Cys Phe Trp Val Gly Cys Ser
```

```
                65                  70                  75                  80
Arg Asn Gly Arg Pro Phe Lys Ala Lys Tyr Lys Leu Val Asn His Ile
                    85                  90                  95

Arg Val His Thr Gly Glu Lys Pro Phe Ala Cys Pro His Pro Gly Cys
                100                 105                 110

Gly Lys Val Phe Ala Arg Ser Glu Asn Leu Lys Ile His Lys Arg Thr
                115                 120                 125

His Thr Gly Glu Lys Pro Phe Lys Cys Glu His Glu Gly Cys Asp Arg
        130                 135                 140

Arg Phe Ala Asn Ser Ser Asp Arg Lys Lys His Ser His Val His Thr
145                 150                 155                 160

Ser Asp Lys Pro Tyr Asn Cys Arg Ile Asn Gly Cys Asp Lys Ser Tyr
                165                 170                 175

Thr His Pro Ser Ser Leu Arg Lys His Met Lys Val His Gly Asn Val
                180                 185                 190
```

<210> SEQ ID NO 58
<211> LENGTH: 12
<212> TYPE: PRT
<213> ORGANISM: Xenopus laevis
<220> FEATURE:
<223> OTHER INFORMATION: Zic 1; conserved N-terminal region

<400> SEQUENCE: 58

```
Phe Asn Ser Thr Arg Asp Phe Leu Phe Arg Asn Arg
 1               5                  10
```

<210> SEQ ID NO 59
<211> LENGTH: 13
<212> TYPE: PRT
<213> ORGANISM: Xenopus laevis
<220> FEATURE:
<223> OTHER INFORMATION: Zic2; conserved N-terminal region

<400> SEQUENCE: 59

```
Phe Asn Ser Pro Arg Asp Phe Leu Phe Arg Gly Arg Gly
 1               5                  10
```

<210> SEQ ID NO 60
<211> LENGTH: 12
<212> TYPE: PRT
<213> ORGANISM: Xenopus laevis
<220> FEATURE:
<223> OTHER INFORMATION: Zic3; conserved N-terminal region

<400> SEQUENCE: 60

```
Phe Asn Ser Thr Arg Asp Phe Leu Phe Arg Asn Arg
 1               5                  10
```

<210> SEQ ID NO 61
<211> LENGTH: 12
<212> TYPE: PRT
<213> ORGANISM: Mus musculus
<220> FEATURE:
<223> OTHER INFORMATION: Zic1; conserved N-terminal region

<400> SEQUENCE: 61

```
Phe Asn Ser Thr Arg Asp Phe Leu Phe Arg Asn Arg
 1               5                  10
```

<210> SEQ ID NO 62
<211> LENGTH: 12
<212> TYPE: PRT

```
<213> ORGANISM: Mus musculus
<220> FEATURE:
<223> OTHER INFORMATION: Zic2; conserved N-terminal region

<400> SEQUENCE: 62

Phe Asn Ser Thr Arg Asp Phe Leu Phe Arg Ser Arg
 1               5                  10

<210> SEQ ID NO 63
<211> LENGTH: 12
<212> TYPE: PRT
<213> ORGANISM: Mus musculus
<220> FEATURE:
<223> OTHER INFORMATION: Zic3; conserved N-terminal region

<400> SEQUENCE: 63

Phe Asn Ser Thr Arg Asp Phe Leu Phe Arg Gln Arg
 1               5                  10

<210> SEQ ID NO 64
<211> LENGTH: 14
<212> TYPE: PRT
<213> ORGANISM: Drosophila melanogaster
<220> FEATURE:
<223> OTHER INFORMATION: Opa; conserved N-terminal region

<400> SEQUENCE: 64

Phe Asn Ser Tyr Ala Ser Arg Asp Phe Leu Leu Gly Arg Arg
 1               5                  10
```